United States Patent
Shiota et al.

(10) Patent No.: US 6,686,353 B1
(45) Date of Patent: Feb. 3, 2004

(54) DIARYLALKYL CYCLIC DIAMINE DERIVATIVES AS CHEMOKINE RECEPTOR ANTAGONISTS

(75) Inventors: Tatsuki Shiota, Kanagawa (JP); Shinsuke Yamagami, Tokyo (JP); Kenichiro Kataoka, Tokyo (JP); Noriaki Endo, Tokyo (JP); Hiroko Tanaka, Tokyo (JP); Doug Barnum, San Francisco, CA (US); Jonathan Greene, Palo Alto, CA (US); Wilna Moree, San Diego, CA (US); Michele Ramirez Weinhouse, Escondido, CA (US); Christine M. Tarby, Cardiff, CA (US)

(73) Assignees: Teijin Intellectual Property Center Limited, Osaka (JP); Combichem, Inc., CA (US)

( * ) Notice: Subject to any disclaimer, the term of this patent is extended or adjusted under 35 U.S.C. 154(b) by 0 days.

(21) Appl. No.: 09/180,994

(22) PCT Filed: May 20, 1997

(86) PCT No.: PCT/US97/08577

§ 371 (c)(1),
(2), (4) Date: Jul. 15, 1999

(87) PCT Pub. No.: WO97/44329

PCT Pub. Date: Nov. 27, 1997

Related U.S. Application Data

(63) Continuation-in-part of application No. 08/858,238, filed on May 19, 1997, now abandoned.

(30) Foreign Application Priority Data

May 20, 1996 (JP) .............................................. 8-147846

(51) Int. Cl.⁷ ....................... A61K 31/55; A61K 31/495; A61K 31/50; C07D 243/08; A61P 19/00

(52) U.S. Cl. ............. 514/218; 514/252.13; 514/255.04; 514/253.01; 540/575; 544/359; 544/398; 544/403; 544/360; 544/379; 544/396

(58) Field of Search ........................... 540/575; 544/359, 544/398, 403; 514/218, 255.04, 252.13

(56) References Cited

U.S. PATENT DOCUMENTS

| | | | | |
|---|---|---|---|---|
| 5,028,610 A | * | 7/1991 | Hirai et al. | ................... 514/259 |
| 5,432,179 A | * | 7/1995 | Kumagai et al. | ............ 514/255 |
| 5,716,950 A | * | 2/1998 | Kashima et al. | ............. 514/218 |

FOREIGN PATENT DOCUMENTS

| | | | | |
|---|---|---|---|---|
| EP | 0 166 302 | | 1/1986 | ......... C07D/243/08 |
| WO | WO 90/03371 | | 4/1990 | ....... C07D/295/084 |
| WO | WO 96/25157 | | 8/1996 | ........... A61K/31/17 |

OTHER PUBLICATIONS

CAPLUS printout for JP 50029578, Mar. 25, 1975.*
CAPLUS printout for JP 49093379, Sep. 1974.*

* cited by examiner

*Primary Examiner*—Brenda Coleman
(74) *Attorney, Agent, or Firm*—Anderson Kill & Olick; Eugene Lieberstein; Michael N. Meller

(57) ABSTRACT

Cyclic diamines of formula (I) or their pharmacologically acceptable acid addition salts, and their medical applications are described. These compounds inhibit the action of chemokines such as MIP-1a and/or MCP-1 on target cells, and are useful as a therapeutic drug and/or preventative drug in diseases, such as atherosclerosis, rheumatoid arthritis, and the like where blood monocytes and lymphocytes infiltrate into tissue.

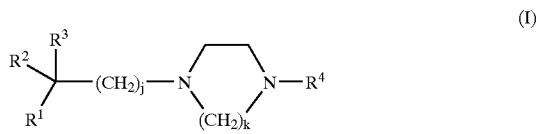

(I)

18 Claims, No Drawings

DIARYLALKYL CYCLIC DIAMINE DERIVATIVES AS CHEMOKINE RECEPTOR ANTAGONISTS

This application is a national stage entry under 35 USC §371 of PCT/US97/08577 filed May 20, 1997 which is a continuation-in-part of application Ser. No. 08/858,238 filed May 19, 1997, now abandoned.

TECHNICAL FIELD

This invention relates to novel diarylalkyl cyclic diamine derivatives.

This invention also relates to chemokine receptor antagonists that may be effective as a therapeutic agent and/or preventive agent for diseases such as atherosclerosis, rheumatoid arthritis, psoriasis, asthma, ulcerative colitis, glomerulonephritis, multiple sclerosis, pulmonary fibrosis, and myocarditis, in which tissue infiltration of blood monocytes and lymphocytes plays a major role in the initiation, progression or maintenance of the disease.

BACKGROUND TECHNOLOGY

Chemokines are a group of inflammatory/immunomodulatory polypeptide factors produced by lymphatic tissues and by activated macrophages and leukocytes at inflammatory sites; they have a molecular weight of 6–15 kD, contain four cysteine residues, are basic and have heparin binding activity. The chemokines can be classified into two subfamilies, the CXC chemokines and CC chemokines, by the common location of the four cysteine residues and by the differences in the chromosomal locations of the genes encoding them. For example IL-8 (abbreviation for interleukin-8 is a CXC chemokine, while the CC chemokines include MIP-1α/β (abbreviation for macrophage inflammatory protein-1α/β), MCP-1 (abbreviation for monocyte chemotactic protein-1), and RANTES (abbreviation for regulated on activation, normal T-cell expressed and secreted cytokine). There also exists a chemokine called lymphotactin, which does not fall into either chemokine subfamily. These chemokines promote cell migration, increase the expression of cellular adhesion molecules such as integrins, and promote cellular adhesion, and are thought to be the protein factors intimately involved in the adhesion and infiltration of leukocytes into the pathogenic sites in such as inflammatory tissues (for references, see for example, Michiel, D., Biotechnology, 1993, 11, 739; Oppenheim, J. J., et al., Annual Review of Immuology, 1991, 9, 617–648; Schall, T. J., Cytokine, 1991, 3, 165–183; Springer, T. A., Cell, 1994, 76, 301–314; Furie, M. B., American Journal of Pathology, 1995, 146, 1287–1301; Kelner, G. S., et al.; Science, 1994, 266, 1395–1399).

For example, HIP-1α induces cell migration and causes a transient increase in intracellular calcium ion concentration levels, an increase in the expression of integrins, adhesion molecules, and degranulation of monocytes and lymphocytes, and inhibits bone marrow stem cell proliferation (See for example, Wolpe, S. D., et al., Journal of Experimental Medicine, 1998, 167, 570–581; Wolpe, S. D., et al., Faseb Journal, 1989, 3, 2565–2573; Taub, D. D., at al., Science, 1993, 260, 355–358; Schall. T. J., at al., Journal of Experimental Medicine, 1993, 177, 1821–1825; Neote, K., et al., Cell, 1993, 72, 415–425; Vaddi, K., et al., The Journal of Immunology, 1994, 153, 4721–4732).

With respect to the activity of HIP-1α in vivo and its role in the pathogenesis of disease, it has been reported that it is a pyrogen in rabbits (see for example Davatelis, G., et al., Science, 1989, 243, 1066–1068); that MIP-1α injection into mouse foot pads results in an inflammatory reaction such as infiltration by neutrophils and mononuclear cells (see for example Alam, R., et al., The Journal of Immunology, 1994, 152, 1298–1303); that MIP-1α neutralizing antibody has an inhibitory effect or a therapeutic affect in animal models of granuloma, multiple sclerosis and idiopathic pulmonary fibrosis (see for example Lukacs, N. W., et al., Journal of Experimental Medicine, 1993, 177, 1551–1559; Koprus, K. J., et al., The Journal of Immunology, 1995, 155, 5003–5010; Smith, R. E., et al., The Journal of Immunology, 1994, 153, 4704–4712); and that coxsackie virus induced myocarditis is inhibited in mice with a disrupted MIP-1α gene (see for example Cook, D. N. et al., Science, 1995, 269, 1583–1585). These studies indicate that MIP-1α is deeply involved in the local attraction of various subtypes of leukocytes and the initiation, progression and maintenance of resulting inflammatory response.

MCP-1 (also known as MCAF (abbreviation for macrophage chemotactic and activating factor) or JE) is a chemokine produced by macrophages, smooth muscle cells, fibroblasts, and vascular endothelial cells and causes cell migration and cell adhesion of monocytes, memory T cells, and natural killer cells, as well as mediating histamine release by basophils (For reference, see for example, Rollins, B. J., et al., Proc. Natl. Acad. Sci. USA, 1988, 85, 3738–3742; Matsushima, K., at al., Journal of Experimental Medicine, 1989, 169, 1485–14907; Yoshimura, T. et al., Febs Letters, 1989, 244, 487–493; Rollins, B. J. et al., Blood, 1991, 78, 1112–1116; Carr, M. W., at al., Proc. Natl. Acad. Sci. USA, 1994, 91, 3652–3656; Jiang, Y., et al., American Journal of Physiology, 1994, 267, C1112–C1118; Allavena, P., et al., European Journal of Immunology, 1994, 24, 3233–3236; Alam, R., et al., The Journal of Clinical Investigation, 1992, 89, 723–728).

In addition, high expression of MCP-1 has been reported in diseases where accumulation of monocyte/macrophage and/or T cells is thought to be important in the initiation or progression of diseases, such as atherosclerosis, restenosis due to endothelial injury following angioplasty, rheumatoid arthritis, glomerulonephritis, pulmonary fibrosis, asthma and psoriasis (for reference, see for example, Firestein, G. S. et al., Arthritis and Rheumatism, 1990, 33, 768–773; Nikolic-Peterson, D. J., et al., Kidney International, 1994, 45, enlarged ed., 45, S79–S82; Thomas, P. D., et al., American Review of Respiratory Disease, 1987, 135, 747–760; Ross, R., Nature, 1993, 362, 801–809; Cooper, K. D., et al., The Journal of Investigative Dermatology, 1994, 102, 128–137; Sousa, A. R., et al., American Journal of Respiratory Cell And Molecular Biology, 1994). Furthermore, anti-MCP-1 antibody has been reported to inhibit delayed type hypersensitivity and hepatitis (for reference, see for example Rand, M. L., et al., American Journal of Pathology, 1996, 148, 855–864; Wada, T., et al., Faseb Journal, 1996, 10, 1418–1425).

These data indicate that chemokines such as MIP-1α and MCP-1 attract monocytes and lymphocytes to disease sites and mediate their activation and thus are thought to be intimately involved in the initiation, progression and maintenance of diseases deeply involving monocytes and lymphocytes, such as atherosclerosis, rheumatoid arthritis, psoriasis, asthma, ulcerative colitis, glomerulonephritis, multiple sclerosis, pulmonary fibrosis and myocarditis.

Therefore, drugs which inhibit the action of chemokines on target cells may be effective as a therapeutic and/or preventive drug in diseases such as atherosclerosis, rheumatoid arthritis, psoriasis, asthma, ulcerative colitis, glomerulonephritis, multiple sclerosis, pulmonary fibrosis, and myocarditis.

Genes encoding receptors of specific chemokines have been cloned, and it is now known that these receptors are G protein-coupled seven-transmembrane receptors present on various leukocyte populations (for reference, see for example, Holmes, W. E., et al., Science 1991, 253, 1278–1280; Murphy P. M., et al., Science, 253, 1280–1283; Neote, K. et al., Cell, 1993, 72, 415–425; Charo, I. F., et al., Proc. Natl. Acad. Sci. USA, 1994, 91, 2752–2756; Yamagami, S., et al., Biochem. Biophys. Res. Commun., 1994, 202, 1156–1162; Combadier, C., et al., The Journal of Biological Chemistry, 1995, 270, 16491–16494, Power, C. A., et al., J. Biol. Chem., 1995, 270, 19495–19500; Samson, H., et al., Biochemistry, 1996, 35, 3362–3367; Murphy, P. M., Annual Review of Immunology, 1994, 12, 592–633). Therefore, compounds which inhibit the binding of chemokines such as MIP-1α and/or MCP-1 to these receptors, that is, chemokine receptor antagonists, may be useful as drugs which inhibit the action of chemokines such as MIP-1α and/or MCP-1 on the target cells, but there are no drugs known to have such effects.

Cyclic diamine derivatives containing diarylalkyl groups are known to have muscarine receptor antagonistic activity (JP09-020758, Kokai) and may be useful as a drug in the treatment of substance abuse disorders (WO9320821), may potentiate the effect of anti-cancer drugs by the inhibition of P-glycoproteins (JP03-101662, Kokai; EP363212), has calcium antagonistic activity ((a) DE3831993, (b) WO9013539, (c) JP63-280081, Kokai; EP289227, (d) JP62-167762, Kokai; DE3600390), have activity on the central nervous system and inhibits hypermotility (WO8807528), have antiaggression, antipsychotic, antidepressant and, analgesic effect (JP57-500828, Kokai), has coronary vasodilating activity (JP51-098281, Kokai), has anti-lipidemia effect and promotes vascular blood flow (JP49-093379, Kokai; EP42366), have coronary vasodilating activity and anti-reserpine activity (Aritomi, J., et al., Yakugaku Zasshi, 1971, 91, 972–979); have anti-serotonin and anti-histamine activity (JP45-031193, Kokoku); and have central nervous system depressant activity (Vadodaria, D. J., et al., J. Med. Chem., 1969, 12, 860–865). However, these compounds differ from the novel compounds of the present invention and these compounds have not been known to interfere with binding of chemokines to the target cells.

DISCLOSURE OF THE INVENTION

Therefore, it is an object of the present invention to discover small molecule drugs which inhibit the binding of chemokines such as MIP-1α and/or MCP-1 to their receptors on the target cells.

It is another object of the present invention to establish a method to inhibit the binding to the receptors on the target cells and/or effects on target cells of chemokines such as MIP-1α and/or MCP-1.

It is an additional object of the present invention to propose a method for the treatment of diseases for which the binding of chemokines such as MIP-1α and/or MCP-1 to the receptor on the target cell is one of the causes.

As a result of their intensive studies, the present inventors discovered that a cyclic diamine derivative having a diarylalkyl group or its pharmacologically acceptable acid adduct has an excellent activity to inhibit the binding of chemokines such as MIP-1α and/or MCP-1 and the like to the receptor of a target cell, which has led to the completion of this invention.

That is, the present invention provides a cyclic diamine derivative or its pharmacologically acceptable acid adduct (Invention 1), represented by the formula [I] below:

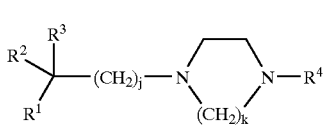

[wherein $R^1$ and $R^2$ are identical to or different from each other representing a phenyl group or an aromatic heterocyclic group having 1–3 heteroatoms, selected from oxygen atoms, sulfur atoms, and/or nitrogen atoms, in which the phenyl or aromatic heterocyclic group may be substituted by any number of halogen atoms, hydroxy groups, $C_1$–$C_8$ lower alkyl groups, $C_1$–$C_6$ lower alkoxy groups, phenyl groups, benzyl groups, phenoxy groups, methylenedioxy groups, $C_1$–$C_6$ hydroxyalkyl groups, carboxy groups, $C_2$–$C_7$ alkoxycarbonyl groups, $C_2$–$C_7$ alkanoylamino groups, dioxolanyl groups, or by group represented by the formula: —$NR^5R^6$, or else may be condensed with a benzene ring to form a condensed ring, furthermore above substituents for the phenyl or aromatic heterocyclic group and the condensed ring condensed with a benzene ring are optionally substituted by any substituents independently selected from halogen atoms, hydroxy groups, or $C_1$–$C_6$ lower alkoxy groups, and $R^5$ and $R^6$ may be identical to or different from each other representing hydrogen atoms, $C_1$–$C_6$ lower alkyl groups , or $C_2$–$C_6$ lower alkenyl groups;

$R^3$ represents a hydrogen atom, hydroxy group, cyano group, $C_1$–$C_6$ lower alkoxy group or $C_2$–$C_7$ lower alkanoyloxy group;

j represents an integer of 0–3;

k represents 2 or 3;

$R^4$ is a group represented by:

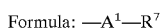

Formula: —$A^1$—$R^7$        1)

(in the formula, $R^7$ represents a phenyl group which may be substituted by any number of the same or different {halogen atoms, hyroxy groups, amino groups, $C_1$–$C_6$ lower alkyl groups, $C_1$–$C_6$ lower alkoxy groups, cyano groups, nitro groups, trifluoromethyl groups, $C_2$–$C_7$ alkoxycarbonyl groups, $C_2$–$C_7$ alkanoyl groups, $C_1$–$C_6$ alkylsulfonyl groups, trifluoromethylsulfonyl groups, phenylsulfonyl groups (which may be substituted with a hydroxy group}, 1-pyrrolylsulfonyl groups, $C_1$–$C_6$ hydroxyalkylsulfonyl groups, $C_1$–$C_6$ alkanoylamino groups, or a group represented by the formula: —$CONR^8R^9$) in which $R^8$ and $R^9$, identical to or different from each other, represent hydrogen atoms or $C_1$–$C_6$ lower alkyl groups; $A^1$ is a group represented by the formula: —$(CH_2)_m$— or a group represented by formula: —$(CH_2)_p$—G—$(CH_2)_q$— in which G represents $G_1$ or $G_2$; $G^1$ represents —O—, —CO—, —$SO_2$—, —CO—O—, —CONH—, —NHCO—, —NHCONH—, or —NH—$SO_2$—; $G^2$ represents —(C=NH)NH—$SO_2$—, —CO—NH—NH—CO—, —CO—NH—NH—CO—$NR^{10}$—, —CO—NH—$CH_2$—CO—, —CO—NH—NH—$SO_2$—, or —CO—N($CH_2$—CO—$OCH_3$)—NH—CO—; $R^{10}$ represents a hydrogen atom or a phenyl group; m is an integer of 0–3; p is an integer of 1–3; q represents 0 or 1):

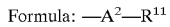

Formula: —$A^2$—$R^{11}$        2)

(wherein $A^2$ represents —CO— or —$SO_2$—; $R^{11}$ represents:
   a) A phenyl group which may be substituted by any number of the same or different (halogen atoms, $C_1$–$C_6$ lower alkyl groups, $C_1$–$C_6$ lower alkoxy groups, groups represented by formula —$CH_2$—$NR^{12}R^{13}$ or groups represented by the formula:

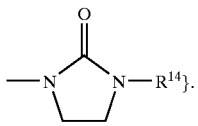

b) An aromatic monocyclic heterocyclic group having 1–3 heteroatoms, selected from oxygen atoms, sulfur atoms, and/or nitrogen atoms, and optionally substituted with any of the same or different number of (halogen atoms, $C_1$–$C_6$ lower alkyl groups, $C_1$–$C_6$ lower alkoxy groups), or c) A group represented by the formula: —$CH_2$—$NR^{15}R^{16}$, where $R^{12}$, $R^{13}$, $R^{14}$ and $R^{15}$, identical or different groups, represent hydrogen atoms or $C_1$–$C_6$ lower alkyl groups and $R^{16}$ represents (a phenyl group or a phenylalkyl group), which may be substituted by any number of the same or different halogen atoms, $C_1$–$C_6$ lower alkyl group, or $C_1$–$C_6$ lower alkoxy group);

Formula: —$(CH_2)_n$—$R^{17}$      3)

(in the formula, $R^{17}$ is a group which may be substituted at any possible sites by any number of the same or different (halogen atoms, hydroxy groups, $C_1$–$C_6$ lower alkyl groups, or $C_1$–$C_6$ lower alkoxy group s), representing a hydrogen atom, cyano group, $C_2$–$C_7$ alkoxycarbonyl group, $C_1$–$C_6$ hydroxyalkyl group, $C_1$–$C_6$ lower alkynyl group, $C_3$–$C_6$ cycloalkyl group, $C_3$–$C_7$ alkenoyl group, a group represented by the formula: —(CHOH)$CH_2OR^{18}$, a group represented by the formula: —CO—NH—NH—CO—$OR^{19}$, a group represented by the formula:

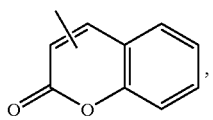

a group represented by the formula:

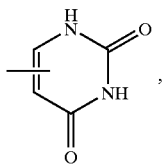

a group represented by the formula:

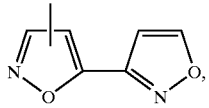

a group represented by the formula:

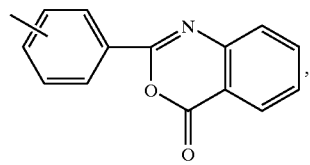

a group represented by the formula:

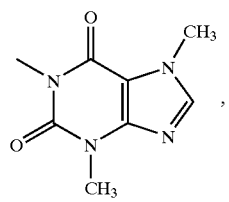

a group represented by the formula:

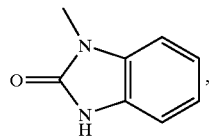

a group represented by the formula:

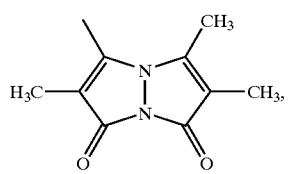

a group represented by the formula:

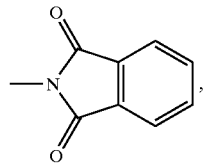

a group represented by the formula:

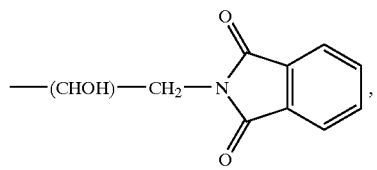

a group represented by the formula:

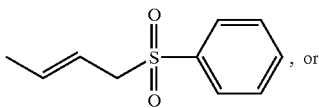, or a group represented by the formula:

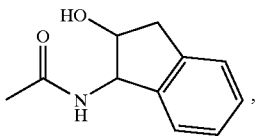, in which n represents an integer of 1–4; $R^{18}$ is $C_1$–$C_6$ lower alkyl group, $C_2$–$C_6$ lower alkenyl group, or $C_2$–$C_6$ lower alkynyl group and $R^{19}$ represents a $C_1$–$C_6$ lower alkyl group);

Formula: —$(CH_2)_r$—$A^3$—$R^{20}$  4)

(wherein r represents an integer of 0–3; $A^3$ represents a single bond, —CO—, —CO—NH—NH—CO—, —CO—NH—NH—CO—NH—, —CO—NH—$CH_2$—CO—, —CO—NH—NH—$SO_2$—, —(CHOH)—$CH_2$—, or —(CHOH)—$CH_2OCH_2$—; $R^{20}$ represents an aromatic heterocyclic group containing 1–3 heteroatoms, selected from oxygen atoms, sulfur atoms, and/or nitrogen atoms in which the aromatic heterocyclic group may be substituted by any number of the same or different (halogen atoms, $C_1$–$C_6$ lower alkyl groups, $C_1$–$C_6$ lower alkoxy groups, or pyrrolyl groups) or may be condensed with a benzene ring to form a condensed ring); or Formula: —$CH_2$—CO—$NR^{21}R^{22}$  5)

(wherein $R^{21}$ represents a hydrogen atom or $C_1$–$C_6$ lower alkyl group; $R^{22}$ represents a hydrogen atom, $C_1$–$C_6$ lower alkyl group, a group represented by the formula:

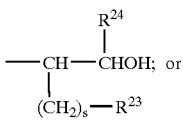

a group represented by the formula:

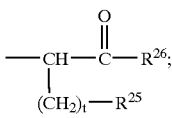

or $R^{21}$ and $R^{22}$ may be taken together with the nitrogen to form a 4 to 7-membered saturated heterocycles, which may contain an oxygen atom, sulfur atom, or another nitrogen atom; where s represents 0 or 1; t represents an integer of 0–2; $R^{23}$ represents a hydrogen atom, hydroxy group, phenyl group, $C_1$–$C_6$ lower alkyl group, or $C_1$–$C_6$ lower alkoxy group; $R^{24}$ represents a hydrogen atom or phenyl group which may be substituted by hydroxy group; $R^{25}$ represents a hydrogen atom, phenyl group (which may be substituted by hydroxy group), $C_2$–$C_7$ alkoxycarbonyl group, $C_1$–$C_6$ lower alkyl group, $C_1$–$C_6$ alkylthio group, or 3-indolyl group; and $R^{26}$ represents a hydroxy group, amino group, $C_1$–$C_6$ lower alkoxy group, or phenylalkyloxy group);

Excepting that if $R^3$ is a hydrogen atom, then, j is not 0, substituent for $R^7$ is not hydroxy, $C_1$–$C_6$ lower alkyl or $C_1$–$C_6$ lower alkoxy; $G^1$ is not —O— or —CO—; its substituents, if $R^{11}$ is a phenyl group, are not $C_1$–$C_6$ lower alkyl group; $R^{17}$ is not a hydrogen atom, $C^2$–$C_7$ alkoxycarbonyl group, or $C_1$–$C_6$ hydroxyalkyl group; r is not 0 and $A^3$ is not a single bond or —CO—.

Furthermore, if $R^3$ represents a hydrogen atom and k represents 2, $R^7$ is not unsubstituted; m is not 0 and $R^{11}$ is not a substituted or unsubstituted phenyl group.

If $R^3$ is a cyano group, $R^7$ is not unsubstituted, and the substituent groups for $R^7$ are not halogen atom, $C_1$–$C_6$ lower alkyl group or $C_1$–$C_6$ lower alkoxy group.]

The present invention provides a method of inhibiting the binding of chemokines to the receptor of a target cell and/or a method to inhibit its action onto a target cell using a pharmacological formulation containing as an active ingredient, a cyclic diamine derivative or its pharmacologically acceptable acid adduct (Invention 2) represented by the formula [II] below:

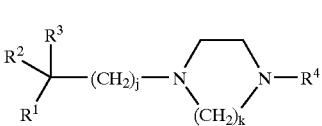

[II]

(wherein $R^1$ and $R^2$ are identical to or different from each other representing a phenyl group or an aromatic heterocyclic group having 1–3 heteroatoms, selected from oxygen atoms, sulfur atoms, and/or nitrogen atoms, in which the phenyl or aromatic heterocyclic group may be substituted by any number of halogen atoms, hydroxy groups, $C_1$–$C_8$ lower alkyl groups, $C_1$–$C_6$ lower alkoxy groups, phenyl groups, benzyl groups, phenoxy groups, methylenedioxy groups, $C_1$–$C_6$ hydroxyalkyl groups, carboxy groups, $C_2$–$C_7$ alkoxycarbonyl groups, $C_2$–$C_7$ alkanoylamino groups, dioxolanyl groups, or by group represented by the formula: —$NR^5R^6$, or else may be condensed with a benzene ring to form a condensed ring, furthermore above substituents for the phenyl or aromatic heterocyclic group and the condensed ring condensed with a benzene ring are optionally substituted by any substituents independently selected from halogen atoms, hydroxy groups, or $C_1$–$C_6$ lower alkoxy groups, and $R^5$ and $R^6$ may be identical to or different from each other representing hydrogen atoms, $C_1$–$C_6$ lower alkyl groups, or $C_2$–$C_6$ lower alkenyl groups;

$R^3$ represents a hydrogen atom, hydroxy group, cyano group, $C_1$–$C_6$ lower alkoxy group or $C_2$–$C_7$ lower alkanoyloxy group;

j represents an integer of 0–3;

k represents 2 or 3;

$R^4$ is a group represented by:

Formula: —$A^1$—$R^7$  1)

(in the formula, $R^7$ represents a phenyl group which may be substituted by any number of the same or different {halogen atoms, hydroxy groups, amino groups, $C_1$–$C_6$ lower alkyl groups, $C_1$–$C_6$ lower alkoxy groups, cyano groups, nitro groups, trifluoromethyl groups, $C_2$–$C_7$ alkoxycarbonyl groups, $C_2$–$C_7$ alkanoyl groups, $C_1$–$C_6$ alkylsulfonyl groups, trifluoromethylsulfonyl groups, phenylsulfonyl groups (which may be substituted with a hydroxy group},
1-pyrrolylsulfonyl groups, $C_1$–$C_6$ hydroxyalkylsulfonyl
groups, $C_1$–$C_6$ alkanoylamino groups, or a group represented by the formula: —CONR$^8$R$^9$) in which R$^8$ and R$^9$,
identical to or different from each other, represent hydrogen
atoms or $C_1$–$C_6$ lower alkyl groups; A$^1$ is a group represented by the formula: —(CH$_2$)$_m$— or a group represented
by formula: —(CH$_2$)$_p$—G—(CH$_2$)$_q$— in which G represents G$^1$ or G$^2$; G$^1$ represents —O—, —CO—, —SO$_2$—,
—CO—O—, —CONH—, —NHCO—, —NHCONH—, or
—NH—SO$_2$—; G$^2$ represents —(C=NH)NH—SO$_2$—,
—CO—NH—NH—CO—, —CO—NH—NH—CO—
NR$^{10}$—, —CO—NH—CH$_2$—CO—, —CO—NH—NH—
SO$_2$—, or —CO—N(CH$_2$—CO—OCH$_3$)—NH—CO—;
R$^{10}$ represents a hydrogen atom or a phenyl group; m is an
integer of 0–3; p is an integer of 1–3; q represents 0 or 1):

Formula: —A$^2$—R$^{11}$  2)

(wherein A$^2$ represents —CO— or —SO$_2$—; R$^{11}$ represents:

a) A phenyl group which may be substituted by any
number of the same or different (halogen atoms, $C_1$–$C_6$
lower alkyl groups, $C_1$–$C_6$ lower alkoxy groups, groups
represented by formula —CH$_2$—NR$^{12}$R$^{13}$ or groups
represented by the formula:

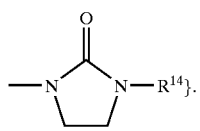

b) An aromatic monocyclic heterocyclic group having 1–3
heteroatoms, selected from oxygen atoms, sulfur
atoms, and/or nitrogen atoms, and optionally substituted with any of the same or different number of
(halogen atoms, $C_1$–$C_6$ lower alkyl groups, $C_1$–$C_6$
lower alkoxy groups), or c) A group represented by the formula: —CH$_2$—
NR$^{15}$R$^{16}$,
where R$^{12}$, R$^{13}$, R$^{14}$ and R$^{15}$, identical or different
groups, represent hydrogen atoms or $C_1$–$C_6$ lower
alkyl groups and R$^{16}$ represents (a phenyl group or a
phenylalkyl group), which may be substituted by any
number of the same or different halogen atoms,
$C_1$–$C_6$ lower alkyl group, or $C_1$–$C_6$ lower alkoxy
group):

Formula: —(CH$_2$)$_n$—R$^{17}$  3)

(in the formula, R$^{17}$ is a group which may be substituted at
any possible sites by any number of the same or different
(halogen atoms, hydroxy groups, $C_1$–$C_6$ lower alkyl groups,
or $C_1$–$C_6$ lower alkoxy groups), representing a hydrogen atom, cyano group, $C_2$–$C_7$ alkoxycarbonyl
group, $C_1$–$C_6$ hydroxyalkyl group, $C_1$–$C_6$ lower alkynyl group, $C_3$–$C_6$ cycloalkyl group, $C_3$–$C_7$ alkenoyl
group, a group represented by the formula: —(CHOH)
CH$_2$OR$^{18}$, a group represented by the formula:
—CO—NH—NH—CO—OR$^{19}$, a group represented
by the formula:

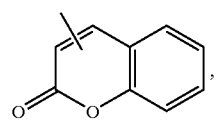

a group represented by the formula:

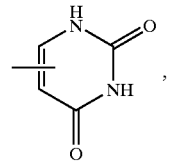

a group represented by the formula:

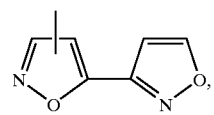

a group represented by the formula:

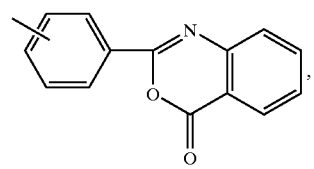

a group represented by the formula:

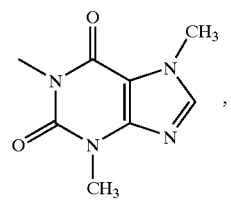

a group represented by the formula:

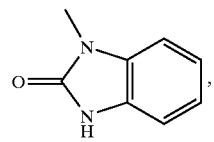

a group represented by the formula:

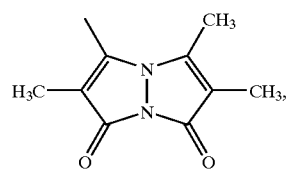

a group represented by the formula:

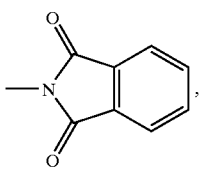

a group represented by the formula:

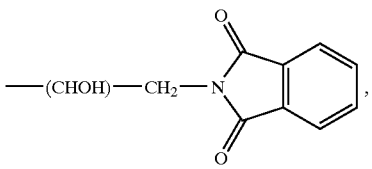

a group represented by the formula:

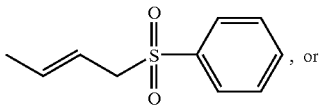

a group represented by the formula:

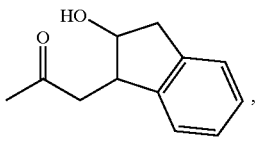

in which n represents an integer of 1–4; $R^{18}$ is $C_1$–$C_6$ lower alkyl group, $C_2$–$C_6$ lower alkenyl group, or $C_2$–$C_6$ lower alkynyl group and $R^{19}$ represents a $C_1$–$C_6$ lower alkyl group):

Formula: —$(CH_2)_r$—$A^3$—$R^{20}$      4)

(wherein r represents an integer of 0–3; $A^3$ represents a single bond, —CO—, —CO—NH—NH—CO—, —CO—NH—NH—CO—NH—, —CO—NH—$CH_2$—CO—, —CO—NH—NH—$SO_2$—, —(CHOH)—$CH_2$—, or —(CHOH)—$CH_2OCH_2$—; $R^{20}$ represents an aromatic heterocyclic group containing 1–3 heteroatoms, selected from oxygen atoms, sulfur atoms, and/or nitrogen atoms in which the aromatic heterocyclic group may be substituted by any number of the same or different (halogen atoms, $C_1$–$C_6$ lower alkyl groups, $C_1$–$C_6$ lower alkoxy groups, or pyrrolyl groups) or may be condensed with a benzene ring to form a condensed ring):

Formula: —$CH_2$—CO—$NR^{21}R^{22}$      5)

(wherein $R^{21}$ represents a hydrogen atom or $C_1$–$C_6$ lower alkyl group; $R^{22}$ represents a hydrogen atom, $C_1$–$C_6$ lower alkyl group, a group represented by the formula:

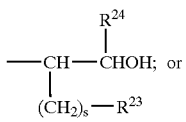

a group represented by the formula:

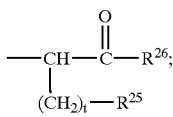

or $R^{21}$ and $R^{22}$ may be taken together with the nitrogen to form a 4 to 7-membered saturated heterocycles, which may contain an oxygen atom, sulfur atom, or another nitrogen atom; where s represents 0 or 1; t represents an integer of 0–2; $R^{23}$ represents a hydrogen atom, hydroxy group, phenyl group, $C_1$–$C_6$ lower alkyl group, or $C_1$–$C_6$ lower alkoxy group; $R^{24}$ represents a hydrogen atom or phenyl group which may be substituted by hydroxy group; $R^{25}$ represents a hydrogen atom, phenyl group (which may be substituted by hydroxy group), $C_2$–$C_7$ alkoxycarbonyl group, $C_1$–$C_6$ lower alkyl group, $C_1$–$C_6$ alkylthio group, or 3-indolyl group; and $R^{26}$ represents a hydroxy group, amino group, $C_1$–$C_6$ lower alkoxy group, or phenylalkyloxy group):

A hydrogen atom, $C_1$–$C_6$ alkanoyl group, or $C_2$–$C_7$ alkoxycarbonyl group.]

Here, the compounds represented by the above formula [II] have activities to inhibit the binding of chemokines such as MIP-1α and/or MCP-1 and the like to the receptor of a target cell and activities to inhibit physiological activities of cells caused by chemokines such as MIP-1α and/or MCP-1 and the lie.

PREFERRED EMBODIMENTS OF THE INVENTION (1) On Invention 1

In the above formula [I], $R^1$ and $R^2$ are identical to or different from each other representing a phenyl group or an aromatic heterocyclic group having 1–3 heteroatoms, selected from oxygen atoms, sulfur atoms, and/or nitrogen atoms, in which the phenyl or aromatic heterocyclic group may be substituted by any number of halogen atoms, hydroxy groups, $C_1$–$C_6$ lower alkyl groups, $C_1$–$C_6$ lower alkoxy groups, phenyl groups, benzyl groups, phenoxy groups, methylenedioxy groups, $C_1$–$C_6$ hydroxyalkyl groups, carboxy groups, $C_2$–$C_7$ alkoxycarbonyl groups, $C_1$–$C_6$ alkanoylamino groups, dioxolanyl groups, or by group represented by the formula: —$NR^5R^6$, or else may be condensed with a benzene ring to form a condensed ring. Unsubstituted aromatic heterocyclic groups having 1–3 heteroatoms, selected from oxygen atoms, sulfur atoms, and/or nitrogen atoms are specifically, for example, thienyl, furyl, pyrrolyl, imidazolyl, oxazolyl, isoxazolyl, thiazolyl, isothiazolyl, pyridyl, pyrinidinyl, triazinyl, triazolyl, oxadiazolyl, thiadiazolyl group and the like, preferably including thienyl, furyl, pyrrolyl, and pyridyl groups.

The halogen atom as substituents for a phenyl group or an aromatic heterocyclic group in $R^1$ and $R^2$ include fluorine atoms, chlorine atoms, bromine atoms, iodine atoms, suitably including fluorine atoms and chlorine atoms. The $C_1$–$C_8$ lower alkyl groups mean $C_1$–$C_8$ straight-chain or branched alkyl groups such as methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, isohexyl, 2-methylpentyl, 1-ethylbutyl, and the like, suitably specifically including, methyl, ethyl, and isopropyl groups. The $C_1$–$C_6$ lower alkoxy groups mean groups consisting of $C_1$–$C_6$ part of the aforementioned $C_1$–$C_8$ lower alkyl groups and oxy groups, specifically, for example, methoxy group and ethoxy group. The $C_1$–$C_6$ hydroxyalkyl groups are groups in which $C_1$–$C_6$ part of the aforementioned $C_1$–$C_8$ lower alkyl groups are substituted at their any positions by a hydroxy group, preferably and specifically for example, hydroxymethyl group, 2-hydroxyethyl group, and the like. The $C_2$–$C_7$ alkoxycarbonyl groups mean the aforementioned $C_1$–$C_6$ lower alkoxy groups and carbonyl groups, preferably specifically for example, a methoxycarbonyl group and ethoxycarbonyl group. The $C_2$–$C_7$ lower alkanoylamino groups mean $C_2$–$C_7$ lower straight-chain or branched alkanoylamino groups such as acetylamino, propanoylamino, butanoylamino, pentanoylamino, hexanoylamino, heptanoylamino, isobutyrylamino, 3-methylbutanoylamino, 2-methylbutanoylamino, pivaloylamino, 4-methylpentanoylamino, 3,3-dimethylbutanoylamino, 5-methylhexanoylamino group, and the like, where the preferred and specific example includes an acetylamino group. Condensed rings obtained by condensation with a benzene ring mean a ring obtained by the condensation with a benzene ring of a phenyl group or an aromatic monocyclic heterocyclic ring having 1–3 heteroatoms, selected from oxygen atoms, sulfur atoms, and/or nitrogen atoms, at any possible sites, suitably and specifically for example, naphthyl, indolyl, benzofuranyl, benzothienyl, quinolyl group, indolyl group, benzimidazolyl group.

$R^5$ and $R^6$ represent each independently hydrogen atoms, $C_1$–$C_6$ lower alkyl groups, or $C_2$–$C_6$ lower alkenyl groups. The $C_1$–$C_6$ lower alkyl groups are the same as defined for the aforementioned $C_1$–$C_6$ part of the $C_1$–$C_8$ lower alkyl groups as substituents for a phenyl group or an aromatic heterocyclic group in $R^1$ and $R^2$, where the same examples can be given for the preferred specific examples. The $C_2$–$C_6$ lower alkenyl groups are for example, $C_2$–$C_6$ straight-chain or branched alkenyl groups such as vinyl, allyl, 2-butenyl, 3-butenyl, 4-pentenyl, 5-hexenyl, 4-methyl-3-pentenyl, and the like, where preferred specific examples include allyl, 2-butenyl, and 3-butenyl group.

Furthermore above substituents for the phenyl or aromatic heterocyclic group and the condensed ring condenced with a benzene ring in $R^1$ and $R^2$ are optionally substituted by any substituents independently selected from halogen atoms, hydroxy groups, or $C_1$–$C_6$ lower alkoxy groups. The halogen atoms and $C_1$–$C_6$ lower alkoxy groups are the same as defined for the aforementioned substituents for a phenyl group or an aromatic heterocyclic group in $R^1$ and $R^2$, and the same examples can be listed as preferred specific examples.

$R^1$ in the above formula [I] represents a hydrogen atom, hydroxy group, cyano group, $C_1$–$C_6$ lower alkoxy group, or $C_2$–$C_7$ lower alkanoyloxy group. The $C_1$–$C_6$ lower alkoxy groups are the same as defined for the $C_1$–$C_6$ lower alkoxy groups in the aforementioned substituents for a phenyl group or an aromatic heterocyclic group in $R^1$ and $R^2$; where the same examples can be given for their preferred specific examples. The $C_2$–$C_7$ lower alkanoyloxy groups mean $C_2$–$C_7$ lower straight-chain or branched alkanoyloxy groups such as acetyloxy, propanoyloxy, butanoyloxy, pentanoyloxy, hexanoyloxy, heptanoyloxy, isobutyryloxy, 3-methylbutanoyloxy, 2-methylbutanoyloxy, pivaloyloxy, 4-methylpentanoyloxy, 3,3-dimethylbutanoyloxy, 5-methylhexanoyloxy group, and the like, where the preferred and specific example includes an acetyloxy group. Preferred specific examples for $R^3$ include a hydrogen atom and hydroxy group.

In the above formula [I], j represents an integer of 0–3. If $R^3$ represents a hydrogen atom, j is not 0. It is particularly preferred for j to be 2.

k in the above formula [I] represents 2 or 3; it is particularly preferred to use a homopiperazine derivative in which k is 3.

$R^4$ in the above formula [I] represents a group represented by:

Formula: $-A^1-R^7$,  1)

Formula: $-A^2-R^{11}$,  2)

Formula: $-(CH_2)_n-R^{17}$,  3)

Formula: $-(CH_2)_r-A^3-R^{20}$, or  4)

Formula: $-(CH_2)-CO-NR^{21}-R^{22}$.  5)

Here —CO— represents a carbonyl group. It is particularly preferred for $R^4$ to be represented by formula 1): $-A^1-R^7$ or formula 4): $-(CH_2)_r-A^3R^{20}$.

$R^7$ represents a phenyl group which may be substituted by any number of the same or different (halogen atoms, hydroxy groups, amino groups, $C_1$–$C_6$ lower alkyl groups, $C_1$–$C_6$ lower alkoxy groups, cyano groups, nitro groups, trifluoromethyl groups, $C_2$–$C_7$ alkoxycarbonyl groups, $C_2$–$C_7$ alkanoyl groups, $C_1$–$C_6$ alkylsulfonyl groups, trifluoromethylsulfonyl groups, phenylsulfonyl groups (which may be substituted with a hydroxy group), 1-pyrrolylsulfonyl groups, $C_1$–$C_6$ hydroxalkylsulfonyl groups, $C_1$–$C_6$ alkanoylamino groups, or a group represented by the formula: $-CONR^8R^9$). However, if $R^3$ represents a hydrogen atom, the substituent for a phenyl in $R^7$ is not a hydroxy, $C_1$–$C_6$ lower alkyl, or $C_1$–$C_6$ lower alkoxy; if $R^3$ is a hydrogen atom and k=2, $R^7$ is not an unsubstituted phenyl group; if $R^3$ represents a cyano group, $R^7$ is not unsubstituted and the substituent for a phenyl in $R^7$ is not a halogen atom, $C_1$–$C_6$ lower alkyl, or $C_1$–$C_6$ lower alkoxy group.

The halogen atoms, $C_1$–$C_6$ lower alkyl groups, $C_1$–$C_6$ lower alkoxy groups, $C_2$–$C_7$ alkoxycarbonyl groups, and $C_2$–$C_7$ alkanoylamino groups as substituents for a phenyl in $R^7$ are the same as defined for the aforementioned substituents for a phenyl group or an aromatic heterocyclic group in $R^1$ and $R^2$, and the same examples can be listed as preferred specific examples. The $C_2$–$C_7$ lower alkanoyl groups mean $C_2$–$C_7$ lower straight-chain or branched alkanoyl groups such as acetyl, propanoyl, butanoyl, pentanoyl, hexanoyl, heptanoyl, isobutyryl, 3-methylbutanoyl, 2-methylbutanoyl, pivaloyl, 4-methylpentanoyl, 3,3-dimethylbutanoyl, 5-methylhexanoyl group, and the like, where the preferred and specific example includes an acetyl group. The $C_1$–$C_6$ alkylsulfonyl groups mean those consisting of the aforementioned $C_1$–$C_6$ part of the $C_1$–$C_6$ lower alkyl groups and sulfonyl groups, preferably and specifically, for example, a methylsulfonyl group. The phenylsulfonyl groups may be substituted with a hydroxy group at any position. The $C_1$–$C_6$ hydroxyalkylsulfonyl groups mean those consisting of the aforementioned $C_1$–$C_6$ hydroxyallyl groups and sulfonyl groups, preferably and specifically, for example, a (2-hydroxyethyl) sulfonyl group. $R^8$ and $R^9$, the same or different groups, represent hydrogen atoms or $C_1$–$C_6$ lower alkyl groups. The $C_1$–$C_6$ lower alkyl groups as $R^8$ and $R^9$ are the same as defined for the aforementioned $C_1$–$C_6$ part of the $C_1$–$C_8$ lower alkyl groups as substituents for a phenyl group or an aromatic heterocyclic group in $R^1$ and $R^2$, and the same examples are listed for their preferred specific examples.

$A^1$ is a group represented by the formula: —$(CH_2)_m$— or a group represented by formula: —$(CH_2)_p$—G—$(CH_2)_q$— in which G represents $G^1$ or $G^2$; $G^1$ represents —O—, —CO—, —SO$_2$—, —CO—O—, —CONH—, —NHCO—, —NHCONH—, or —NH—SO$_2$—; $G^2$ represents —(C=NH)NH—SO$_2$—, —CO—NH—NH—CO—, —CO—NH—NH—CO—NR$^{10}$—, —CO—NH—CH$_2$—CO—, —CO—NH—NH—SO$_2$—, or —CO—N(CH$_2$—CO—OCH$_3$)—NH—CO—; $R^{10}$ represents a hydrogen atom or a phenyl group; m is an integer of 0–3; p is an integer of 1–3; q represents 0 or 1); however, if $R^3$ is a hydrogen atom, $G^1$ is not —O— or —CO—; if $R^3$ represents a hydrogen atom and if k=2, m is not 0. In the above formula, —CO— means a carbonyl group and —SO$_2$— means a sulfonyl group. Preferred $A^1$ groups are specifically, for example, those represented by the formula —$(CH_2)_m$—, with m being preferably 1. Preferred $A^1$ groups are also specifically, for example, —$(CH_2)_p$—CO—NH—NH—CO—$(CH_2)_q$—, —$(CH_2)_p$—CO—NH—NH—CO—NH—$(CH_2)_q$—; —$(CH_2)_p$—CO—NH—CH$_2$—CO—$(CH_2)_q$—; with p being preferably 1.

$A^2$ represents —CO— (carbonyl group) or —SO$_2$— (sulfonyl group).

$R^{11}$ represents:

a) A phenyl group which may be substituted by any number of the same or different (halogen atoms, $C_1$–$C_6$ lower alkyl groups, $C_1$–$C_6$ lower alkoxy groups, groups represented by formula —CH$_2$—NR$^{12}$R$^{13}$ or groups represented by the formula:

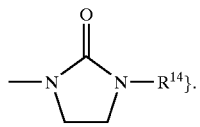

b) An aromatic monocyclic heterocyclic group having 1–3 heteroatoms, selected from oxygen atoms, sulfur atoms, and/or nitrogen atoms, and optionally substituted with any of the same or different number of (halogen atoms, $C_1$–$C_6$ lower alkyl groups, $C_1$–$C_6$ lower alkoxy groups), or c) A group represented by the formula: —CH$_2$—NR$^{15}$R$^{16}$.

However if $R^3$ represents a hydrogen atom, the substituent group for a phenyl group in $R^{11}$ is not a $C_1$–$C_6$ lower alkoxy group; if $R^3$ represents a hydrogen atom and k is 2, $R^{11}$ is not a substituted or unsubstituted phenyl group. The halogen atoms, $C_1$–$C_6$ lower alkyl groups, or $C_1$–$C_6$ lower alkoxy groups as substituents for the groups in $R^{11}$ are the same as defined for the aforementioned substituents for a phenyl group or an aromatic heterocyclic group in $R^1$ and $R^2$, and the same examples can be given as preferred specific examples.

Specific examples for $R^{11}$ in which the aromatic monocyclic heterocyclic group is unsubstituted can be the same specific examples for the aromatic heterocyclic groups with no substituents in $R^1$ and $R^2$. Preferred examples specifically include a pyridyl group.

$R^{12}$, $R^{13}$, $R^{14}$ and $R^{15}$ represent each independently hydrogen atoms or $C_1$–$C_6$ lower alkyl groups. The $C_1$–$C_6$ lower alkyl groups are of the same definition for the aforementioned $C_1$–$C_6$ part of the $C_1$–$C_8$ lower alkyl groups as substituents for a phenyl group or an aromatic heterocyclic group in $R^1$ and $R^2$, where the same examples can be listed as preferred specific examples.

$R^{16}$ represents a (phenyl group or phenylalkyl group) which may be substituted by any number of the same or different (halogen atoms, $C_1$–$C_6$ lower alkyl groups, or $C_1$–$C_6$ lower alkoxy group). The halogen atom, $C_1$–$C_6$ lower alkyl group or $C_1$–$C_6$ lower alkoxy group as substituents are the same as defined for the aforementioned substituents for a phenyl group or an aromatic heterocyclic group in $R^1$ and $R^2$, where the same examples can be given as preferred specific examples. The phenylalkyl group means a group consisting of a phenyl group and a $C_1$–$C_6$ alkylene group, preferably and specifically for example, a benzyl group.

$R^{17}$ is a group which may be substituted at any possible sites by any number of the same or different (halogen atoms, hydroxy groups, $C_1$–$C_6$ lower alkyl groups, or $C_1$–$C_6$ lower alkoxy groups), representing a hydrogen atom, cyano group, $C_2$–$C_7$ alkoxycarbonyl group, $C_1$–$C_6$ hydroxyalkyl group, $C_1$–$C_6$ lower alkynyl group, $C_3$–$C_6$ cycloalkyl group, $C_2$–$C_7$ alkenoyl group, a group represented by the formula: —(CHOH)CH$_2$OR$^{18}$, a group represented by the formula: —CO—NH—NH—CO—OR$^{19}$, a group represented by the formula:

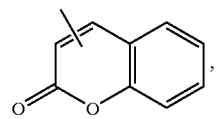

a group represented by the formula:

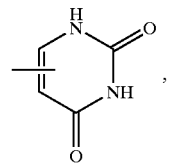

a group represented by the formula:

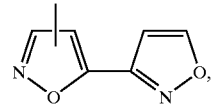

a group represented by the formula:

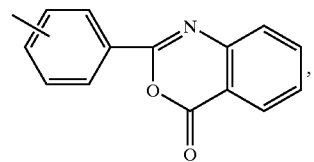

a group represented by the formula:

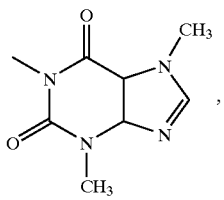

a group represented by the formula:

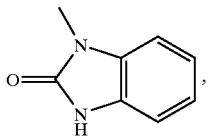

a group represented by the formula:

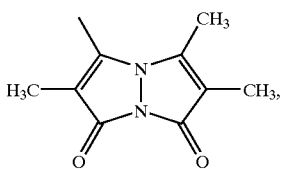

a group represented by the formula:

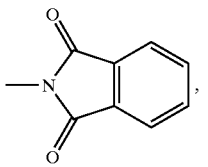

a group represented by the formula:

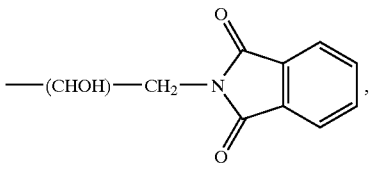

a group represented by the formula:

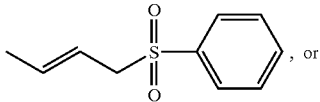, or a group represented by the formula:

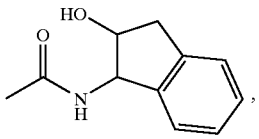

If, however, $R^3$ represents a hydrogen atom, $R^{17}$ is not a hydrogen atom, $C_2$–$C_7$ alkoxycarbonyl group, or $C_1$–$C_6$ hydroxyalkyl group. $R^{17}$ may be bonded at any possible site to an alkylene group —$(CH_2)_n$—. The $C_2$–$C_7$ alkoxycarbonyl and $C_1$–$C_6$ hydroxyalkyl groups are the same as defined for the aforementioned substituents for a phenyl group or an aromatic heterocyclic group in $R^1$ and $R^2$, where the same examples may be given as preferred specific examples. The $C_1$–$C_6$ lower alkynyl group means a $C_2$–$C_6$ straight-chain or branched alkynyl groups such as ethynyl, 1-propynyl, 2-propynyl, 2-butynyl, 3-butynyl, 4-pentynyl, 5-hexynyl, 1-methyl-4-pentynyl group, and the like, preferably and specifically, for example, ethynyl group and 1-propynyl group. The $C_3$–$C_6$ cycloalkyl groups mean cyclic alkyl groups such as cyclopropyl, cyclobutyl, cyclopentyl, cyclohexyl groups and the like. The $C_3$–$C_7$ lower alkenoyl group means a $C_3$–$C_7$ straight-chain or branched alkenoyl groups such as propenoyl, 2-metylpropenoyl, 2-buenoyl, 3-butenoyl, 2-methyl-3-butenoyl, 3-methyl-2-butenoyl, 2-pentenoyl, 4-pentenoyl, 2-methyl-2-pentenoyl, 2,2-dimethyl-4-pentenoyl, 2-hexenoyl, 3-hexenoyl, 6-heptenoyl, and the like, preferably and specifically, for example propenoyl and 2-metylpropenoyl group.

The halogen atom, $C_1$–$C_6$ lower alkyl group or $C_1$–$C_6$ lower alkoxy groups as substituents for $R^{17}$ are the same as defined for the aforementioned substituents for a phenyl group or an aromatic heterocyclic group in $R^1$ and $R^2$, and the same examples can be given as preferred specific examples.

$R^{18}$ represents a $C_1$–$C_6$ lower allkyl group, $C_2$–$C_6$ lower alkenyl group, or $C_2$–$C_6$ lower alkynyl group. The $C_1$–$C_6$ lower alkyl groups are the same as defined for the aforementioned $C_1$–$C_6$ part of the $C_1$–$C_6$ lower alkyl groups as substituents for a phenyl group or an aromatic heterocyclic group in $R^1$ and $R^2$, where the same examples can be given as preferred specific examples. The $C_2$–$C_6$ lower alkenyl groups are the same as the $C_2$–$C_6$ lower alkenyl groups in the aforementioned $R^5$ and $R^6$, where the preferred examples are specifically allyl, 2-butenyl, and 3-butenyl group. The $C_2$–$C_6$ lower alkynyl groups are the same as the $C_2$–$C_6$ lower alkynyl groups in the aforementioned $R^{17}$ where the preferred examples are specifically 2-propynyl group and 3-butynyl group.

$R^{19}$ represents a $C_1$–$C_6$ lower alkyl group. Here, the $C_1$–$C_6$ lower alkyl group is the same as defined for the aforementioned $C_1$–$C_6$ part of the $C_1$–$C_6$ lower alkyl groups as substituents for a phenyl group or an aromatic heterocyclic group in $R^1$ and $R^2$, where the same examples can be given as preferred specific examples.

n is an integer of 1–4. It is particularly preferred for the n to be 1 or 2.

$A^3$ represents a single bond, —CO—, —CO—NH—NH—CO—, —CO—NH—NH—CO—NH—, —CO—NH—CH$_2$—CO—, —CO—NH—NH—SO$_2$—, —(CHOH)—CH$_2$—, or —(CHOH)—CH$_2$OCH$_2$—. However, if $R^3$ represents a hydrogen atom. $A^3$ is not a single bond. Here, —CO— means a carbonyl group and —SO$_2$— means a sulfonyl group. $A^3$ is preferably a single bond or —CO—NH—NH—CO—.

$R^{20}$ represents an aromatic heterocyclic group containing 1–3 heteroatoms, selected from oxygen atoms, sulfur atoms, and/or nitrogen atoms in which the aromatic heterocyclic group may be substituted by any number of the same or different (halogen atoms, $C_1$–$C_6$ lower alkyl groups, $C_1$–$C_6$ lower alkoxy groups, or pyrrolyl groups) or may be condensed with a benzene ring to form a condensed ring. As to specific examples in which the aromatic monocyclic heterocyclic group $R^{20}$ has no substitution, the same specific example can be given as in the cases with no substituents on the aromatic heterocyclic rings in $R^1$ and $R^2$; preferred examples are specifically a pyridyl group and is oxazolyl group.

The halogen atom, $C_1$–$C_6$ lower alkyl group, or $C_1$–$C_6$ lower alkoxy group as substituents for the aromatic heterocyclic group in $R^{20}$ are the same as defined for the aforementioned substituents for a phenyl group or an aromatic heterocyclic group in $R^1$ and $R^2$, where the same examples can be given as suitable specific examples. The condensed ring obtained by condensation with a benzene ring in $R^{20}$ is the same as defined for the condenced ring in $R^1$ and $R^2$, where the same examples can be given as suitable specific examples.

r is an integer of 0–3. However, if $R^3$ represents a hydrogen atom, r is not 0. In particular, it is preferred for r to be 1.

$R^{21}$ represents a hydrogen atom or $C_1$–$C_6$ lower alkyl group. $R^{22}$ represents a hydrogen atom, $C_1$–$C_6$ lower alkyl group, a group represented by the formula:

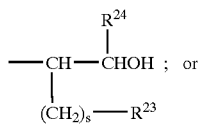

a group represented by the formula:

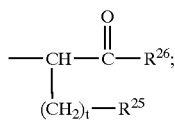

or may be taken together with the nitrogen to form a 4 to 7-membered saturated heterocycles, which may contain an oxygen atom, sulfur atom, or another nitrogen atom. The $C_1$–$C_6$ lower alkyl groups in $R^{21}$ and $R^{22}$ are the same as defined for the aforementioned $C_1$–$C_6$ part of the $C_1$–$C_8$ lower alkyl groups as substituents for a phenyl group or an aromatic heterocyclic group in $R^1$ and $R^2$, where the same examples can be given for the preferred specific examples. Saturated heterocyclic rings consisting of $R^{21}$, $R^{22}$, and the nitrogen include azetidine, pyrrolidine, piperidine, perhydroazepine, morpholine, thiamorpholine, piperazine, homopiperazine, and the like; preferred specific examples include piperidine, morpholine, and thiamorpholine.

s represents 0 or 1 and t represents an integer of 0–2.

$R^{23}$ represents a hydrogen atom, hydroxy group, phenyl group, $C_1$–$C_6$ lower alkyl group, or $C_1$–$C_6$ lower alkoxy group. The $C_1$–$C_6$ lower alkyl group and $C_1$–$C_6$ lower alkoxy groups as $R^{23}$ are the same as defined for the aforementioned substituents for a phenyl group or an aromatic heterocyclic group in $R^1$ and $R^2$, where the same examples can be given for the preferred specific examples.

$R^{24}$ represents a hydrogen atom or phenyl group, where the phenyl group may be substituted by hydroxy group at any position.

$R^{25}$ represents a hydrogen atom, phenyl group, $C_2$–$C_7$ alkoxycarbonyl group, $C_1$–$C_6$ lower alkyl group, $C_1$–$C_6$ alkylthio group, or 3-indolyl group, where the phenyl group may be substituted by hydroxy group at any position. The $C_2$–$C_7$ alkoxycarbonyl group and $C_1$–$C_6$ lower alkyl group as $R^{25}$ are the same as defined for the aforementioned substituents for a phenyl group or an aromatic heterocyclic group in $R^1$ and $R^2$, where the same examples can be given for the preferred specific examples. The $C_1$–$C_6$ alkylthio group as $R^{25}$ means a group consisting of thio group and $C_1$–$C_6$ part of the aforementioned $C_1$–$C_8$ lower alkyl groups for substituent in $R^1$ and $R^2$, specifically, for example, methylthio group and ethylthio group.

$R^{26}$ represents a hydroxy group, amino group, $C_1$–$C_6$ lower alkoxy group, or phenylalkyloxy group. The $C_1$–$C_6$ lower alkoxy group is the same as defined for the aforementioned $C_1$–$C_6$ lower alkoxy group as substituent for a phenyl group or an aromatic heterocyclic group in $R^1$ and $R^2$, where the same examples can be given for the preferred specific examples. The phenylalkyl group means a group consisting of a phenyl group, a $C_1$–$C_6$ alkylene group, and a oxy group, preferably and specifically for example, a benzyl oxy group.

(2) On Invention 2

$R^1$, $R^2$, $R^3$, j, and k in the above formula [II] are as the same as defined in the respective terms for the above formula [I] and the same examples can be listed for their preferred specific examples. $R^4$ in the above formula [II] includes $R^4$ defined in the respective terms for the above formula [I], where the same examples can be listed for their preferred specific examples, and furthermore $R^4$ in the above formula [II] represents a hydrogen atom, $C_1$–$C_6$ alkanoyl group, or $C_2$–$C_7$ alkoxycarbonyl group. However, the above formula [II] does not involve the same limitations as made in the above formula [I] with respect to cases where $R^3$ represents a hydrogen atom, where $R^3$ represents a hydrogen atom and k represents 2, and where $R^3$ represents cyano group.

The cyclic diamine derivative represented by the formula [II] above or its pharmacologically acceptable acid adduct can be used to prepare a chemokine receptor antagonist preparation of the present invention by formulating the therapeutically required amount and a carrier and/or diluent into a pharmaceutical composition. Thus, the cyclic diamine derivative shown by the above formula [II] or its pharmacologically acceptable acid adduct can be administered orally or by parenterally, for example, intravenously, subcutaneously, intramuscularly, percutaneously or intrarectally.

The oral administration can be accomplished in the form of tablets, pills, granules, powder, solution, suspension, capsules, etc.

The tablets for example can be prepared using a vehicle such as lactose, starch and crystallized cellulose; binder such as carboxymethylcellulose, methylcellulose, and polyvinylpyrrolidone; disintegrator such as sodium alginate, sodium bicarbonate and sodium lauryl sulfate, etc.

Pills, powder and granule preparations can be prepared by a standard method using the vehicles mentioned above. Solution or suspension can be prepared by a standard method using glycerin ester such as tricaprylin and triacetin or alcohols such as ethanol. Capsules can be made by charging granules, powder or solution in gelatin, etc.

Subcutaneous, intramuscular or intravenous preparations can be prepared as an injection using aqueous or nonaqueous solution. Aqueous solution for example may include isotonic sodium chloride solution. Nonaqueous solutions may include for example, propyleneglycol, polyethyleneglycol, olive oil, ethyl oleate, etc., and optionally, one can add antiseptics and stabilizers. For injection, one can be sterilized by filtration through a bacterial filter or combination of disinfectant.

Percutaneous administration may be in the form of an ointment or cream, and ointment can be prepared in the standard manner using fatty oils such as castor oil and olive oil. or Vaseline, while creams can be made using fatty oils or emulsifying agent such as diethylene glycol and sorbitan esters of fatty acid.

For intrarectal administration, one can use standard suppositories using gelatin soft capsules, etc.

The cyclic diamine derivative of the present invention or its pharmacologically acceptable acid adduct is administered at a dose that varies depending on the type of disease, route of administration, age and sex of patient, and severity of disease, but is likely to be 1–500 mg/day in an average adult.

(3) Matter Common Throughout Invention 1 and Invention 2

Preferred specific examples for the cyclic diamine derivatives in the above formula [I] or formula [II] include compounds having each substituent as shown in the following Tables 1.1–1.25.

Table 1.1–Table 1.25

TABLE 1.1

| Compound No. | R¹ | R² | R³ | j | k | R⁴ |
|---|---|---|---|---|---|---|
| 1 | 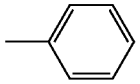 | 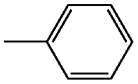 | CN | 2 | 2 | 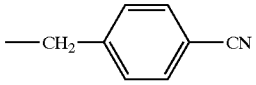 |
| 2 | 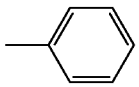 | 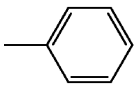 | CN | 2 | 3 | 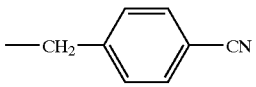 |
| 3 | 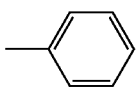 | 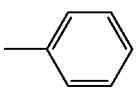 | CN | 2 | 3 | 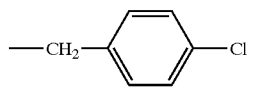 |
| 4 | 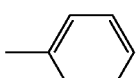 | 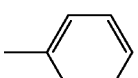 | CN | 2 | 3 | 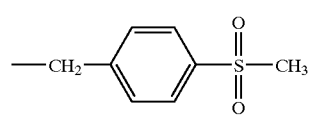 |
| 5 | 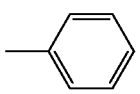 | 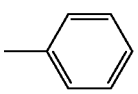 | H | 0 | 3 | 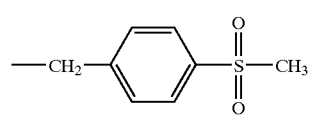 |
| 6 | 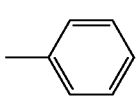 | 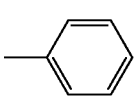 | H | 1 | 3 | 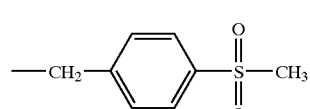 |
| 7 | 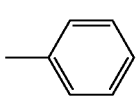 | 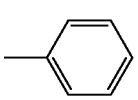 | H | 2 | 2 | 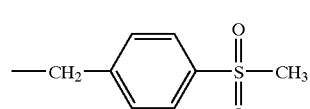 |
| 8 | 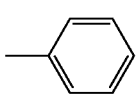 | 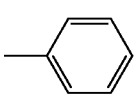 | H | 2 | 2 | 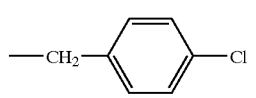 |
| 9 | 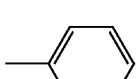 | 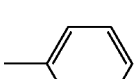 | H | 2 | 2 | 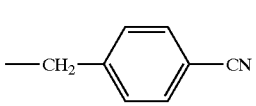 |
| 10 | 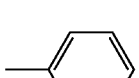 | 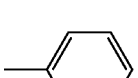 | H | 2 | 2 | 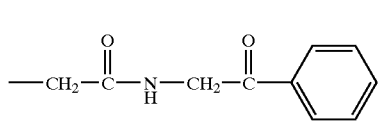 |
| 11 | 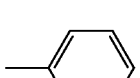 | 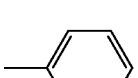 | H | 2 | 2 | 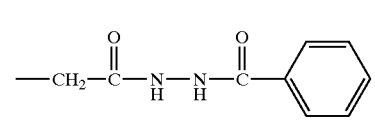 |

TABLE 1.1-continued

| Compound No. | R¹ | R² | R³ | j | k | R⁴ |
|---|---|---|---|---|---|---|
| 12 | —C₆H₅ | —C₆H₅ | H | 2 | 2 | —CH₂—(2-OH, 4-NO₂-C₆H₃) |
| 13 | —C₆H₅ | —C₆H₅ | H | 2 | 2 | —CH₂C(O)NH—(2-NO₂, 4-OCH₃-C₆H₃) |
| 14 | —C₆H₅ | —C₆H₅ | H | 2 | 2 | —CH₂C(O)NH—(3-OCH₃, 4-NHC(O)CH₃-C₆H₃) |
| 15 | —C₆H₅ | —C₆H₅ | H | 2 | 3 | —CH₂—C₆H₅ |
| 16 | —C₆H₅ | —C₆H₅ | H | 2 | 3 | —CH₂C(O)NH—C₆H₅ |
| 17 | —C₆H₅ | —C₆H₅ | H | 2 | 3 | —(CH₂)₂—NHSO₂—(4-Cl-C₆H₄) |
| 18 | —C₆H₅ | —C₆H₅ | H | 2 | 3 | —CH₂C(O)NH—CH₂—C₆H₅ |
| 19 | —C₆H₅ | —C₆H₅ | H | 2 | 3 | —(CH₂)₂—O—C₆H₅ |
| 20 | —C₆H₅ | —C₆H₅ | H | 2 | 3 | —(CH₂)₂—NHC(O)NH—C₆H₅ |
| 21 | —C₆H₅ | —C₆H₅ | H | 2 | 3 | —(CH₂)₂—NHC(O)—C₆H₅ |
| 22 | —C₆H₅ | —C₆H₅ | H | 2 | 3 | —CH₂C(O)O—CH₂—C₆H₅ |
| 23 | —C₆H₅ | —C₆H₅ | H | 2 | 3 | —CH₂—(4-NO₂-C₆H₄) |

TABLE 1.1-continued

| Compound No. | R¹ | R² | R³ | j | k | R⁴ |
|---|---|---|---|---|---|---|
| 24 | phenyl | phenyl | H | 2 | 3 | —CH₂—(3-nitrophenyl) |
| 25 | phenyl | phenyl | H | 2 | 3 | —CH₂—(2-nitrophenyl) |
| 26 | phenyl | phenyl | H | 2 | 3 | —CH₂—(4-methoxyphenyl) |
| 27 | phenyl | phenyl | H | 2 | 3 | —CH₂—(3-methoxyphenyl) |
| 28 | phenyl | phenyl | H | 2 | 3 | —CH₂—(2-methoxyphenyl) |
| 29 | phenyl | phenyl | H | 2 | 3 | —CH₂—(2-nitro-6-methylphenyl) |
| 30 | phenyl | phenyl | H | 2 | 3 | —CH₂—(4-cyanophenyl) |
| 31 | phenyl | phenyl | H | 2 | 3 | —CH₂—(4-trifluoromethylphenyl) |
| 32 | phenyl | phenyl | H | 2 | 3 | —(CH₂)₂—(4-nitrophenyl) |
| 33 | phenyl | phenyl | H | 2 | 3 | —(CH₂)₃—(4-nitrophenyl) |
| 34 | phenyl | phenyl | H | 2 | 3 | —CH₂—(4-chlorophenyl) |
| 35 | phenyl | phenyl | H | 2 | 3 | —CH₂—(4-nitro-3-methoxyphenyl) |

TABLE 1.1-continued

| Compound No. | R¹ | R² | R³ | j | k | R⁴ |
|---|---|---|---|---|---|---|
| 36 | phenyl | phenyl | H | 2 | 3 | —CH₂—(4-methylsulfonylphenyl) |
| 37 | phenyl | phenyl | H | 2 | 3 | —CH₂—(4-CO₂CH₂-phenyl) |
| 38 | phenyl | 4-CH₃-phenyl | H | 2 | 3 | —CH₂—(4-methylsulfonylphenyl) |
| 39 | phenyl | 3-CH₃-phenyl | H | 2 | 3 | —CH₂—(4-methylsulfonylphenyl) |
| 40 | phenyl | 2,3-dimethylphenyl | H | 2 | 3 | —CH₂—(4-methylsulfonylphenyl) |
| 41 | phenyl | 4-OCH₃-phenyl | H | 2 | 3 | —CH₂—(4-methylsulfonylphenyl) |
| 42 | phenyl | 4-OH-phenyl | H | 2 | 3 | —CH₂—(4-methylsulfonylphenyl) |
| 43 | phenyl | 4-Cl-phenyl | H | 2 | 3 | —CH₂—(4-methylsulfonylphenyl) |
| 44 | phenyl | 4-OCH₃-phenyl | H | 2 | 3 | —CH₂—(4-Cl-phenyl) |
| 45 | phenyl | 3-F-phenyl | H | 2 | 3 | —CH₂—(4-methylsulfonylphenyl) |
| 46 | phenyl | 4-OH-phenyl | H | 2 | 3 | —CH₂—(4-Cl-phenyl) |
| 47 | 4-F-phenyl | 4-F-phenyl | H | 2 | 3 | —CH₂—(4-methylsulfonylphenyl) |

TABLE 1.1-continued

| Compound No. | R¹ | R² | R³ | j | k | R⁴ |
|---|---|---|---|---|---|---|
| 48 | phenyl | 4-F-phenyl | H | 2 | 3 | —CH₂—(4-SO₂CH₃-phenyl) |
| 49 | phenyl | 2-F-phenyl | H | 2 | 3 | —CH₂—(4-SO₂CH₃-phenyl) |
| 50 | phenyl | 4-Cl-phenyl | H | 2 | 3 | —CH₂—(4-Cl-phenyl) |
| 51 | phenyl | 2-Cl-phenyl | H | 2 | 3 | —CH₂—(4-SO₂CH₃-phenyl) |
| 52 | phenyl | phenyl | H | 2 | 3 | —CH₂—(4-F-phenyl) |
| 53 | 4-Cl-phenyl | 4-Cl-phenyl | H | 2 | 3 | —CH₂—(4-Cl-phenyl) |
| 54 | 4-F-phenyl | 4-F-phenyl | H | 2 | 3 | —CH₂—(4-Cl-phenyl) |
| 55 | phenyl | phenyl | H | 2 | 3 | —CH₂—(4-CONH₂-phenyl) |
| 56 | 4-Cl-phenyl | 4-Cl-phenyl | H | 2 | 3 | —CH₂—(4-SO₂CH₃-phenyl) |
| 57 | phenyl | phenyl | H | 2 | 3 | —CH₂—(4-OH-phenyl) |
| 58 | phenyl | 3-OH-phenyl | H | 2 | 3 | —CH₂—(4-SO₂CH₃-phenyl) |
| 59 | phenyl | 2-OH-phenyl | H | 2 | 3 | —CH₂—(4-SO₂CH₃-phenyl) |
| 60 | phenyl | phenyl | H | 2 | 3 | —CH₂—(4-CON(CH₃)₂-phenyl) |

TABLE 1.1-continued

| Compound No. | R¹ | R² | R³ | j | k | R⁴ |
|---|---|---|---|---|---|---|
| 61 | –C₆H₅ | –C₆H₅ | H | 2 | 3 | –CH₂–C₆H₄–SO₂NH₂ (para) |
| 62 | –C₆H₄–CF₃ (para) | –C₆H₄–CF₃ (para) | H | 2 | 3 | –CH₂–C₆H₄–Cl (para) |
| 63 | –C₆H₅ | –C₆H₄–OH (meta) | H | 2 | 3 | –CH₂–C₆H₄–Cl (para) |
| 64 | –C₆H₅ | –C₆H₄–OH (ortho) | H | 2 | 3 | –CH₂–C₆H₄–Cl (para) |
| 65 | –C₆H₄–OCH₃ (para) | –C₆H₄–OCH₃ (para) | H | 2 | 3 | –CH₂–C₆H₄–Cl (para) |
| 66 | –C₆H₄–OH (para) | –C₆H₄–OH (para) | H | 2 | 3 | –CH₂–C₆H₄–Cl (para) |
| 67 | –C₆H₄–OH (para) | –C₆H₄–OH (para) | H | 2 | 3 | –CH₂–C₆H₄–S(O)₂–CH₃ (para) |
| 68 | –C₆H₄–OH (meta) | –C₆H₄–OH (meta) | H | 2 | 3 | –CH₂–C₆H₄–S(O)₂–CH₃ (para) |
| 69 | –C₆H₅ | –C₆H₄–CO₂C(CH₃)₃ (para) | H | 2 | 3 | –CH₂–C₆H₄–S(O)₂–CH₃ (para) |
| 70 | –C₆H₅ | –C₆H₅ | H | 2 | 3 | –CH₂–C(O)–NH–(2,6-di-CH₂CH₃-C₆H₃) |
| 71 | –C₆H₅ | –C₆H₅ | H | 2 | 3 | –CH₂–C(=NH)–NH–SO₂–C₆H₄–Cl (para) |
| 72 | –C₆H₅ | –C₆H₄–CO₂CH₃ (para) | H | 2 | 3 | –CH₂–C₆H₄–S(O)₂–CH₃ (para) |

TABLE 1.1-continued
| Compound No. | R¹ | R² | R³ | j | k | R⁴ |
|---|---|---|---|---|---|---|
| 73 | 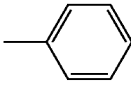 | 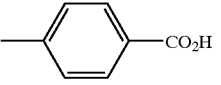 —CO₂H | H | 2 | 3 | 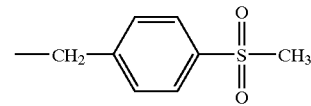 |
| 74 | 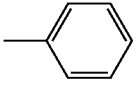 | 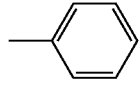 | H | 2 | 3 | 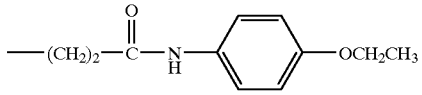 |
| 75 | 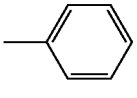 | 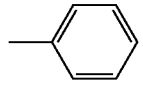 | H | 2 | 3 | 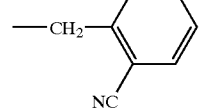 |
| 76 | 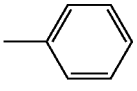 | 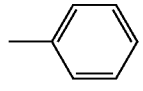 | H | 2 | 3 | 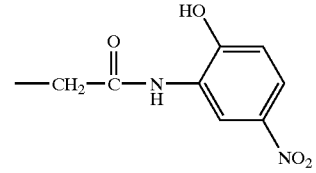 |
| 77 | 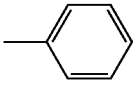 | 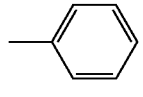 | H | 2 | 3 | 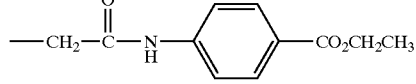 |
| 78 | 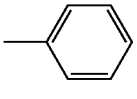 | 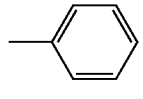 | H | 2 | 3 | 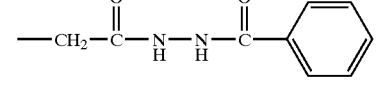 |
| 79 | 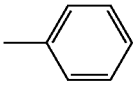 | 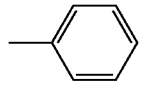 | H | 2 | 3 | 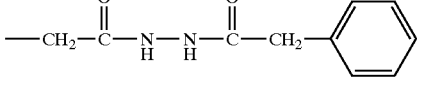 |
| 80 | 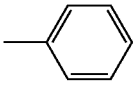 | 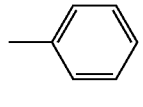 | H | 2 | 3 | 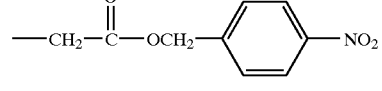 |
| 81 | 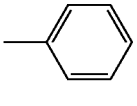 | 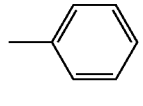 | H | 2 | 3 | 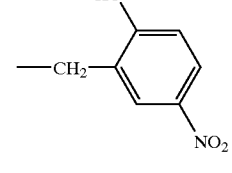 |
| 82 | 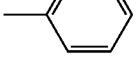 | 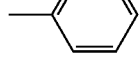 | H | 2 | 3 | 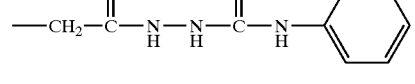 |
| 83 | 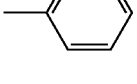 | 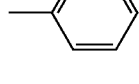 | H | 2 | 3 | 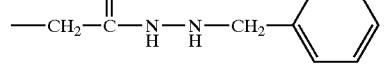 |

TABLE 1.1-continued
| Compound No. | R¹ | R² | R³ | j | k | R⁴ |
|---|---|---|---|---|---|---|
| 84 | 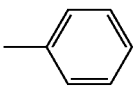 | 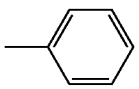 | H | 2 | 3 | 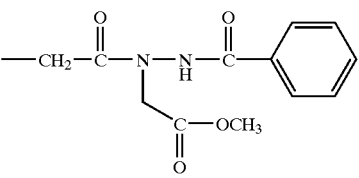 |
| 85 | 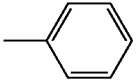 | 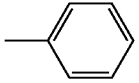 | H | 2 | 3 | 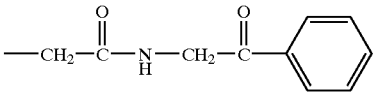 |
| 86 | 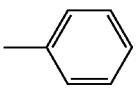 | 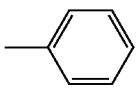 | H | 2 | 3 | 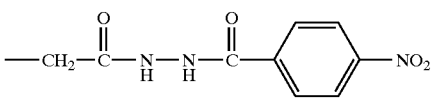 |
| 87 | 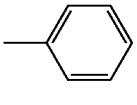 | 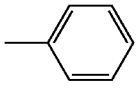 | H | 2 | 3 | 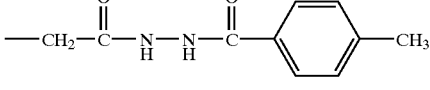 |
| 88 | 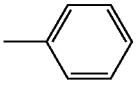 | 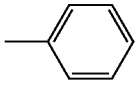 | H | 2 | 3 | 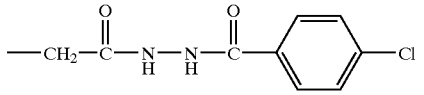 |
| 89 | 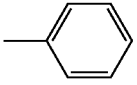 | 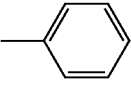 | H | 2 | 3 | 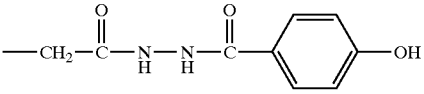 |
| 90 | 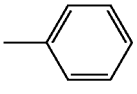 | 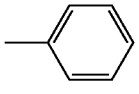 | H | 2 | 3 | 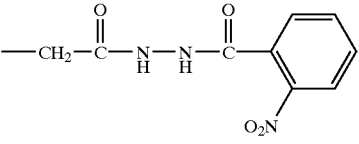 |
| 91 | 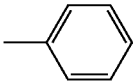 | 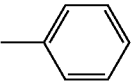 | H | 2 | 3 | 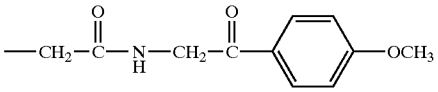 |
| 92 | 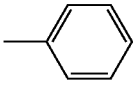 | 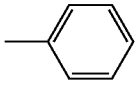 | H | 2 | 3 | 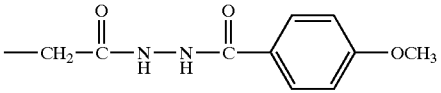 |
| 93 | 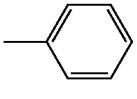 | 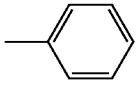 | H | 2 | 3 | 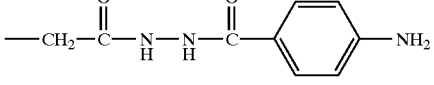 |
| 94 | 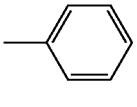 | 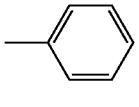 | H | 2 | 3 | 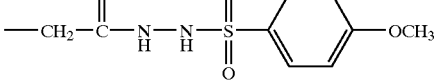 |
| 95 | 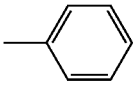 | 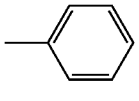 | H | 2 | 3 | 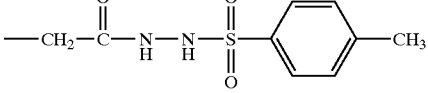 |

TABLE 1.1-continued

| Compound No. | R¹ | R² | R³ | j | k | R⁴ |
|---|---|---|---|---|---|---|
| 96 | —C₆H₅ | —C₆H₅ | H | 2 | 3 | —CH₂—C(O)—NH—NH—S(O)₂—C₆H₄—NH—C(O)—CH₃ (para) |
| 97 | —C₆H₅ | —C₆H₅ | H | 2 | 3 | —CH₂—C(O)—NH—NH—S(O)₂—C₆H₄—Cl (para) |
| 98 | —C₆H₅ | —C₆H₅ | H | 2 | 3 | —CH₂—C(O)—NH—NH—C(O)—C₆H₄—Br (para) |
| 99 | —C₆H₅ | —C₆H₅ | H | 2 | 3 | —CH₂—C(O)—NH—NH—C(O)—C₆H₄—S(O)₂—CH₃ (para) |
| 100 | —C₆H₅ | —C₆H₅ | H | 2 | 3 | —CH₂—C(O)—NH—NH—C(O)—C₆H₄—C(O)—CH₃ (para) |
| 101 | —C₆H₅ | —C₆H₄—OH (meta) | H | 2 | 3 | —CH₂—C(O)—NH—CH₂—C(O)—C₆H₅ |
| 102 | —C₆H₅ | —C₆H₅ | H | 2 | 3 | —CH₂—C₆H₄—S(O)₂—CH₃ (para) |
| 103 | —C₆H₅ | —C₆H₅ | OCH₃ | 2 | 3 | —CH₂—C₆H₄—S(O)₂—CH₃ (para) |
| 104 | —C₆H₄—OH (meta) | —C₆H₄—OH (meta) | OCH3 | 2 | 3 | —CH₂—C₆H₄—S(O)₂—CH₃ (para) |
| 105 | —C₆H₅ | —C₆H₄—OH (meta) | OCOCH₃ | 2 | 3 | —CH₂—C₆H₄—S(O)₂—CH₃ (para) |
| 106 | —C₆H₅ | —C₆H₅ | OH | 2 | 3 | —CH₂—C₆H₄—S(O)₂—CH₃ (para) |
| 107 | —C₆H₅ | —C₆H₅ | OH | 2 | 3 | —CH₂—C₆H₄—Cl (para) |

TABLE 1.1-continued
| Compound No. | R¹ | R² | R³ | j | k | R⁴ |
|---|---|---|---|---|---|---|
| 108 | 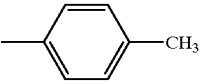 | 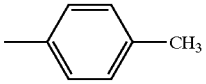 | OH | 2 | 3 | 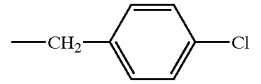 |
| 109 | 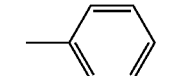 | 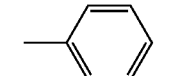 | OH | 2 | 3 | 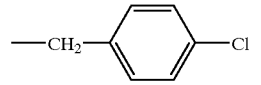 |
| 110 |  | 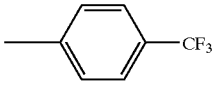 | OH | 2 | 3 | 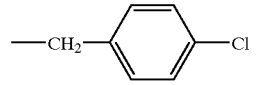 |
| 111 | 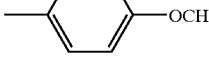 | 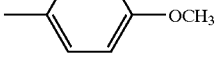 | OH | 2 | 3 | 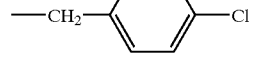 |
| 112 | 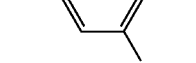 | 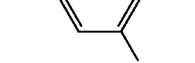 | OH | 2 | 3 | 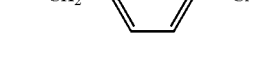 |
| 113 | 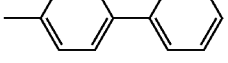 | 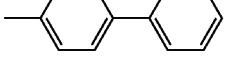 | OH | 2 | 3 | 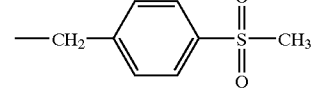 |
| 114 | 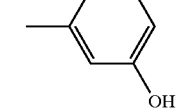 | 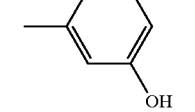 | OH | 2 | 3 | 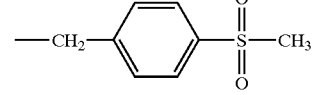 |
| 115 | 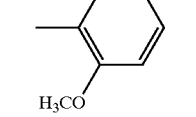 | 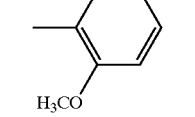 | OH | 2 | 3 | 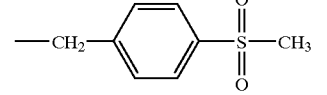 |
| 116 | 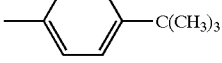 | 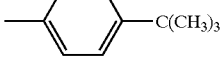 | OH | 2 | 3 | 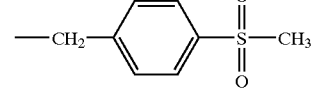 |
| 117 |  |  | OH | 2 | 3 | 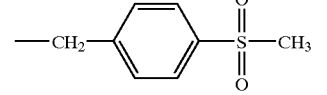 |
| 118 | 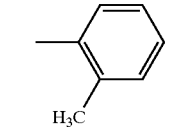 | 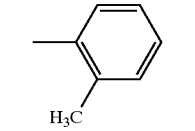 | OH | 2 | 3 | 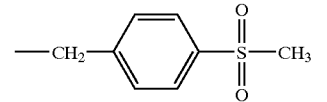 |
| 119 | 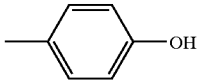 | 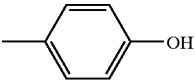 | OH | 2 | 3 | 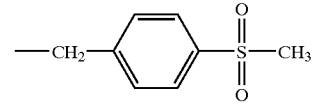 |

TABLE 1.1-continued
| Compound No. | R¹ | R² | R³ | j | k | R⁴ |
|---|---|---|---|---|---|---|
| 120 | 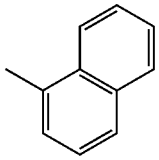 | 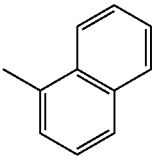 | OH | 2 | 3 | 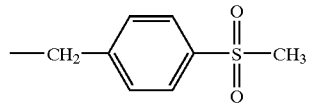 |
| 121 | 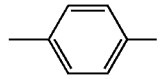 | 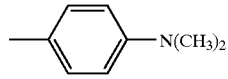 | OH | 2 | 3 | 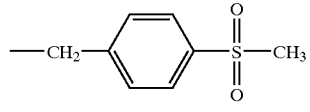 |
| 122 | 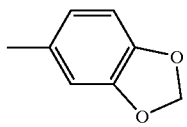 | 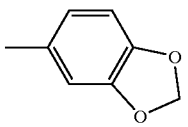 | OH | 2 | 3 | 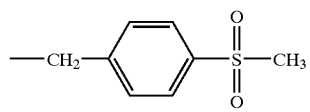 |
| 123 |  |  | OH | 2 | 3 | 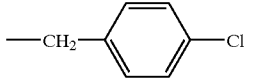 |
| 124 | 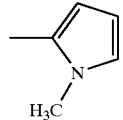 | 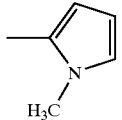 | OH | 2 | 3 | 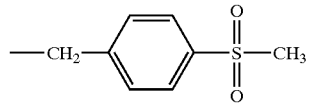 |
| 125 | 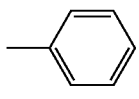 | 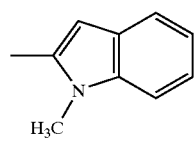 | OH | 2 | 3 | 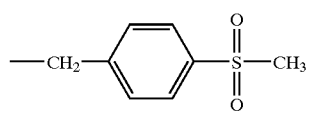 |
| 126 | 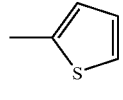 | 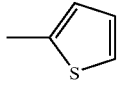 | OH | 2 | 3 | 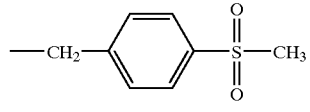 |
| 127 | 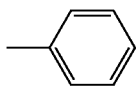 | 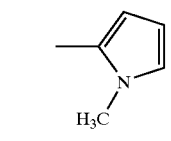 | OH | 2 | 3 | 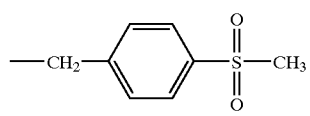 |
| 128 | 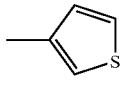 | 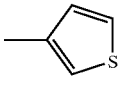 | OH | 2 | 3 | 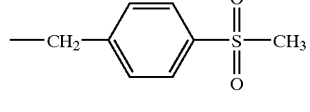 |
| 129 | 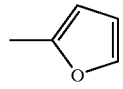 | 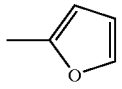 | OH | 2 | 3 | 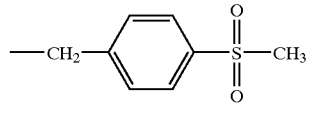 |
| 130 | 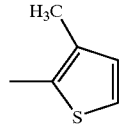 | 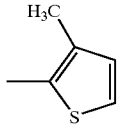 | OH | 2 | 3 | 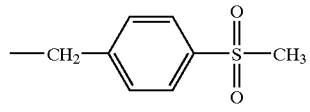 |

TABLE 1.1-continued
| Compound No. | R¹ | R² | R³ | j | k | R⁴ |
|---|---|---|---|---|---|---|
| 131 | 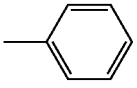 | 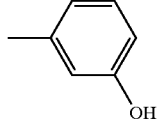 | OH | 2 | 3 | 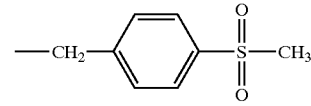 |
| 132 | 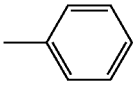 | 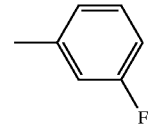 | OH | 2 | 3 | 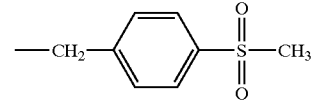 |
| 133 | 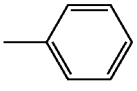 | 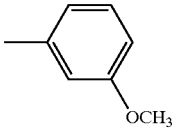 | OH | 2 | 3 | 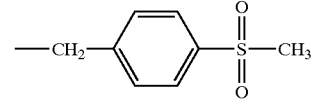 |
| 134 | 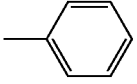 | 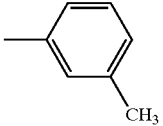 | OH | 2 | 3 | 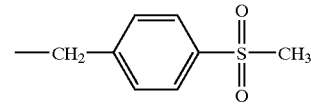 |
| 135 | 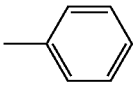 | 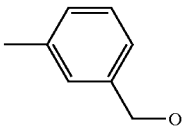 | OH | 2 | 3 | 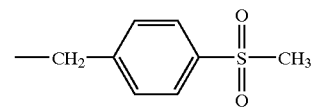 |
| 136 | 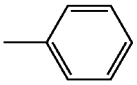 | 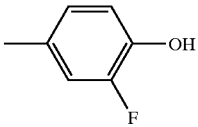 | OH | 2 | 3 | 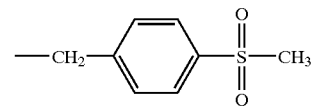 |
| 137 |  | 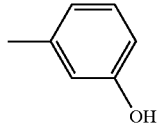 | OH | 2 | 3 | 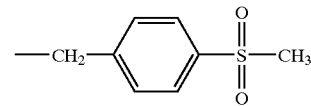 |
| 138 | 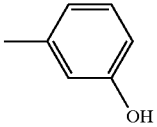 | 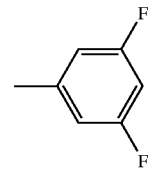 | OH | 2 | 3 | 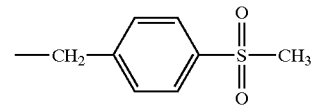 |
| 139 | 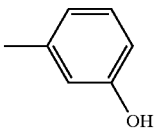 | 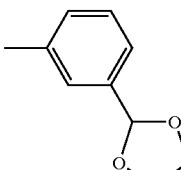 | OH | 2 | 3 | 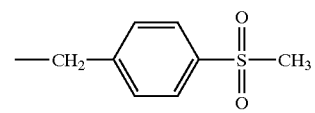 |
| 140 | 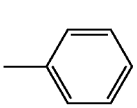 | 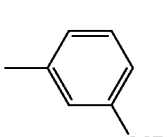 | OH | 2 | 3 | 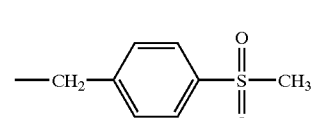 |

TABLE 1.1-continued

| Compound No. | R¹ | R² | R³ | j | k | R⁴ |
|---|---|---|---|---|---|---|
| 141 | -C₆H₅ | 4-methyl-2,5-dimethoxyphenyl (methyl-,OCH₃, H₃CO-) | OH | 2 | 3 | -CH₂-C₆H₄-S(=O)₂-CH₃ |
| 142 | -C₆H₅ | 3,5-dimethoxy-methylphenyl (OCH₃, OCH₃) | OH | 2 | 3 | -CH₂-C₆H₄-S(=O)₂-CH₃ |
| 143 | -C₆H₅ | 3-(N-methyl-N-allylamino)methylphenyl | OH | 2 | 3 | -CH₂-C₆H₄-S(=O)₂-CH₃ |
| 144 | -C₆H₅ | -C₆H₅ | H | 2 | 3 | -CH₂-C₆H₄-S(=O)₂-CF₃ |
| 145 | 3-hydroxyphenyl | 3-(2-hydroxyethyl)phenyl | OH | 2 | 3 | -CH₂-C₆H₄-S(=O)₂-CH₃ |
| 146 | -C₆H₅ | 3-(methylamino)methylphenyl | OH | 2 | 3 | -CH₂-C₆H₄-S(=O)₂-CH₃ |
| 147 | -C₆H₅ | 3-phenoxymethylphenyl | OH | 2 | 3 | -CH₂-C₆H₄-S(=O)₂-CH₃ |
| 148 | -C₆H₅ | 4-hydroxy-3-methoxy-methylphenyl | OH | 2 | 3 | -CH₂-C₆H₄-S(=O)₂-CH₃ |
| 149 | -C₆H₅ | 3-hydroxy-5-methoxy-methylphenyl | OH | 2 | 3 | -CH₂-C₆H₄-S(=O)₂-CH₃ |

TABLE 1.1-continued
| Compound No. | R¹ | R² | R³ | j | k | R⁴ |
|---|---|---|---|---|---|---|
| 150 | 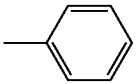 | 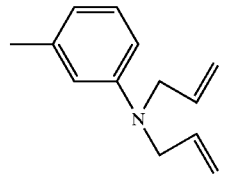 | OH | 2 | 3 | 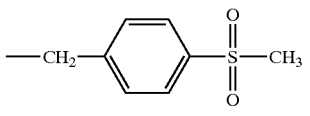 |
| 151 | 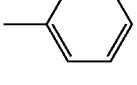 | 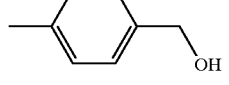 | OH | 2 | 3 | 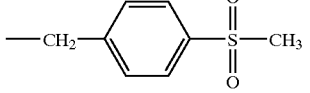 |
| 152 | 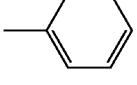 | 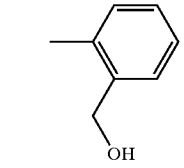 | OH | 2 | 3 | 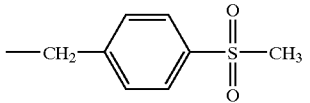 |
| 153 | 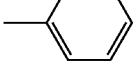 | 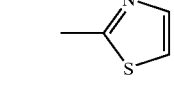 | OH | 2 | 3 | 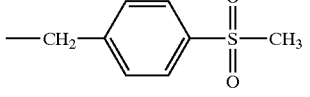 |
| 154 | 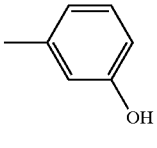 | 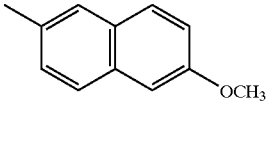 | OH | 2 | 3 | 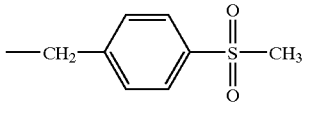 |
| 155 | 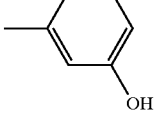 | 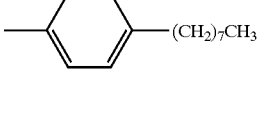 | OH | 2 | 3 | 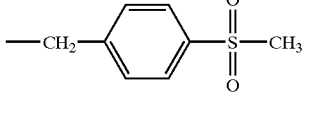 |
| 156 | 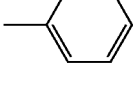 | 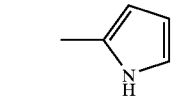 | OH | 2 | 3 | 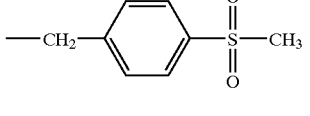 |
| 157 | 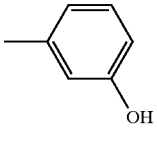 | 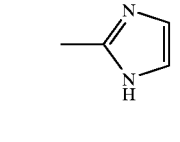 | OH | 2 | 3 | 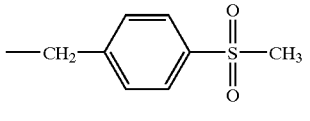 |
| 158 | 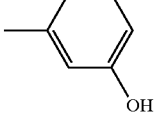 | 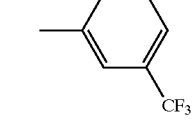 | OH | 2 | 3 | 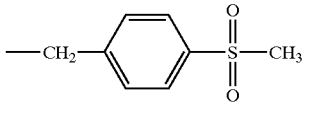 |
| 159 | 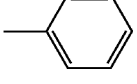 | 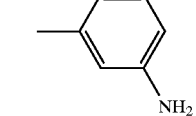 | OH | 2 | 3 | 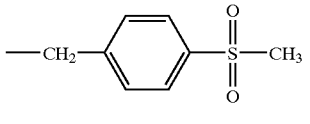 |

TABLE 1.1-continued
| Compound No. | R¹ | R² | R³ | j | k | R⁴ |
|---|---|---|---|---|---|---|
| 160 | 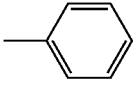 | 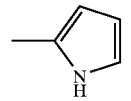 | OH | 2 | 3 | 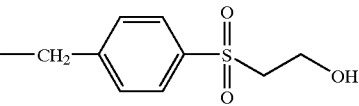 |
| 161 | 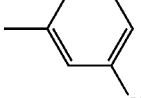 | 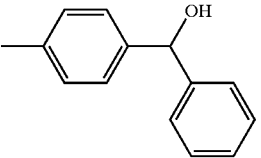 | OH | 2 | 3 | 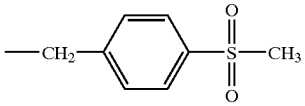 |
| 162 | 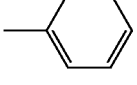 | 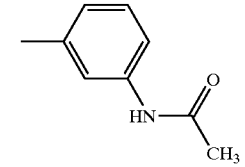 | OH | 2 | 3 | 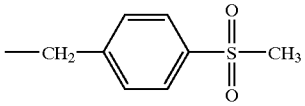 |
| 163 | 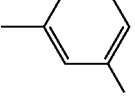 | 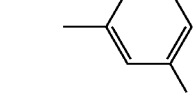 | OH | 2 | 3 | 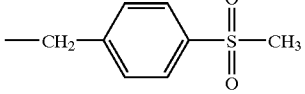 |
| 164 |  | 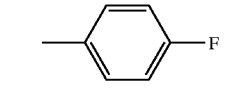 | OH | 2 | 3 | 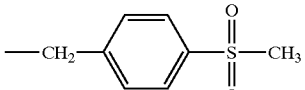 |
| 165 | 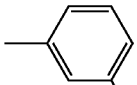 | 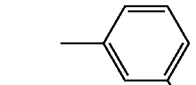 | OH | 2 | 3 | 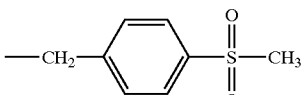 |
| 166 | 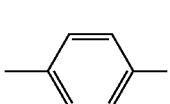 | 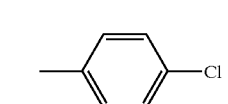 | OH | 2 | 3 | 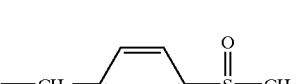 |
| 167 | 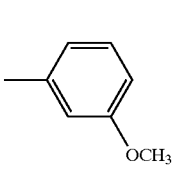 | 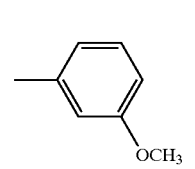 | OH | 2 | 3 | 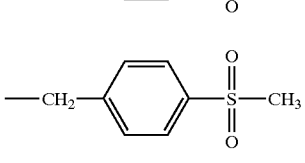 |
| 168 | 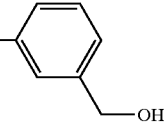 | 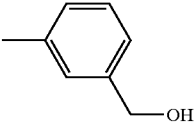 | OH | 2 | 3 | 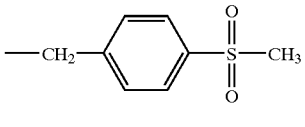 |
| 169 | 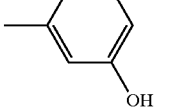 | 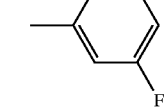 | OH | 2 | 3 | 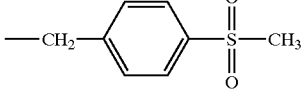 |

TABLE 1.1-continued

| Compound No. | R¹ | R² | R³ | j | k | R⁴ |
|---|---|---|---|---|---|---|
| 170 | 3-hydroxyphenyl | 3-chlorophenyl | OH | 2 | 3 | —CH₂—(4-methylsulfonylphenyl) |
| 171 | 3-hydroxyphenyl | 4-chlorophenyl | OH | 2 | 3 | —CH₂—(4-methylsulfonylphenyl) |
| 172 | 3-hydroxyphenyl | 3,5-dimethoxyphenyl | OH | 2 | 3 | —CH₂—(4-methylsulfonylphenyl) |
| 173 | 3-hydroxyphenyl | 3-methoxyphenyl | OH | 2 | 3 | —CH₂—(4-methylsulfonylphenyl) |
| 174 | phenyl | phenyl | OH | 2 | 3 | —CH₂—(4-ethylsulfonylphenyl) |
| 175 | phenyl | phenyl | OH | 2 | 3 | —CH₂—(4-(n-propylsulfonyl)phenyl) |
| 176 | phenyl | phenyl | OH | 2 | 3 | —CH₂—(4-(isopropylsulfonyl)phenyl) |
| 177 | phenyl | phenyl | OH | 2 | 3 | —CH₂—(4-(n-butylsulfonyl)phenyl) |
| 178 | phenyl | phenyl | OH | 2 | 3 | —CH₂—(4-(phenylsulfonyl)phenyl) |
| 179 | phenyl | phenyl | OH | 2 | 3 | —CH₂—(3-methylsulfonylphenyl) |

TABLE 1.1-continued
| Compound No. | R¹ | R² | R³ | j | k | R⁴ |
|---|---|---|---|---|---|---|
| 180 | 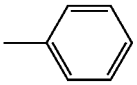 | 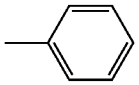 | OH | 2 | 3 | 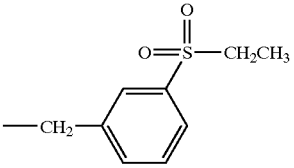 |
| 181 | 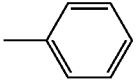 | 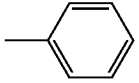 | OH | 2 | 3 | 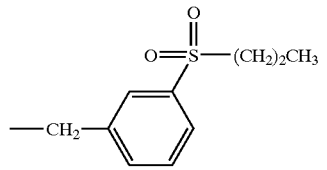 |
| 182 | 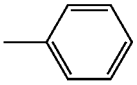 | 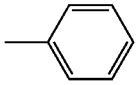 | OH | 2 | 3 | 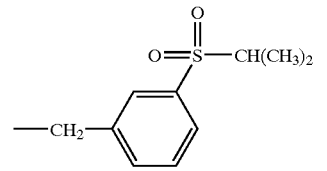 |
| 183 | 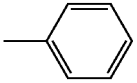 | 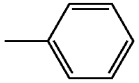 | OH | 2 | 3 | 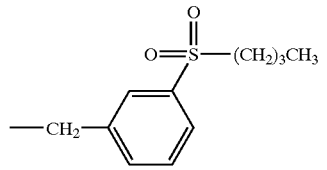 |
| 184 | 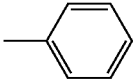 | 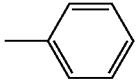 | OH | 2 | 3 | 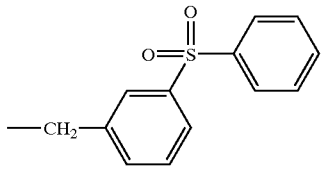 |
| 185 | 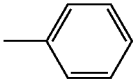 | 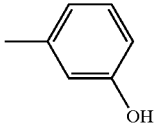 | OH | 2 | 3 | 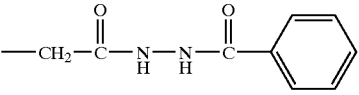 |
| 186 | 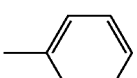 | 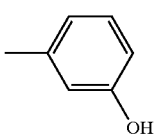 | OH | 2 | 3 | 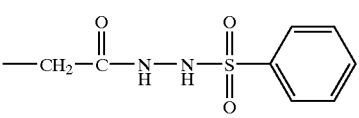 |
| 187 | 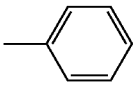 | 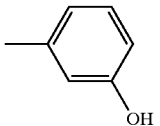 | OH | 2 | 3 | 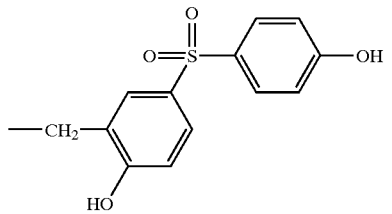 |

TABLE 1.1-continued

| Compound No. | R¹ | R² | R³ | j | k | R⁴ |
|---|---|---|---|---|---|---|
| 188 | phenyl | 3-hydroxyphenyl | OH | 2 | 3 | —(CH₂)₃—SO₂—C₆H₄—CH₃ (p-tolyl) |
| 189 | phenyl | 3-hydroxyphenyl | OH | 2 | 3 | —CH₂—C(O)—NH—CH₂—C(O)—phenyl |
| 190 | phenyl | 3-hydroxyphenyl | OH | 2 | 3 | —CH₂—C₆H₄—SO₂—N(pyrrole) |
| 191 | phenyl | 3-hydroxyphenyl | OH | 2 | 3 | —CH₂—C(O)—NH—NH—C(O)—C₆H₄—OH (p-hydroxyphenyl) |
| 192 | phenyl | 3-hydroxyphenyl | OH | 2 | 3 | —CH₂—C(O)—C₆H₃(OH)₂ (3,4-dihydroxyphenyl) |
| 193 | phenyl | 3-hydroxyphenyl | OH | 2 | 3 | —CH₂—C(O)—NH—C₆H₃(F)(NO₂) (4-fluoro-3-nitrophenyl) |
| 194 | phenyl | 3-hydroxyphenyl | OH | 2 | 3 | —CH₂—C(O)—NH—NH—C(O)—C₆H₄—Cl (p-chlorophenyl) |
| 195 | phenyl | 3-hydroxyphenyl | OH | 2 | 3 | —CH₂—C(O)—NH—NH—C(O)—NH—phenyl |
| 196 | phenyl | 3-hydroxyphenyl | OH | 2 | 3 | —CH₂—C(=NH)—NH—SO₂—C₆H₄—Cl (p-chlorophenyl) |
| 197 | phenyl | phenyl | OH | 3 | 3 | —CH₂—C₆H₄—SO₂—CH₃ |

TABLE 1.1-continued

| Compound No. | R¹ | R² | R³ | j | k | R⁴ |
|---|---|---|---|---|---|---|
| 198 | 3-hydroxyphenyl | 3-hydroxyphenyl | OH | 3 | 3 | —CH₂—C₆H₄—S(O)₂—CH₃ |
| 199 | phenyl | phenyl | H | 2 | 3 | —C(O)—C₆H₅ |
| 200 | phenyl | phenyl | H | 2 | 3 | 4-chlorophenyl-S(O)₂— |
| 201 | phenyl | phenyl | H | 2 | 3 | —C(O)-(4-pyridyl) |
| 202 | phenyl | phenyl | H | 2 | 3 | —C(O)—C₆H₄—CH₂—N(CH₃)₃ |
| 203 | phenyl | phenyl | H | 2 | 3 | —C(O)—CH₂—N(CH₃)—CH₂—C₆H₅ |
| 204 | phenyl | phenyl | H | 2 | 3 | —C(O)-[2-(2-oxoimidazolidin-1-yl)phenyl] |
| 205 | phenyl | phenyl | H | 2 | 3 | —(CH₂)₂CH₃ |
| 206 | phenyl | phenyl | H | 2 | 3 | —CH₂-(7-methoxy-2-oxo-2H-chromen-4-yl) |
| 207 | phenyl | phenyl | H | 2 | 3 | —CH₂-(1H-benzimidazol-2-yl) |

TABLE 1.1-continued

| Compound No. | R¹ | R² | R³ | j | k | R⁴ |
|---|---|---|---|---|---|---|
| 208 | phenyl | phenyl | H | 2 | 3 | —CH₂-(5-yl of uracil / 2,4-dioxo-1,2,3,4-tetrahydropyrimidine) |
| 209 | phenyl | phenyl | H | 2 | 3 | —(CH₂)₂—CO₂CH₃ |
| 210 | phenyl | phenyl | H | 2 | 3 | —CH₂C≡CCH₃ |
| 211 | phenyl | phenyl | H | 2 | 3 | —CH₂-cyclopropyl |
| 212 | phenyl | phenyl | H | 2 | 3 | —CH₂-(4-yl of 7-hydroxy-2H-chromen-2-one) |
| 213 | phenyl | phenyl | H | 2 | 3 | —(CH₂)₄—C≡N |
| 214 | phenyl | phenyl | H | 2 | 3 | —(CH₂)₂—C≡N |
| 215 | phenyl | phenyl | H | 2 | 3 | —(CH₂)₃—C≡N |
| 216 | phenyl | phenyl | H | 2 | 3 | —CH₂-(4-yl of 3-methyl-5-(5-methylisoxazol-3-yl)isoxazole) |
| 217 | phenyl | phenyl | H | 2 | 3 | —CH₂—C≡N |
| 218 | phenyl | phenyl | H | 2 | 3 | —CH₂CH(OH)CH₂OCH₂CH₂C≡CH |

TABLE 1.1-continued
| Compound No. | R¹ | R² | R³ | j | k | R⁴ |
|---|---|---|---|---|---|---|
| 219 | 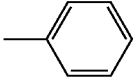 | 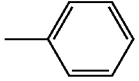 | H | 2 | 3 | 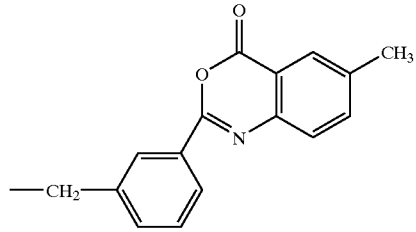 |
| 220 | 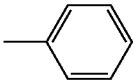 | 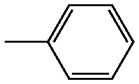 | H | 2 | 3 | —CH$_2$C≡CH |
| 221 | 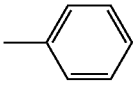 | 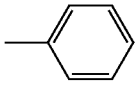 | H | 2 | 3 | 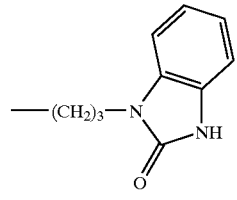 |
| 222 | 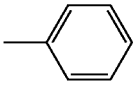 | 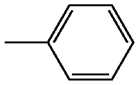 | H | 2 | 3 | 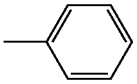 |
| 223 | 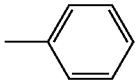 | 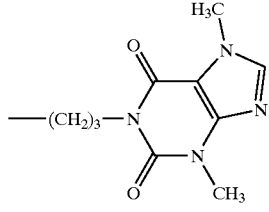 | H | 2 | 3 | 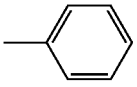 |
| 224 | 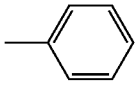 | 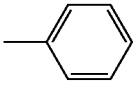 | H | 2 | 3 | 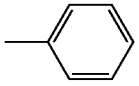 |
| 225 | 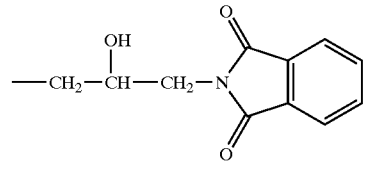 | 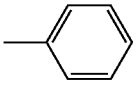 | H | 2 | 3 | 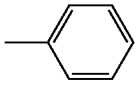 |
| 226 | 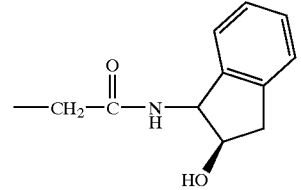 | 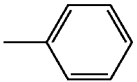 | H | 2 | 3 | 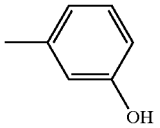 |
| 227 | 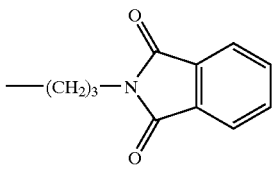 | | OH | 2 | 3 | |

TABLE 1.1-continued

| Compound No. | R¹ | R² | R³ | j | k | R⁴ |
|---|---|---|---|---|---|---|
| 228 | phenyl | 3-hydroxyphenyl | OH | 2 | 3 | —(CH₂)₃—(1-(2-oxo-2,3-dihydro-1H-benzimidazolyl)) |
| 229 | phenyl | 3-hydroxyphenyl | OH | 2 | 3 | pent-2-enyl phenyl sulfone |
| 230 | phenyl | 3-hydroxyphenyl | OH | 2 | 3 | —CH₂—CH(OH)—CH₂—O—C(=O)—C(CH₃)=CH₂ |
| 231 | phenyl | 3-hydroxyphenyl | OH | 2 | 3 | —CH₂—(2,3,5-trimethyl-6,7-dioxo-6,7-dihydro-1H,5H-pyrazolo[1,2-a]pyrazol-1-yl) |
| 232 | phenyl | 3-hydroxyphenyl | OH | 2 | 3 | —CH₂—(5-(2,4-dioxo-1,2,3,4-tetrahydropyrimidinyl)) |
| 233 | phenyl | phenyl | CN | 2 | 3 | —CH₂—(4-pyridyl) |
| 234 | phenyl | phenyl | CN | 2 | 3 | —CH₂—C(=O)—NH—NH—C(=O)—(4-methylthiophen-2-yl) |
| 235 | phenyl | phenyl | H | 2 | 3 | —CH₂—(4-pyridyl) |
| 236 | phenyl | phenyl | H | 2 | 3 | —CH₂—C(=O)—NH—NH—C(=O)—(4-methylthiophen-2-yl) |
| 237 | phenyl | phenyl | H | 2 | 3 | —CH₂—(2-quinolyl) |

TABLE 1.1-continued

| Compound No. | R¹ | R² | R³ | j | k | R⁴ |
|---|---|---|---|---|---|---|
| 238 | phenyl | phenyl | H | 2 | 3 | —(CH₂)₂—(1H-indol-3-yl) |
| 239 | phenyl | phenyl | H | 2 | 3 | —CH₂—(3,5-dimethylisoxazol-4-yl) |
| 240 | phenyl | phenyl | H | 2 | 3 | —CH₂—(pyridin-4-yl) |
| 241 | phenyl | phenyl | H | 2 | 3 | —CH₂—(pyridin-3-yl) |
| 242 | phenyl | phenyl | H | 2 | 3 | —CH₂—(pyridin-2-yl) |
| 243 | phenyl | 4-methoxyphenyl | H | 2 | 3 | —CH₂—(pyridin-4-yl) |
| 244 | phenyl | 4-hydroxyphenyl | H | 2 | 3 | —CH₂—(pyridin-4-yl) |
| 245 | phenyl | 4-chlorophenyl | H | 2 | 3 | —CH₂—(pyridin-4-yl) |
| 246 | phenyl | phenyl | H | 2 | 3 | —CH₂—C(O)—NH—NH—C(O)—(4-methylthiophen-2-yl) |
| 247 | phenyl | phenyl | H | 2 | 3 | —CH₂—(5-chloro-1,2,4-thiadiazol-3-yl) |
| 248 | phenyl | phenyl | H | 2 | 3 | —CH₂—C(O)—NH—NH—C(O)—(4-methyl-3-(1H-pyrrol-1-yl)thiophen-2-yl) |

TABLE 1.1-continued

| Compound No. | R¹ | R² | R³ | j | k | R⁴ |
|---|---|---|---|---|---|---|
| 249 | phenyl | phenyl | H | 2 | 3 | —CH₂—C(=O)—NH—NH—C(=O)—(2,6-dichloropyridin-4-yl) |
| 250 | phenyl | phenyl | H | 2 | 3 | —CH₂—(1,2,4-oxadiazol-3-yl) |
| 251 | phenyl | phenyl | H | 2 | 3 | —CH₂—C(=O)—NH—NH—C(=O)—(furan-2-yl) |
| 252 | phenyl | phenyl | H | 2 | 3 | —CH₂—C(=O)—NH—NH—C(=O)—(thiophen-2-yl) |
| 253 | phenyl | phenyl | H | 2 | 3 | —CH₂CH(OH)CH₂OCH₂—(furan-2-yl) |
| 254 | phenyl | phenyl | H | 2 | 3 | —CH₂—C(=O)—NH—NH—C(=O)—(pyridin-3-yl) |
| 255 | phenyl | phenyl | H | 2 | 3 | —CH₂—C(=O)—NH—NH—C(=O)—(benzothiophen-2-yl) |
| 256 | phenyl | phenyl | H | 2 | 3 | —CH₂—C(=O)—NH—NH—S(=O)₂—(thiophen-2-yl) |
| 257 | phenyl | 3-hydroxyphenyl | H | 2 | 3 | —CH₂—C(=O)—NH—NH—C(=O)—(4-methylthiophen-2-yl) |
| 258 | phenyl | phenyl | OH | 2 | 3 | —CH₂—(pyridin-4-yl) |
| 259 | phenyl | 3-hydroxyphenyl | OH | 2 | 3 | —CH₂—C(=O)—NH—NH—C(=O)—(4-methylthiophen-2-yl) |
| 260 | phenyl | 3-hydroxyphenyl | OH | 2 | 3 | —CH₂—C(=O)—NH—NH—C(=O)—(thiophen-2-yl) |

TABLE 1.1-continued

| Compound No. | R¹ | R² | R³ | j | k | R⁴ |
|---|---|---|---|---|---|---|
| 261 | phenyl | 3-hydroxyphenyl | OH | 2 | 3 | —CH₂—C(O)—NH—NH—C(O)—(2,6-dichloropyridin-4-yl) |
| 262 | phenyl | 3-hydroxyphenyl | OH | 2 | 3 | —CH₂—C(O)—NH—NH—C(O)—(5-methylthiophen-2-yl) |
| 263 | phenyl | 3-hydroxyphenyl | OH | 2 | 3 | —(CH₂)₃—C(O)—(thiophen-2-yl) |
| 264 | phenyl | phenyl | CN | 2 | 3 | —CH₂—C(O)—N(CH₂CH₃)₂ |
| 265 | phenyl | phenyl | H | 2 | 3 | —CH₂—C(O)—N(CH₂CH₃)₂ |
| 266 | phenyl | phenyl | H | 2 | 3 | —CH₂—C(O)—NH₂ |
| 267 | phenyl | phenyl | H | 2 | 3 | —CH₂—C(O)—NH—CH₂CH₃ |
| 268 | phenyl | phenyl | H | 2 | 3 | —CH₂—C(O)—NH—CH(CH₃)₂ |
| 269 | phenyl | phenyl | H | 2 | 3 | —CH₂—C(O)—(thiomorpholin-4-yl) |
| 270 | phenyl | phenyl | H | 2 | 3 | —CH₂—C(O)—N[(CH₂)₅CH₃]₂ |
| 271 | phenyl | phenyl | H | 2 | 3 | —CH₂—C(O)—N[(CH₂)₂CH₃]₂ |
| 272 | phenyl | phenyl | H | 2 | 3 | —CH₂—C(O)—NH—CH₂—C(O)—OCH₃ |

TABLE 1.1-continued

| Compound No. | R¹ | R² | R³ | j | k | R⁴ |
|---|---|---|---|---|---|---|
| 273 | —C₆H₅ | —C₆H₅ | H | 2 | 3 | —CH₂—C(O)—NH—CH₂—C(O)—NH₂ |
| 274 | —C₆H₅ | —C₆H₅ | H | 2 | 3 | —CH₂—C(O)—NH—CH₂—C(O)—OC(CH₃)₃ |
| 275 | —C₆H₅ | —C₆H₅ | H | 2 | 3 | —CH₂—C(O)—NH—CH(C₆H₅)—CH₂OH |
| 276 | —C₆H₅ | —C₆H₅ | H | 2 | 3 | —CH₂—C(O)—NH—(2-hydroxyindan-1-yl) |
| 277 | —C₆H₅ | —C₆H₅ | H | 2 | 3 | —CH₂—C(O)—NH—CH₂—CHOH—(4-hydroxyphenyl) |
| 278 | —C₆H₅ | —C₆H₅ | H | 2 | 3 | —CH₂—C(O)—NH—CH₂—CHOH—(3-hydroxyphenyl) |
| 279 | —C₆H₅ | —C₆H₅ | H | 2 | 3 | —CH₂—C(O)—NH—CH(CH₂OCH₃)—CHOH—C₆H₅ |
| 280 | —C₆H₅ | —C₆H₅ | H | 2 | 3 | —CH₂—C(O)—NH—CH(CH₃)—CHOH—C₆H₅ |

TABLE 1.1-continued
| Compound No. | R¹ | R² | R³ | j | k | R⁴ |
|---|---|---|---|---|---|---|
| 281 | 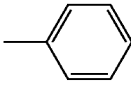 | 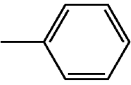 | H | 2 | 3 | 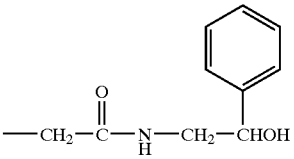 |
| 282 | 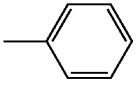 | 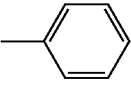 | H | 2 | 3 | 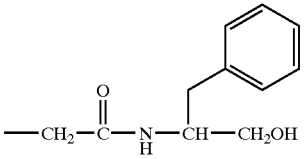 |
| 283 | 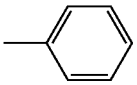 | 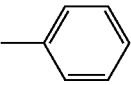 | H | 2 | 3 | 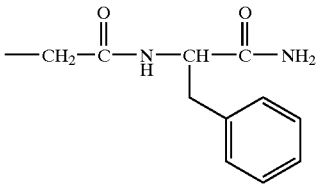 |
| 284 | 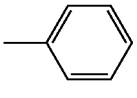 | 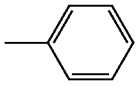 | H | 2 | 3 | 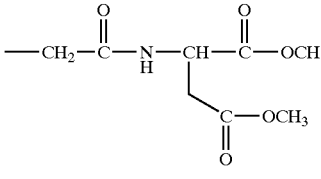 |
| 285 | 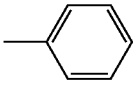 | 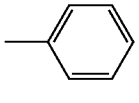 | H | 2 | 3 | 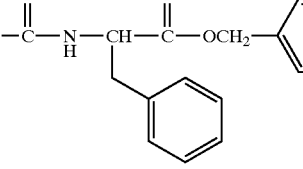 |
| 286 | 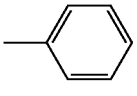 | 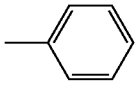 | H | 2 | 3 | 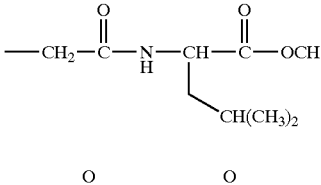 |
| 287 | 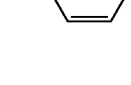 | 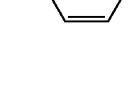 | H | 2 | 3 | 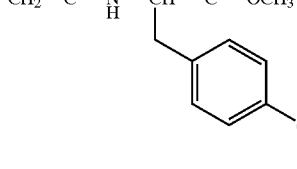 |
| 288 | 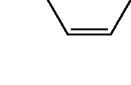 | 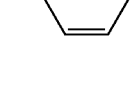 | H | 2 | 3 | 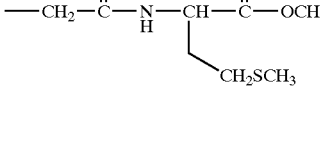 |

TABLE 1.1-continued
| Compound No. | R¹ | R² | R³ | j | k | R⁴ |
|---|---|---|---|---|---|---|
| 289 | 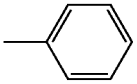 | 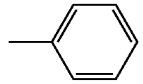 | H | 2 | 3 | 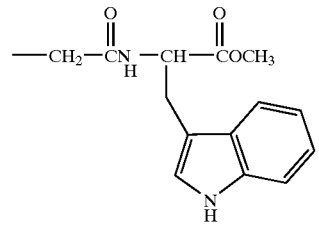 |
| 290 | 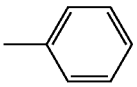 | 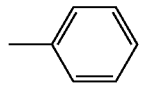 | H | 2 | 3 | 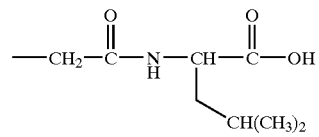 |
| 291 | 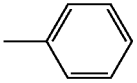 | 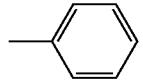 | H | 2 | 3 | 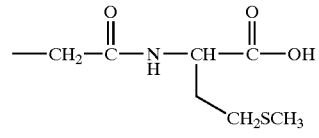 |
| 292 | 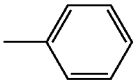 | 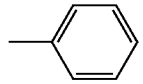 | H | 2 | 3 | 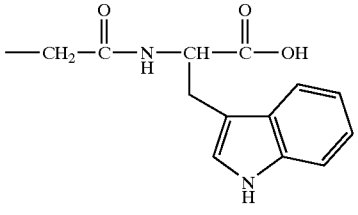 |
| 293 | 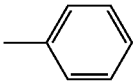 | 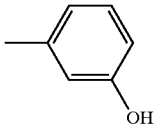 | OH | 2 | 3 | 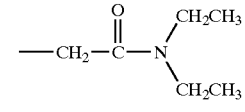 |
| 294 | 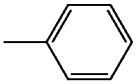 | 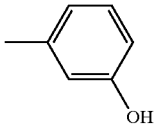 | OH | 2 | 3 | 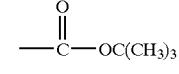 |
| 295 | 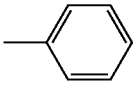 | 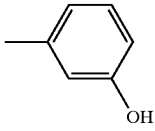 | OH | 2 | 3 | —H |
| 296 | 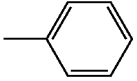 | 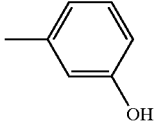 | OH | 2 | 3 | 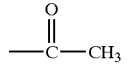 |

TABLE 1.1-continued

| Compound No. | R¹ | R² | R³ | j | k | R⁴ |
|---|---|---|---|---|---|---|
| 297 | phenyl | phenyl | H | 2 | 3 | —CH₂—C(=O)—N(H)—N(H)—C(=O)—N(phenyl)₂ |
| 298 | phenyl | phenyl | H | 2 | 3 | —CH₂—C(=O)—N(H)—CH(CH₂OH)—CH₂OH |
| 299 | phenyl | phenyl | H | 2 | 3 | —CH₂—C(=O)—N(H)—CH(phenyl)—CH(phenyl)OH |

The present invention can also use acid adducts of the cyclic diamine derivatives where such acids include, for example, mineral acids such as hydrochloric acid, hydrobromic acid, sulfuric acid, phosphoric acid, carbonic acid, and the like, as well as organic acids such as citric acid, malic acid, tartaric acid, fumaric acid, methanesulfonic acid, trifluoroacetic acid, and the like.

The present invention may use racemates and all possible optically active forms of the cyclic diamine derivatives represented by the above formula [I] or [II].

Compounds represented by the above general formula [I] and/or [II] can be synthesized by any of the general preparations given below.

(Preparation 1)

A preparation which call for treating one equivalent of a cyclic diamine derivative represented by the formula [III] below:

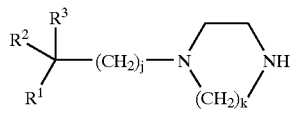

[III]

[where $R^1$, $R^2$, $R^3$, j, and k are as defined respectively in the above formula [I] or [II]] with 0.1–10 equivalents of a compound represented by the formula [IV] below:

$$X^1—R^4 \quad [IV]$$

[wherein $R^4$ is the same as defined for the $R^4$ in the above formula [I] or [II]; $X^1$ is a halogen atom, alkylsulfonyloxy group, or arylsulfonyloxy group. $R^4$ is not a group represented by the formula: —$A^2$—$R^{11}$ in where $A^2$ and $R^{11}$ are the same as defined respectively in the above formula [I] or [II]], either in absence or presence of solvent;

alternatively treating 1 equivalent of a cyclic diamine given by the formula [V] below:

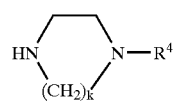

[V]

[where $R^4$ and k are the same as defined respectively in the above formula [I] or [II]], with 0.1–10 equivalents of a compound represented by the formula [VI] below:

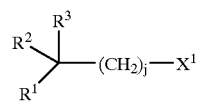

[VI]

[where $R^1$, $R^2$, $R^3$, and j are the same as defined respectively in the above formula [I] or [II]; $X^1$ represents a halogen atom, alkylsulfonyloxy, or arylsulfonyloxy group] either in the absence or presence of solvent.

Such reactions can be more smoothly run if a base is present. The base which may be used includes inorganic salts such as potassium carbonate, sodium carbonate, sodium hydrogencarbonate, and the like, or amines such as triethylamine, diisopropylethylamine, and pyridine, and the like. In addition, the reactions in these preparations can also be promoted by iodide such as potassium iodide, sodium iodide, or the like.

$X^1$ in the above formulas [IV] and [VI] represents a halogen atom, alkylsulfonyloxy, or arylsulfonyloxy group. Such halogen atoms include preferably chlorine, bromine, and iodine atoms. Suitable specific examples for the alkylsulfonyloxy groups include methylsulfonyloxy and trifluoromethylsulfonyloxy group and the like. A preferred specific example for the arylsulfonyloxy group includes a tosyloxy group.

(Preparation 2)

A preparation which calls for treating 1 equivalent of a cyclic diamine derivative represented by the above formula [III] with 0.1–10 equivalents of a carboxylic acid, sulfonic acid represented by the formula [VII] below:

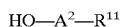     [VII]

[where $R^{11}$ and $A^3$ are the same as defined respectively in the above formulas [I] or [II]], or its reactive derivative, either in the absence or presence of solvent.

The reactive derivatives for the carboxylic acids or sulfonic acids in the above formula [VII] include highly reactive carboxylic or sulfonic acid derivatives, which are usually used in synthetic organic chemistry, such as acid halides, acid anhydrides, mixed acid anhydrides. If esters are used, the reaction can be run smoothly by activating the cyclic diamine derivative represented by the above general formula [III], for example, by using triethylaluminum.

Such reactions can be more smoothly run by using suitable amounts of a dehydrating agent such as molecular sieve, condensing agents such as dicyclohexyl carbodiimide, N-ethyl-N'-(3-dimethylaminopropyl)carbodiimide, carbonyldiimidazole, and the like, or bases similar to those used in the above preparation 1.

(Preparation 3)

A preparation which calls for treating 1 equivalent of a cyclic diamine represented by the above formula [III], with 0.1–10 equivalents of an aldehyde represented by the formula [VIII] below:

     [VIII]

[where in the formula $R^{17}$ represents either $R^7$, $R^{17}$, or $R^{20}$ of the above formula [I] or [II]; z represents an integer of 0–3], either in the absence or the presence of solvent under reductive conditions, or else treating 1 equivalent of a compound represented by the above formula [V] with 0.1–10 equivalents of an aldehyde represented by the formula [IX] below:

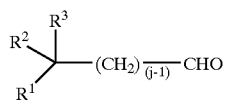     [IX]

[where in the formula $R^1$, $R^2$, $R^3$, and j are the same as defined respectively in the above formulais [I] or [II]], either in the absence or presence of solvent under reductive conditions.

Such reactions are in general called reductive amination reactions and such reductive conditions may be generated by catalytic hydrogenation using a catalyst containing a metal such as palladium, platinum, nickel, rhodium, or the like, using complex hydrides such as lithium aluminum hydride, sodium borohydride, sodium cyanoborohydride, sodium triacetoxyborohydride, and the like, boranes, or electrolytic reduction, and the like.

(Preparation 4)

A preparation which calls for treating 1 equivalent of a cyclic diamine derivative represented by the formula [X] below:

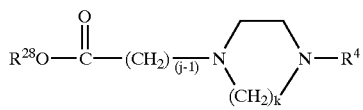     [X]

[where in the formula j, k, and $R^4$ are the same as defined respectively for the above formula [I] or [II] and $R^{28}$ represents a $C_1$–$C_6$ lower alkyl group] or 1 equivalent of a cyclic diamine derivative represented by the formula [XI] below:

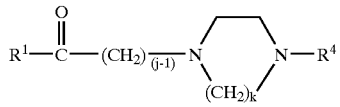     [XI]

[where $R^1$, j, k, and $R^4$ are the same as defined respectively for the above formula [I] or [II]], with 0.1–10 equivalents of an organometallic reagent represented by the formula [XII] below:

     [XII]

[wherein the formula $R^{29}$ is the same as defined for the $R^1$ and $R^2$ in the above formula [I] or [II]; M is a metal atom or its halide or complex] in the presence of solvent.

The organometallic reagents used in such preparations may be those suitably selected organometallic reagents known to cause a nucleophilic reaction toward esters and/or ketones in general in synthetic organic chemistry, such as Grignard reagents (M=MgX$^2$), organolithium reagents (M=Li), organocerium reagents (M=CeX$_2^2$,) (X$^2$ represents a halogen atom). These organometallic reagents may be prepared by known methods from the corresponding halides. The halides preferably include chlorides, bromides, iodides.

If the substrates submitted to each of the above preparations contains a substituent which reacts under each reaction condition in general in synthetic organic chemistry or is thought to adversely affect the reaction, that functional group can be protected by a known suitable protecting group followed by the reaction of the above preparations and deprotection using a known procedure to ado obtain the desired compound.

Each of the above preparations may use solvents for the reaction such as halogenated hydrocarbons such as dichloromethane, chloroform, or the like, aromatic hydrocarbons such as benzene, toluene, and the like, ethers such as diethyl ether, tetrahydrofuran, or the like, esters such as ethyl acetate, aprotic polar solvents such as dimethylformamide, dimethyl sulfoxide, acetonitrile, and the like, alcohols such as methanol, ethanol, isopropyl alcohol, and the like.

The reaction temperature in either of the preparations should be in the range of −78–+150° C., preferably 0° C.–100° C. After completion of the reaction, the usual isolation and purification operations such as concentration, extraction, recrystallization, chromatography, and the like may be used, to isolate the desired cyclic diamine derivatives represented by the above formula [I] or [II]. These can be converted into pharmacologically acceptable acid adducts by the usual method.

Potential Industrial Utilities

The chemokine receptor antagonist, which contain the cyclic diamine derivative or its pharmacologically acceptable acid adducts of this invention, which inhibits chemokines such as MIP-1α and/or MCP-1 and the like from action on target cells, are useful as therapeutic agents and/or preventive preparation for diseases such as atherosclerosis, rheumatic arthritis, psoriasis, asthma, ulcerative colitis, glomerulonephritis, multiple sclerosis, pulmonary fibrosis, myocarditis, and the like, in which tissue infiltration of blood monocytes, lymphocytes, and the like plays a major role in the initiation, progression, and maintenance of the disease.

EXAMPLES

The present invention is now specifically described by the following examples. However, the present invention is not limited to these compounds described in these examples. Compound numbers in these examples represent numbers attached to these compounds listed as suitable specific examples in Tables 1.1–1.18.

Example 1

Synthesis of 1-(3,3-Diphenylpropyl)-4-(4-nitrobenzyl)homopiperazine (Compound No. 23)

A mixture of 120 mg of homopiperazine, 206 mg of homopiperazine dihydrochloride, and 3 mL of ethanol was heated to 70° C. to prepare a solution. 375 mg of sodium iodide and 287 mg of 3,3-diphenylpropyl methanesulfonate were added sequentially to the solution and the mixture was stirred at 70° C. for 14 hours. The mixture was allowed to cool to room temperature and the ethanol was removed under reduced pressure, followed by adding 20 mL of 2N aqueous sodium hydroxide solution and extracting with 20 mL×2 of ethyl acetate. The organic layers were combined, washed with 20 mL of saturated aqueous sodium chloride, dried over anhydrous magnesium sulfate, filtered, and concentrated to give 1-(3,3-diphenylpropyl)homopiperazine.

The resulting 1-(3,3-diphenylpropyl )homopiperazine was dissolved in 3 mL of acetonitrile followed by adding 213 mg of 4-nitrobenzyl bromide and 144 mg of potassium carbonate. The mixture was stirred at 70° C. for 14 hours and allowed to cool to room temperature and the solvent was removed under reduced pressure. 20 mL of aqueous 2N sodium hydroxide was added and the mixture was extracted with 20 mL×2 of ethyl acetate. The organic layers were combined, washed with 20 mL of saturated aqueous sodium chloride, dried over anhydrous magnesium sulfate, filtered, concentrated, and purified by column chromatography (silica gel, ethyl acetate) to obtain 255 mg of the titled compound. This was treated with a hydrogen chloride solution in ether and the solvent was removed under reduced pressure; and the residue was dried to obtain the hydrochloride salt of the titled compound.

Compound No. 23 (Free Base) had the following $^1$H NMR (CDCl$_3$, 270 MHz) δ (ppm): 1.73–1.82 (m, 2H), 2.16–2.25 (m, 2H), 2.40–2.46 (m, 2H), 2.64–2.71 (m, 8H), 3,71 (s, 2H), 4.01 (t, J=7.6 Hz, 1H), 7.13–7.19 (m, 2H), 7.19–7.31 (m, 8H), 7.50 (d, J=8.6 Hz, 2H), 8.16 (d, J=8.6 Hz, 2H).

Example 2

Preparation of 1-Benzyl-4-(3,3-diphenylpropyl) homopiperazine (Compound No. 15)

A mixture of 101 mg of homopiperazine, 175 mg of homopiperazine dihydrochloride, 3 mL of ethanol was heated to 70° C. into a solution. 0.115 mL of benzyl chloride was added and the mixture was stirred at 70° C. for 3 hours. After cooling to room temperature, ethanol was removed under reduced pressure, and 20 mL of aqueous 2N sodium hydroxide solution was added to the solution, which was extracted with 20 mL×2 of ethyl acetate. The organic layers were combined, washed with 20 mL of saturated aqueous sodium chloride, dried over anhydrous magnesium sulfate, filtered, and concentrated to give 1-benzyihomopiperazine.

The resulting benzyihomopiperazine was dissolved in 3 mL of ethanol, to which were added 296 mg of 3,3-diphenylpropyl methanesulfonate and 136 mg of potassium carbonate. The mixture was stirred at 70° C. for 15 hours and it was cooled to room temperature and the solvent was removed under reduced pressure. 20 mL of aqueous 2N sodium hydroxide was added and the solution was extracted with 20 mL×2 of ethyl acetate. The organic layers were combined and washed with 20 mL of saturated aqueous sodium chloride, dried over anhydrous magnesium sulfate, filtered, concentrated, and purified by column chromatography (silica gel, ethyl acetate) to obtain 135 mg of the titled compound. This was treated with a hydrogen chloride solution in ether followed by removing the solvent under reduced pressure and drying to give the hydrochloride salt of the titled compound.

Compound No. 15 (free base) had the following $^1$H NMR (CDCl$_3$, 270 MHz) δ (ppm): 1.71–1.81 (m, 2H), 2.16–2.25 (m, 2H), 2.39–2.45 (m, 2H), 2.64–2.73 (m, 8H), 3,62 (s, 2H), 4.01 (t, J=7.9 Hz, 1H), 7.12–7.34 (m, 15H).

Example 3

Preparation of 1-Benzoyl-4-(3,3-diphenylpropyl) homopiperazine (Compound No. 199)

A mixture of 126 mg of homopiperazine. 218 mg of homopiperazine dihydrochloride, 3 mL of ethanol was heated to 70° C. into a solution. 378 mg of sodium iodide and 289 mg of 3,3-diphenylpropyl methanesulfonate were added sequentially to the solution and the solution was stirred at 70° C. for 15 hours. After the solution was cooled to room temperature, the ethanol was removed under reduced pressure followed by adding 20 mL of aqueous 2N sodium hydroxide and extracting with 20 mL×2 of ethyl acetate. The organic layers were combined, washed with 20 mL of saturated aqueous sodium chloride, dried over anhydrous magnesium sulfate, filtered, and concentrated to give 1-(3,3-diphenylpropyl)homopiperazine.

The resulting 1-(3,3-diphenylpropyl )homopiperazine was dissolved in 3 mL of dichloromethane, followed by adding 107 mg of triethylamine and 140 mg of benzoyl chloride. After the mixture was stirred at room temperature for 6 hours, it was mixed with 20 mL of aqueous 2N sodium hydroxide and extracted with 20 mL×2 of ethyl acetate. The organic layers were combined, washed with 20 mL of saturated aqueous sodium chloride, dried over anhydrous magnesium sulfate, filtered, concentrated, and purified by column chromatography (silica gel, hexane/ethyl acetate 4:6) to obtain 249 mg of the titled compound. This was treated with a hydrogen chloride solution in ether and the solvent was removed under reduced pressure and the residue was dried to give the hydrochloride salt of the titled compound.

Compound No. 199 (free base) had the following $^1$H NMR (CDCl$_3$, 270 MHz) δ (ppm): 1.69–1.79 (m, 1H), 1.90–1.99 (m, 1H), 2.12–2.28 (m, 2H), 2.35–2.48 (m, 2H), 2.54–2.61 (m, 2H), 2.64–2.69 (m, 1H), 2.75–2.30 (m, 1H), 3.39–3.46 (m, 2H), 3.73–3.78 (m, 2H), 3,96–4.06 (m, 1H), 7.13–7.31 (m, 10H), 7.35–7.39 (m, 5H).

Example 4

Preparation of 1-[4-(Dimethylaminomethyl) benzoyl]-4-(3,3-diphenylpropyl)homopiperazine (Compound No. 202)

The same method as that of Example 1 was used to obtain 1-(3,3-diphenylpropyl)homopiperazine.

The resulting 1-(3,3-diphenylpropyl)homopiperazine was dissolved in 3 mL of toluene under argon, followed by adding 0.65 mL of a 15% trimethylaluminum solution in hexane. The mixture was stirred at room temperature for 15 minutes, mixed with 187 mg of methyl 4-(dimethylaminomethyl)benzoate, stirred at 60° C. for 22 hours. The mixture was cooled to room temperature, mixed with 2N hydrochloric acid, and stirred. 20 mL of aqueous 2N sodium hydroxide was added and the mixture was extracted with 20 mL×2 of ethyl acetate. The organic layers were combined, washed with 20 mL of saturated aqueous sodium chloride, dried over anhydrous magnesium sulfate, filtered, concentrated, and purified by column chromatography (silica gel, ethyl acetate/methanol 6:4) to obtain 234 mg of the titled compound. This was treated with a hydrogen chloride solution in ether, the solvent was removed under reduced pressure and the residue was dried to give the hydrochloride salt of the titled compound.

Compound No. 202 (free base) had the following $^1$H NMR (CDCl$_3$, 270 MHz) δ (ppm): 1.65–1.80 (m, 1H), 1.89–2.01 (m, 1H), 2.12–2.29 (m, 2H), 2.24 (s, 6H), 2.35–2.48 (m, 2H), 2.52–2.60 (m, 2H), 2.60–2.70 (m, 1H), 2.74–2.79 (m, 1H), 3,40–3.48 (m, 2H), 3.43 (s, 2H), 3.32–3.77 (m, 2H), 3.96–4.06 (m, 1H), 7.16–7.52 (m, 14H).

Example 5

Preparation of 1-(3,3-Diphenylpropyl)-4-(2-quinolylmethyl)homopiperazine (Compound No. 237)

The same method as that of Example 1 was used to obtain 1-(3,3-diphenylpropyl)homopiperazine.

The resulting 1-(3,3-diphenylpropyl)homopiperazine was dissolved in 3 mL of ethanol, mixed with 228 mg of 2-(chloromethyl)quinoline hydrochloride and 141 mg of potassium carbonate, and stirred at 70° C. for 14 hours. The mixture was cooled to room temperature and the ethanol was removed under reduced pressure, 20 mL of aqueous 2N sodium hydroxide was added and the mixture was extracted with 20 mL×2 of ethyl acetate. The organic layers were combined, washed with 20 mL of saturated aqueous sodium chloride, dried over anhydrous magnesium sulfate, filtered, concentrated, and purified by column chromatography (silica gel, ethyl acetate/methanol 95:5), to obtain 109 mg of the titled compound. This was treated with a hydrogen chloride solution in ether and the solvent was removed under reduced pressure and the residue was dried to give the hydrochloride salt of the titled compound.

Compound No. 237 (free base) had the following $^1$H NMR (CDCl$_3$, 270 MHz) δ (ppm): 1.76–1.86 (m, 2H), 2.18–2.27 (m, 2H), 2.42–2.49 (m, 2H), 2.68–2.82 (m, 8H), 3.96 (s, 2H), 4.02 (t, J=7.6 Hz, 1H), 7.12–7.31 (m, 1H), 7.50 (dd, j=7.9, 7.9 Hz, 1H), 7.65–7.72 (m, 2H), 7.79 (d, J=7.9 Hz, 1H), 8.05 (d, J=8.3 Hz, 1H), 8.11 (d, J=8.6 Hz, 1H).

Example 6

Preparation of 1-(3,3-Diphenylpropyl)-4-(7-methoxy-2H-chromene-2-one-4-ylmethyl) homopiperazine (Compound No. 206)

The same method as that of Example 5 was used except for the use of 70 mg of 4-(bromomethyl)-7-methoxy-2H-chromene-2-one to give 303 mg of the titled compound, and except for the use of ethanol/chloroform as the solvent for the reaction. Furthermore, the same method as that of Example 5 was used to obtain the hydrochloride salt of the titled compound, Compound No. 206 (free base) had the following $^1$H NMR (CDCl$_3$, 270 MHz) δ (ppm): 1.75–1.85 (m, 2H), 2.16–2.25 (m, 2H), 2.39–2.45 (m, 2H), 2.62–2.79 (m, 8H), 3.72 (s, 2H), 3.87 (s, 3H), 4.02 (t, J=7.6 Hz, 1H), 6.36 (s, 1H), 6.80–6.85 (m, 2H), 7.12–7.31 (m, 10H), 7.75 (d, J=9.6 Hz, 1H).

Example 7

Preparation of 1-(2-Benzimidazolylmethyl)-4-(3,3-diphenylpropyl)homopiperazine (Compound No. 207)

The same method as that of Example 5 was used except for the use of 165 mg of 2-(chloromethyl)benzimidazole and 16 mg of sodium iodide to promote the reaction to give 91 mg of the titled compound, Furthermore, the same method as that of Example 5 was used to obtain the hydrochloride salt of the titled compound.

Compound No. 207 (free base) had the following $^1$H NMR (CDCl$_3$, 270 MHz) δ (ppm): 1.70–1.82(m, 2H), 2.19–2.29 (m, 2H), 2.43–2.50 (m, 2H), 2.65–2.73 (m, 4H), 2.76–2.81 (m, 4H), 3.96 (s, 2H), 3.99 (t, J=7.6 Hz, 1H), 7.14–7.31 (m, 14H), 7.60–7.85 (m, 1H).

Example 8

Preparation of 1-(2,2-Diphenylethyl)-4-[4-(methylsulfonyl)benzyl]homopiperazine (Compound No. 6)

A mixture of 120 mg of homopiperazine, 216 mg of homopiperazine dihydrochloride salt, 3 mL of ethanol was heated to 70° C. into a solution. To this solution were added sequentially 383 mg of sodium iodide and 250 mg of 4-(methylsulfonyl)benzyl bromide, followed by stirring at 70° C. for 14 hours. After the solution was cooled to room temperature, ethanol was removed under reduced pressure and 20 mL of aqueous 2N sodium hydroxide was added and the mixture was extracted with 20 mL×2 of ethyl acetate. The organic layers were combined, washed with 20 mL of aqueous saturated sodium chloride, dried over anhydrous magnesium sulfate, filtered, and concentrated to give 176 mg of 1-[4-(methylsulfonyl)benzyl]homopiperazine.

The resulting 1-[4-(methylsulfonyl)benzyl]homopiperazine was dissolved in 5 mL of dichloromethane, followed by adding 223 mg of diphenylacetaldehyde and 217 mg of sodium triacetoxyborohydride. After the mixture was stirred at room temperature for 16 hours, it was mixed with 30 mL of aqueous saturated sodium hydrogencarbonate, and extracted with 30 mL×2 of ethyl acetate. The organic layers were combined, washed with 30 mL of saturated aqueous sodium chloride, dried over anhydrous magnesium sulfate, filtered, concentrated, and purified by column chromatography (silica gel, ethyl acetate) to obtain 173 mg of the titled compound. This was treated with a hydrogen chloride solution in ether and the solvent was removed under reduced pressure, the residue was dried to give the hydrochloride salt of the titled compound.

Compound No. 6 (free base) had the following $^1$H NMR (CDCl$_3$, 270 MHz) δ (ppm): 1.64–1.77 (m, 2H), 2.51–2.64 (m, 4H), 2.67–2.83 (m, 4H), 3.04 (S, 3H), 3.15 (d, J=7.6 Hz, 2H), 3.61 (s, 2H), 4.14 (t, J=7.6 Hz, 1H), 7.13–7.35 (m, 10H), 7.45 (d, J=8.2 Hz, 2H), 7.84 (d, J=8.2 Hz, 2H).

Example 9

Preparation of 1-(3-Hydroxy-3,3-diphenylpropyl)-4-(4-chlorobenzyl)homopiperazine (Compound No. 107)

A solution of 54 mg of methyl $^3$-[4-(4-chlorobenzyl) homopiperazinyl]propionate in 10 mL of ether was mixed with under nitrogen, 4 mL of 1 M phenyl magnesium bromide. The mixture was stirred at room temperature for 30 minutes, mixed with aqueous saturated ammonium chloride and the mixture was extracted with 50 mL of ethyl acetate. The extract was washed with 50 mL of saturated aqueous sodium chloride, dried over anhydrous sodium sulfate, filtered, concentrated, and purified by column chromatography (silica gel, ethyl acetate/methanol 9:1) to give 65 mg of the titled compound. This was treated with a hydrogen chloride solution in ether and the solvent was removed under reduced pressure and the residue was dried to give the hydrochloride salt of the titled compound.

Compound 107 (free base) had the following $^1$H NMR (CDCl$_3$, 270 MHz) δ (ppm): 1.77–1.86 (m, 2H), 2.36–2.40 (m, 2H), 2.54–2.71 (m, 10H), 3.58 (s, 2H), 7.15–7.20 (m, 2H), 7.26–7.32 (m, 8H), 7.44–7.48 (m, 4H).

Example 10

Preparation of 1-(3,3-Diphenylpropyl)-4-(4-carbamoylbenzyl)homopiperazine (Compound No. 55)

A 20 mL solution of 175 mg of compound No. 30 in 20 mL of t-butyl alcohol was mixed with 570 mg of ground potassium hydroxide and the mixture was refluxed for 2.5 hours. The solution was cooled to room temperature and mixed with 50 mL of water and 100 mL of ethyl acetate. The organic layer was separated and the aqueous layer was extracted with 50 mL of ethyl acetate. The organic layers were combined, dried over anhydrous sodium sulfate, filtered, concentrated, and purified by column chromatography (silica gel, ethyl acetate/methanol 4:1) to give 91 mg of the titled compound. This was treated with a hydrogen chloride solution in ether and the solvent was removed under reduced pressure and the residue was dried to give the hydrochloride salt of the titled compound.

Compound No. 55 (free base) had the following $^1$H NMR (CDCl$_3$, 270 MHz) δ (ppm): 0.86–0.91 (m, 1H), 1.23–1.28 (m, 2H), 1.73–1.82 (m, 2H), 2.18–2.26 (m, 2H), 2.42–2.47 (m, 2H), 2.65–2.73 (m, 6H), 3.67 (s, 2H), 5.6–6.2 (brs, 2H), 7.13–7.30 (m, 10H), 7.41 (d, 2H, J=8.25 Hz), 7.75 (d, 2H, J=8.25 Hz).

Example 11

Preparation of 1-[3,3-Di(2-furyl)-3-hydroxypropyl]-4-[4-(methylsulfonyl)benzyl]homopiperazine (Compound No. 129)

To a solution of 2-furyl lithium prepared in 50 mL of THF using 3 mL of furan and 2 mL of 1.63 M n-butyllithium was added dropwise at 0° C., a 10 ml solution in THF of 99 mg of methyl 3-[4-{4-(methylsulfonyl) benzyl}homopiperazinyl]propionate. After stirring at 0° C. for 1 hour, the mixture was mixed with 50 mL of an aqueous saturated ammonium chloride, and extracted with 50 mL×2 of ethyl acetate. The extracts were combined, dried over anhydrous sodium sulfate, filtered, concentrated, and purified by column chromatography (silica gel, ethyl acetate) to give 62 mg of the titled compound.

Compound No. 129 had the following $^1$H NMR (CDCl$_3$, 270 MHz) δ (ppm): 1.80–1.89 (m, 2H), 2.32–2.36 (m, 2H), 2.56–2.60 (m, 2H), 2.74–2.78 (m, 2H), 2.66–2.70 (m, 6H), 3.05 (s, 3H), 3,70 (s, 2H), 6.30–6.34 (m, 4H), 7.36–7.37 (m, 2H), 7.55 (d, 2H J=8.25 Hz), 7.86 (d, 2H, J=8.25 Hz).

Example 12

Preparation of 1-[3,3-bis(4-Hydroxyphenyl)-3-hydroxypropyl]-4-[4-(methylsulfonyl)benzyl] homopiperazine (Compound No. 119)

To a 2.0 mL anhydrous THF solution of 120 mg of methyl 3-[4-(4-chlorobenzyl)homopiperazinyl]propionate was added under nitrogen, 2.0 mL solution in THF of 1.5 mmol of 4-(tert-butyldimethylsilyloxy)phenyl magnesium bromide. The mixture was stirred at room temperature for 30 minutes and an aqueous saturated ammonium chloride solution was added and the mixture was extracted with 20 mL×3 of ethyl acetate. The extracts were washed with aqueous saturated sodium chloride, dried over anhydrous sodium sulfate, filtered, concentrated, and purified by column chromatography (silica gel, hexane/ethyl acetate 1:1) to give 33 mg of a silyl protected form of the titled compound. The resulting oily product was dissolved in 3 mL of THF and mixed with 0.8 mL of a 1N THF solution of tributylammonium fluoride. The mixture was stirred at room temperature for 4 hours, mixed with aqueous saturated ammonium chloride and extracted with 20 mL×3 of ethyl acetate. The extracts were washed with aqueous saturated sodium chloride, dried over anhydrous sodium sulfate, filtered, concentrated, and purified by column chromatography to obtain 5 mg of the titled compound.

Compound No. 119 had the following $^1$H NMR (CDCl$_3$, 270 MHz) δ (ppm): 1.81–1.94 (m, 2H), 2.35 (broad s, 3H), 2.55–2.82 (m, 1H), 3.08 (s, 3H), 3.70 (s, 2H), 6.67 (d, J=8.6 Hz, 4H), 7.14 (d, J=8.9 Hz, 4H), 7.48 (d, J=8.3 Hz, 2H), 7.81 (d, J=8.3 Hz, 2H).

Example 13

Preparation of 1-[3-Hydroxy-3-(1-methyl-2-pyrrolyl)-3-phenylpropyl]-4-[4-(methylsulfonyl) benzyl]homopiperazine (Compound No. 136)

1.0 mL of an anhydrous THF solution of 121 mg of methyl 3-[4-{4-(methylsulfonyl)benzyl}homopiperazinyl] propionate was added under nitrogen to 6 mL of a THF solution of 1.5 mmol of 1-methyl-2-pyrrolyl cerium dichloride at −78° C. After stirring at −78° C. for 3 hours, the mixture was mixed with 20 mL of water and it was filtered from insoluble matter using Celite, followed by extracting the filtrate with 30 mL×2 of ethyl acetate. The extracts were dried over anhydrous sodium sulfate, filtered, concentrated, and purified by column chromatography (silica gel, ethyl acetate, ethyl acetate/methanol 10:1) to give 7 mg of the titled compound.

Compound No. 136 had the following $^1$H NMR (CDCl$_3$, 270 MHz) δ (ppm): 7.88 (d, J=8.4 Hz, 2H), 7.56 (d, J=8.4 Hz, 2H), 7.32–7.16 (m, 5H), 6.48–6.47 (m, 1H), 6.22–6.20 (m, 1H), 6.06–6.04 (m, 1H), 3.72 (s, 2H), 3.26 (s, 3H), 3.06 (s, 3H), 2.87–2.39 (m, 11H), 2.05–1.83 (m, 3H).

Example 14

Preparation of 1-[3,3-bis(1-methyl-2-pyrrolyl)-3-hydroxypropyl]-4-[4-(methylsulfonyl)benzyl] homopiperazine (Compound No. 127)

2.0 mL of an anhydrous THF solution of 160 mg of 1-[4-(methylsulfonyl)benzyl]-4-(3-oxo-3-phenylpropyl)

homopiperazine was added under nitrogen at −78° C. to a 3 mL THF solution of 0.8 mmol of 1-methyl-2-pyrrolylcerium dichloride. The mixture was stirred at −78° C. for 3 hours and then it was mixed with 20 mL of water and filtered from insolubles, using Celite; the filtrate was extracted with 30 mL×2 of ethyl acetate. The extracts were dried over anhydrous sodium sulfate, filtered, concentrated, and purified by column chromatography (silica gel, hexane/ethyl acetate 1:3, ethyl acetate) to give 18 mg of the titled compound.

Compound No. 127 had the following $^1$H NMR (CDCl$_3$, 270 MHz) δ (ppm): 7.88 (d, J=8.3 Hz, 2H), 7.56 (d, J=8.3 Hz, 2H), 6.50–6.48 (m, 2H), 6.24–6.22 (m, 2H), 6.03–6.00 (m, 2H), 3.71 (s, 2H), 3.21 (s, 6H), 3.05 (s, 3H), 2.8–2.62 (m, 10H), 2.36–2.32 (m, 2H), 1.88–1.83 (m, 2H).

Example 15

Preparation of 1-(3,5-Difluorophenyl)-3-hydroxy-3-(3-hydroxyphenyl)propyl-4-[4-(methylsulfonyl)benzyl]homopiperazine (Compound No. 138)

To 1.0 mL anhydrous THF solution of 263 mg of 1-[4-(methylsulfonyl)benzyl]-4-[3-oxo-3-{3-(tert-butyldimethylsilyloxy)phenyl}propyl]homopiperazine was added 3 mL of a THF solution of 2.5 mmol of 3,5-difluorophenylmagnesium bromide under nitrogen at 0° C. The mixture was stirred at room temperature for 3 hours, and aqueous saturated ammonium chloride was added and the mixture was extracted with 40 mL×2 with ethyl acetate. The extracts were combined, dried over anhydrous sodium sulfate, filtered, concentrated, and purified by column chromatography (silica gel, ethyl acetate, ethyl acetate/methanol 10:1) to obtain 11 mg of a silyl protected form of the titled compound.

The resulting oil was dissolved in 5 mL of THF and mixed with 0.07 mL of a THF solution of 1 M tetrabutylammonium fluoride. The mixture was stirred at room temperature for 30 minutes and mixed with 20 mL of water and extracted with 30 mL×3 of ethyl acetate. The extracts were combined, dried over anhydrous sodium sulfate, filtered, concentrated, and purified by column chromatography (silica gel, ethyl acetate) to give 11 mg of the titled compound.

Compound No. 138 had the following $^1$H NMR (CDCl$_3$, 270 MHz) δ (ppm): 7.88 (d, J=8.3 Hz, 2H), 7.54 (d, J=8.3 Hz, 2H), 7.18 (t, J=7.9 Hz, 1H), 7.02–6.93 (m, 4H), 6.70–6.58 (m, 1H), 3,68 (s, 2H), 3,06 (s, 3H), 2.72–2.60 (m, 10H), 2.33–2.28 (m, 2H), 1.85–1.76 (m, 2H).

Example 16

Preparation of 1-(3-(4-Hydroxyphenyl)-3-phenylpropyl]-4-[4-(methylsulfonyl)benzyl]homopiperazine (Compound No. 42)

5.0 mL solution in dichloromethane of 33 mg of 1-[3-(4-methoxyphenyl)3-phenyl propyl]-4-[4-(methylsulfonyl)benzyl]homopiperazine was cooled under nitrogen to −78° C. followed by adding 0.022 mL of boron tribromide. The mixture was gradually allowed to rise to room temperature, at which temperature the mixture was stirred for 3 hours, followed by adding 3 mL of an aqueous saturated sodium hydrogencarbonate solution and extracting with a 50 mL×2 of ethyl acetate. The extracts were combined, dried over anhydrous sodium sulfate, filtered, concentrated, and purified by column chromatography (silica gel, ethyl acetate/methanol 9:1) to obtain 12 mg of the titled compound. This was treated with a hydrogen chloride solution in ether and the solvent was removed under reduced pressure and residue was dried to give the hydrochloride salt of the titled compound.

Compound No. 42 (free base) had the following $^1$H NMR (CDCl$_3$, 270 MHz) δ (ppm): 1.75–1.8 (m, 2H), 2.15–2.3 (m, 2H), 2.4–2.9 (m, 10H), 3.04 (s, 3H), 3.68 (s, 2H), 3.82 (t, J=7.5 Hz, 1H), 6.59 (d, J=8.6 Hz, 2H), 7.1–7.3 (m, 5H), 7.51 (d, J=8.2 Hz, 2H), 7.86 (d, J=8.2 Hz, 2H).

Example 17

Preparation of 1-[3-Hydroxy-3-(3-methylainophenyl)-3-phenylpropyl]-4-[4-(methylsulfonyl)benzyl]homopiperazine (Compound No. 146)

To a solution of 34 mg of compound No. 143 in 1.2 mL of acetonitrile and 0.3 mL of water was added 14 mg of RhCl(PPh$_3$)$_3$, and the mixture was stirred at 100° C. for 2 days, After the mixture was allowed to cool to room temperature, evaporation of acetonitrile and column chromatography (silica gel, ethyl acetate) gave 9.0 mg of the titled compound.

Compound No. 146 had the following $^1$H NMR (CDCl$_3$, 270 MHz) δ (ppm): 1.79–1.91 (m, 2H), 2.34–2.41 (m, 2H), 2.55–2.75 (m, 11H), 2.80 (s, 3H), 3.05 (s, 3H), 3.70 (s, 2H), 5.40 (broad s, 1H), 6.39–6.44 (m, 1H), 6.70–6.80 (m, 2H), 7.05–7.20 (m, 2H), 7.21–7.31 (m, 3H), 7.41–7.48 (m, 2H), 7.55 (d, J=8.1 Hz, 2H), 7.78 (d, J=8.1 Hz, 2H).

Example 18

Preparation of 1-[3-(3-Acetylaminophenyl)-3-hydroxy-3-phenylpropyl]-4-[4-(methylsulfonyl)benzyl]homopiperazine (Compound No. 162)

To a solution of 352 mg of compound No. 159 in 5 mL of dichloromethane was added 190 μL of triethylamine and 130 μL of acetic anhydride. The mixture was stirred at room temperature for 2 hours. 3 mL of water was added and the mixture was extracted with dichloromethane. The extract was concentrated and purified by column chromatography (silica gel, ethyl acetate/methanol 7:3) to give 224 mg of the titled compound as a white solid.

Compound No. 162 had the following $^1$H NMR (CDCl$_3$, 270 MHz) δ (ppm): 7.88 (d, J=8.3 Hz, 2H), 7.57–7.45 (m, 5H), 7.22–7.16 (m, 6H), 3.70 (s, 2H), 3.05 (s, 3H), 2.73–2.60 (m, 10H), 2.40–2.37 (m, 2H), 1.88–1.81 (m, 2H).

Examples 19–151

The compounds of this invention were synthesized pursuant to methods of Example 1, 2, 3, 4, 5, 6, 7, 9, 11, 12, 14, 15, or 16, using the corresponding reactant respectively. The $^1$H NMR data, yields, and synthetic methods are summarized in Table 2.

TABLE 2

| | Compound No. | ¹H NMR Data (CDCl₃) δ(ppm) | Yield (%) | Synthetic method |
|---|---|---|---|---|
| Example 19 | 5 | 1.69–1.82(m, 2H), 2.58–2.70(m, 4H), 2.69(t, J=5.9Hz, 2H), 2.76(t, J=5.9Hz, 2H), 3.04(s, 3H), 3.73(s, 2H), 4.61(s, 1H), 7.11–7.21(m, 2H), 7.26(dd, J=7.3, 7.3Hz, 4H), 7.42(d, J= 7.3Hz, 4H), 7.56(d, J=8.6Hz, 2H), 7.87(d, J=8.6Hz, 2H). | 47 | Similar to Example 2 |
| Example 20 | 7 | 2.15–2.35(m, 4H), 2.35–2.60(m, 8H), 3.04(s, 3H), 3.57(s, 2H), 3.97(t, J=7.3Hz, 1H), 7.10–7.34(m, 10H), 7.53(d, J=8.3Hz, 2H), 7.88(d, J=8.3Hz, 2H), | 44 | Similar to Example 1 |
| Example 21 | 8 | 2.15–2.33(m, 4H), 2.33–2.55(m, 8H), 3.45(s, 2H), 3.96(t, J=6.9Hz, 1H), 7.10–7.33(m, 14H). | 54 | Similar to Example 1 |
| Example 22 | 16 | 1.78–1.88(m, 2H), 2.18–2.27(m, 2H), 2.42–2.49(m, 2H), 2.66–2.74(m, 4H), 2.78–2.87(m, 4H), 3.26(s, 2H), 4.03(t, J=7.6Hz, 1H), 7.07–7.37(m, 13H), 7.57(d, J=7.6Hz, 2H), 9.31(br.s, 1H). | 33 | Similar to Example 1 |
| Example 23 | 17 | 1.61–1.71(m, 2H), 2.14–2.23(m, 2H), 2.35–2.41(m, 2H), 2.45–2.65(m, 10H), 2.93(t, J=5.3Hz, 2H), 3.99(t, J=7.6Hz, 1H), 5.30(s, 1H), 7.13–7.31(m, 10H), 7.46(d, J=8.6Hz, 2H), 7.80(d, J=8.6Hz, 2H). | 21 | Similar to Example 1 |
| Example 24 | 18 | 1.67–1.77 (m, 2H), 2.12–2.24(m, 2H), 2.35–2.41(m, 2H), 2.55–2.64(m, 4H), 2.69–2.77 (m, 4H), 3.19(s, 2H), 3.98(t, J=7.6Hz, 1H), 4.47(d, J=5.9Hz, 2H), 7.13–7.35(m, 10H), 7.63(br, 1H), | 43 | Similar to Example 1 |
| Example 25 | 19 | 1.76–1.85(m, 2H), 2.19–2.28(m, 2H), 2.41–2.48(m, 2H), 2.65–2.75(m, 4H), 2.81–2.87(m, 4H), 2.96(t, J=5.9Hz, 2H), 4.00(t, J=7.6Hz, 1H), 4.06(t, J=5.9Hz, 2H), 6.88–6.97(m, 3H), 7.12–7.21(m, 2H), 7.21–7.31(m, 10H). | 51 | Similar to Example 1 |
| Example 26 | 20 | 1.68–1.78(m, 2H), 2.16–2.25(m, 2H), 2.36–2.43(m, 2H), 2.55–2.71(m, 10H), 3.28(dt, J=5.9, 5.0Hz, 2H), 3.97(t, J=7.6Hz, 1H), 5.55(br, 1H), 6.99–7.05(m, 1H), 7.13(d, J=7.34Hz, 15H). | 13 | Similar to Example 1 |
| Example 27 | 21 | 1.82–1.93(m, 2H), 2.19–2.28(m, 2H), 2.43–2.50(m, 2H), 2.68–2.81(m, 10H), 3.52(dt, J=5.6. 5.0Hz, 2H), 3.99(t, J=7.6Hz, 1H), 7.08(br, 1H), 7.14–7.31(m, 10H), 7.38–7.52(m, 3H), 7.81(d, J=6.6Hz, 2H). | 19 | Similar to Example 1 |
| Example 28 | 22 | 1.78–1.87(m, 2H), 2.21–2.30(m, 2H), 2.43–2.50(m, 2H), 2.68–2.74(m, 4H), 2.81–2.88(m, 4H), 3.44(s, 2H), 3.99(t, J=7.6Hz, 1H), 5.14(s, 2H), 7.12–7.40(m, 15H). | 25 | Similar to Example 1 |
| Example 29 | 24 | 1.73–1.83(m, 2H), 2.17–2.26(m, 2H), 2.41–2.47(m, 2H), 2.63–2.73(m, 8H), 3.72(s, 2H), 4.02(t, J=7.6Hz, 1H), 7.12–7.20(m, 2H), 7.20–7.31(m, 8H), 7.46(dd, J=7.9, 7.9Hz, 1H), 7.67(d, J=7.9Hz, 2H), 8.09(dd, J=7.9, 1.0Hz, 1H), 8.21(s, 1H). | 50 | Similar to Example 1 |
| Example 30 | 25 | 1.70–1.74(m, 2H), 2.16–2.21(m, 2H), 2.37–2.41(m, 2H), 2.54–2.57(m, 2H). 2.59–2.66(m, 6H), 3.89(s, 2H), 4.01(t, J=7.7Hz, 1H). 7.13–7.17(m, 2H). 7.23–7.28(m, 8H), 7.34–7.37(m, 1H), 7.48–7.51(m, 1H), 7.56(d, J=7.7Hz, 1H), 7.76(dd, J=8.1, 1.1Hz, 1H). | 58 | Similar to Example 1 |
| Example 31 | 26 | 1.73–1.80(m, 2H), 2.18–2.25(m, 2H), 2.41–2.45(m, 2H), 2.64–2.71(m, 8H), 3.57(s, 2H), 3.79(s, 3H), 4.00(t, J=7.8Hz, 1H), 6.84(d, J=8.8Hz, 2H), 7.13–7.18(m, 2H), 7.21–7.28(m, 10H). | 31 | Similar to Example 1 |
| Example 32 | 26 | 1.74–1.80(m, 2H), 2.18–2.24(m, 2H), 2.40–2.45(m, 2H), 2.62–2.71(m, 8H), 3.61(s, 2H), 3.80(s, 3H), 4.01(t, J=7.8Hz, 1H), 6.77(dd, J=8.3, 2.4Hz, 1H), 6.88–6.91(m, 1H), 7.13–7.19(m, 2H), 7.20–7.29(m, 9H). | 37 | Similar to Example 1 |
| Example 33 | 28 | 1.78–1.87(m, 2H), 2.19–2.27(m, 2H), 2.39–2.48(m, 2H), 2.63–2.81(m, 8H), 3.71(s, 2H), 3.81(s, 3H), 4.01(t, J=7.8Hz, 1H), 6.85 (d, J=7.8Hz, 1H), 6.93(dd, J=7.3, 7.3Hz, 1H), 7.13–7.18(m, 2H), 7.19–7.29(m, 9H), 7.40(d, J=7.8Hz, 1H). | 43 | Similar to Example 1 |
| Example 34 | 29 | 1.87–1.94(m, 2H), 2.17–2.25(m, 2H), 2.37–2.42(m, 2H), 2.60–2.65(m, 2H), 2.70–2.75(m, 2H), 3.28–3.34(m, 2H), 3.35–3.40(m, 2H), 3.99(t, J=7.8Hz, 1H), 6.77(ddd, J=8.3, 6.8, 1.0Hz, 1H), 7.02(dd, J=8.8, 1.0Hz, 1H), 7.14–7.19(m, 2H), 7.20–7.29(m, 8H), 7.35(ddd, J=8.8, 6.8, 1.5Hz, 1H), 7.71(dd, J=8.3, 1.5Hz, 1H). | 45 | Similar to Example 1 |
| Example 35 | 30 | 1.7–1.85(m, 2H), 2.15–2.3(m, 2H), 2.4–2.5(m, 2H), 2.6–2.75(m, 8H), 3.67(s, 2H), 4.01(t, J=7.5Hz, 1H), 7.1–7.35(m, 10H), 7.44(d, J=8.3Hz, 2H), 7.59(d, J=8.3Hz, 2H). | 38 | Similar to Example 1 |
| Example 36 | 31 | 1.7–1.85(m, 2H), 2.15–2.3(m, 2H), 2.4–2.5(m, 2H), 2.6–2.75(m, 8H), 3.66(s, 2H), 4.01(t, J=7.5Hz, 1H), 7.1–7.35(m, 10H), 7.43(d, J=8.0Hz, 2H), 7.55(d, J=8.0Hz, 2H). | 30 | Similar to Example 1 |
| Example 37 | 32 | 1.75–1.88(m, 2H), 2.20–2.32(m, 2H), 2.39–2.50(m, 2H), 2.62–2.90(m, 12H), 4.00(t, J=7.6Hz, 1H), 7.11–7.25(m, 10H), 7.34(d, J=8.6Hz, 2H), 8.13(d, J=8.6Hz, 2H). | 53 | Similar to Example 1 |
| Example 38 | 33 | 1.73–1.89(m, 4H), 2.16–2.27(m, 2H), 2.39–2.47(m, 2H), 2.48(t, J=7.3Hz, 2H), 2.58–2.70(m, 8H), 2.73(t, J=7.3Hz, 2H), 4.00(t, J=7.6Hz, 1H), 7.12–7.20(m, 2H), 7.20–7.30(m, 8H), 7.33(d, J=8.6Hz, 2H), 8.13(d, J=8.6Hz, 2H), | 55 | Similar to Example 1 |
| Example 39 | 34 | 1.75–1.85(m, 2H), 2.2–2.35(m, 2H), 2.45–2.55(m, 2H), 2.6–2.8(m, 8H), 3.58(s, 2H), 3.99(t, J=7.5Hz, 1H), 7.1–7.35(m, 14H). | 26 | Similar to Example 1 |
| Example 40 | 35 | 1.7–1.85(m, 2H), 2.15–2.3(m, 2H), 2.4–2.5(m, 2H), 2.6–2.75(m, 8H), 3.66(s, 2H), 3.95(s, 3H), 4.02(t, J=7.5Hz, 1H), 6.96(d, J=6.9Hz, 1H), 7.1–7.35(m, 11H), 7.81(d, J= 8.2Hz, 1H). | 48 | Similar to Example 1 |
| Example 41 | 36 | 1.73–1.86(m, 2H), 2.15–2.29(m, 2H), 2.40–2.51(m, 2H), 2.55–2.71(m, 8H), 3.04(s, 3H), 3.71(s, 2H), 4.01(t, J=7.6Hz, 1H), 7.11–7.32(m, 10H), 7.54(d, J=8.2Hz, 2H), 7.87(d, J=8.2Hz, 2H). | 57 | Similar to Example 1 |
| Example 42 | 37 | 1.72–1.84(m, 2H), 2.16–2.28(m, 2H), 2.39–2.48(m, 2H), 2.61–2.74(m, 8H), 3.74(s, 2H), 3.90(s, 3H), 4.01(t, J=7.6Hz, 1H), 7.11–7.20(m, 2H), 7.20–7.31(m, 8H), 7.40(d, J=8.3Hz, 2H), 7.97(d, J=8.3Hz, 2H). | 37 | Similar to Example 1 |

TABLE 2-continued

| | Compound No. | ¹H NMR Data (CDCl₃) δ(ppm) | Yield (%) | Synthetic method |
|---|---|---|---|---|
| Example 43 | 38 | 1.7–1.75(m, 2H), 2.15–2.25(m, 2H), 2.29(s, 3H), 2.4–2.5(m, 2H), 2.6–2.77(m, 8H), 3.05(s, 3H), 3.70(s, 2H), 3.97(t, J=7.6Hz, 1H), 7.03–7.33(m, 9H), 7.54(d, J=8.2Hz, 2H), 7.86(d, J=8.2Hz, 2H). | 10 | Similar to Example 1 |
| Example 44 | 39 | 1.7–1.75(m, 2H), 2.15–2.25(m, 2H), 2.30(s, 3H), 2.4–2.5(m, 2H), 2.6–2.8(m, 8H), 3.04(s, 3H), 3.70(s, 2H), 3.96(t, J=7.6 Hz, 1H), 6.9–7.3(m, 9H), 7.54(d, J=8.2Hz, 2H), 7.86(d, J=8.2Hz, 2H). | 26 | Similar to Example 1 |
| Example 45 | 40 | 1.75–1.88(m, 2H), 2.12–2.22(m, 2H), 2.28(s, 3H), 2.4–2.6(m, 2H), 2.6–2.85(m, 8H), 3.05(s, 3H), 3.71(s, 2H), 4.23(t, J=7.6Hz, 1H), 7.1–7.3(m, 8H), 7.35(d, J=7.5Hz, 1H), 7.54(d, J=8.2Hz, 2H), 7.88(d, J=8.2Hz 2H). | 26 | Similar to Example 1 |
| Example 46 | 41 | 1.7–1.85(m, 2H), 2.1–2.25(m, 2H), 2.35–2.5(m, 2H), 2.55–2.75(m, 8H), 3.05(s, 3H), 3.71(s, 2H), 3.76(s, 3H), 3.95(t, J=7.7Hz, 1H), 6.81(d, J=8.6Hz, 1H), 7.1–7.3(m, 7H), 7.54(d, J=8.2Hz, 2H), 7.87(d, J=8.2Hz, 2H). | 19 | Similar to Example 1 |
| Example 47 | 43 | 1.75–1.85(m, 2H), 2.13–2.15(m, 2H), 2.41(t, J=7.3Hz, 2H), 2.58–2.74(m, 8H), 3.05(s, 3H), 3.70(s, 2H), 4.00(t, J=7.7Hz, 1H), 7.12–7.31(m, 9H), 7.54(d, J=8.2Hz, 2H), 7.87(d, J=8.2Hz, 2H). | 40 | Similar to Example 1 |
| Example 48 | 44 | 1.7–1.85(m, 2H), 2.12–2.25(m, 2H), 2.44(t, J=7Hz, 2H), 2.55–2.75(m, 8H), 3.58(s, 2H), 3.76(s, 3H), 3.95(t, J=7.7Hz, 1H), 6.81(d, J=8.8Hz, 2H), 7.15(d, J=8.7Hz, 2H), 7.15–7.31(m, 9H). | 15 | Similar to Example 1 |
| Example 49 | 45 | 1.74–1.84(m, 2H), 2.12–2.23(m, 2H), 2.37–2.45(m, 2H), 2.60–2.71(m, 8H), 3.02(s, 3H), 3.70(s, 2H), 4.03(t, J=7.6Hz, 1H), 6.85(dt, J=6.6, 1.5Hz, 1H), 6.94(td, J=10.2, 1.6Hz, 1H), 7.02(d, J=7.6Hz, 1H), 7.14–7.31(m, 6H), 7.54(d, J=8.6Hz, 2H), 7.87(d, J=8.2Hz, 2H). | 35 | Similar to Example 1 |
| Example 50 | 46 | 1.72–1.88(m, 2H), 2.15–2.30(m, 2H), 2.40–2.60(m, 2H), 2.60–2.90(m, 8H), 3.55(s, 2H), 3.78(t, 1H, J=7.6Hz), 6.53(d, 2H, J=8.5Hz), 6.98(d, 2H, J=8.5Hz), 7.1–7.3(m, 9H). | 39 | Similar to Example 16 |
| Example 51 | 47 | 1.75–1.85(m, 2H), 2.12–2.21(m, 2H), 2.39–2.45(m, 2H), 2.65–2.77(m, 8H), 3.04(s, 3H), 3.70(s, 2H), 4.01(t, J=7.6Hz, 1H), 6.90–6.98(m, 4H), 7.12–7.26(m, 4H), 7.54(d, J=8.2Hz, 2H), 7.87(d, J=8.2Hz, 2H). | 36 | Similar to Example 1 |
| Example 52 | 48 | 1.75–1.85(m, 2H), 2.18–2.26(m, 2H), 2.42–2.52(m, 2H), 2.62–2.76(m, 8H), 3.04(s, 3H), 3.75(s, 2H), 4.01(t, J=7.6Hz, 1H), 6.91–6.99(m, 2H), 7.13–7.31(m, 7H), 7.54(d, J=8.6Hz, 2H), 7.87(d, J=8.2Hz, 2H). | 19 | Similar to Example 1 |
| Example 53 | 49 | 1.74–1.85(m, 2H), 2.17–2.28(m, 2H), 2.43–2.52(m, 2H), 2.63–2.72(m, 8H), 3.05(s, 3H), 3.71(s, 2H), 4.38(t, J=7.6Hz, 1H), 6.94–7.21(m, 4H), 7.25–7.31(m, 5H), 7.54(d, J=8.6Hz, 2H), 7.87(d, J=8.2Hz, 2H). | 45 | Similar to Example 1 |
| Example 54 | 50 | 1.72–1.85(m, 2H), 2.14–2.28(m, 2H), 2.44(t, J=7.3Hz, 2H), 2.60–2.76(m, 8H), 3.55(s, 2H), 4.00(t, J=7.7Hz, 1H), 7.10–7.31(m, 13H). | 14 | Similar to Example 1 |
| Example 55 | 51 | 1.74–1.85(m, 2H), 2.15–2.25(m, 2H), 2.43–2.52(m, 2H), 2.60–2.75(m, 8H), 3.03(s, 3H), 3.71(s, 2H), 4.60(t, J=7.8Hz, 1H), 7.06–7.39(m, 9H), 7.54(d, J=8.2Hz, 2H), 7.87(d, J=8.2Hz, 2H). | 8 | Similar to Example 1 |
| Example 56 | 52 | 1.69–1.77(m, 2H), 2.15–2.30(m, 2H), 2.37–2.45(m, 2H), 2.60–2.69(m, 8H), 3.57(s, 2H), 4.00(t, J=7.7Hz, 1H), 6.97(t, $J_{N-F}$=8.9Hz, 2H), 7.11–7.18(m, 2H), 7.21–7.30(m, 10H). | 21 | Similar to Example 1 |
| Example 57 | 53 | 1.71–1.79(m, 2H), 2.10–2.20(m, 2H), 2.33–2.40(m, 2H), 2.57–2.69(m, 8H), 3.57(s, 2H), 3.99(t, J=7.8Hz, 1H), 7.10–7.15(m, 4H), 7.20–7.25(m, 8H). | 23 | Similar to Example 1 |
| Example 58 | 54 | 1.70–1.79(m, 2H), 2.11–2.17(m, 2H), 2.33–2.41(m, 2H), 2.60–2.68(m, 8H), 3.58(s, 2H), 4.00(t, J=7.7Hz, 1H), 6.90–6.99(m, 4H), 7.12–7.20(m, 4H), 7.26(s, 4H). | 15 | Similar to Example 1 |
| Example 59 | 56 | 1.86–1.93(m, 2H), 2.25–2.37(m, 2H), 2.54–2.60(m, 2H), 2.67–2.95(m, 8H), 3.05(s, 3H), 3.71(s, 2H), 4.00(t, J=7.9Hz, 1H), 7.11–7.19(m, 4H), 7.20–7.30(m, 4H), 7.53(d, J=8.2Hz, 2H), 7.87(d, J=8.2Hz, 2H). | 10 | Similar to Example 1 |
| Example 60 | 57 | 1.73–1.86(m, 2H), 2.22–2.31(m, 2H), 2.43–2.52(m, 2H), 2.65–2.80(m, 8H), 3.55(s, 2H), 3.91(t, J=7.6Hz, 1H), 6.3(broad s,1H), 6.61(d, J=8.2Hz, 2H), 7.08–7.32(m, 12H). | 29 | Similar to Example 1 |
| Example 61 | 58 | 1.70–1.85(m, 2H), 2.15–2.28(m, 2H), 2.40–2.54(m, 2H), 2.57–2.80(m, 8H), 3.05(S, 3H), 3.69(s, 2H), 3.90(t, J=7.3Hz, 1H), 6.60–6.68(m, 2H), 6.80(d, J=7.9Hz, 1H), 7.08–7.32(m, 6H), 7.52(d, J=8.2Hz, 2HJ. 7.87(d, J=8.2Hz, 2H). | 48 | Similar to Example 1 |
| Example 62 | 59 | 1.90–2.10(m, 2H), 2.40–2.97(m, 12H), 3.05(S, 3H), 3.75(s, 2H), 4.40–4.50(m, 1H), 6.65–6.77(m, 2H), 6.93(d, J=7.6Hz, 1H), 7.00–7.10(m, 1H), 7.15–7.35(m, 5H), 7.60(d, J=8.3Hz, 2H), 7.89(d, J=8.3Hz, 2H). | 44 | Similar to Example 1 |
| Example 63 | 60 | 1.73–1.79(m, 2H), 2.15–2.26(m, 2H), 2.37–2.47(m, 2H), 2.60–2.75(m, 8H), 2.98(broad s, 3H), 3.10(broad s, 3H), 3.64(s, 2H), 4.00(t, J=7.6Hz, 1H), 7.15–7.33(m, 10H), 7.35(s, 4H). | 29 | Similar to Example 1 |
| Example 64 | 61 | 1.70–1.76(m, 2H), 2.10–2.24(m, 2H), 2.35–2.45(m, 2H), 2.58–2.70(m, 8H), 3.64(s, 2H), 3.97(t, J=7.6Hz, 1H), 4.90(broad s, 2H), 7.10–7.30(m, 10H), 7.42(d, J=8.1Hz, 2H), 7.82(d, J=8.1Hz, 2H). | 10 | Similar to Example 1 |
| Example 65 | 62 | 7.54(d, J=8.1Hz, 4H), 7.34(d, J=8.1Hz, 4H), 7.26(s, 4H), 4.20(t, J=7.6Hz, 1H), 3.58(s, 2H), 2.69–2.61(m, 8H), 2.42–2.37(m, 2H), 2.25–2.17(m, 2H), 1.81–1.72(m, 2H). | 72 | Similar to Example 1 |
| Example 66 | 63 | 1.65–1.80(m, 2H), 2.10–2.25(m, 2H), 2.40–2.51(m, 2H), 2.51–2.74(m, 8H), 3.53(s, 2H), 3.84(t, J=7.6Hz, 1H), 6.53(s, 1H), 6.60(dd, J=1.6, 7.9Hz, 1H), 6.76(d, J=7.6Hz, 1H), 7.06–7.33(m, 10H). | 19 | Similar to Example 1 |
| Example 67 | 64 | 1.85–2.10(m, 2H), 2.30–2.90(m, 12H), 3.61(s, 2H), 4.40–4.50(m, 1H), 6.64–6.75(m, 2H), 6.93(d, J=7.9Hz, 1H), 7.00–7.10(m, 1H), 7.15–7.40(m, 9H). | 39 | Similar to Example 1 |

TABLE 2-continued

| | Compound No. | ¹H NMR Data (CDCl₃) δ(ppm) | Yield (%) | Synthetic method |
|---|---|---|---|---|
| Example 68 | 65 | 1.72–1.81(m, 2H), 2.10–2.19(m, 2H), 2.42–2.45(m 2H), 2.64–2.72(m, 8H), 3.58(s, 2H), 3.76(s, 6H), 6.80(d, 4H. J=8.91Hz), 7.13(d, 4H, J=8.91Hz), 7.26(s, 4H). | 49 | Similar to Example 1 |
| Example 69 | 66 | 1.83–1.85(m, 2H), 2.16–2.24(m, 2H), 2.59–2.72(m, 6H), 2.84–2.94(m, 4H), 3.62(s, 2H), 3.76(m, 1H), 6.69(d, 4H, J=8.58Hz), 7.05(d, 4H, J=8.58Hz), 7.30(s, 4H). | 19 | Similar to Example 1 |
| Example 70 | 67 | 1.81–1.85(m, 2H), 2.15–2.24(m, 2H), 2.56–2.62(m, 2H), 2.68–2.72(m, 4H), 2.81–2.91(m, 4H), 3.10(s, 3H), 3.73–3.78(m, 3H), 6.68(d, 4H, J=8.58Hz), 7.05(d, 4H, J=8.58Hz), 7.59(d, 2H, J=8.58Hz), 7.89(d, 2H, J=8.58Hz). | 3 | Similar to Example 1 |
| Example 71 | 68 | 1.74–1.80(m, 2H), 1.90(broad s, 2H), 2.12–2.28(m, 2H), 2.40–2.76(m, 10H), 2.91(s, 3H), 3.49(s 2H), 6.84–6.88(m, 1H), 7.00–7.20(m, 6H), 7.30–7.35(m, 2H), 7.43(d, J=8.4Hz, 2H), 7.74(d, J=8.4Hz, 2H). | 1 | Similar to Example 1 |
| Example 72 | 102 | 1.38–1.52(m, 2H), 1.72–1.86(m, 2H), 1.98–2.12(m, 2H), 2.52(t, J=7.6Hz, 2H), 2.58–2.75(m, 8H), 3.05(S, 3H), 3.69(s, 2H), 3.89(t, J=7.9Hz, 1H), 7.11–7.31(m, 10H), 7.53(d, J=8.2Hz, 2H), 7.87(d, J=8.2Hz, 2H). | 59 | Similar to Example 1 |
| Example 73 | 103 | 1.71–1.77(m, 2H), 2.33–2.39(m, 2H), 2.49–2.55(m, 2H), 2.57–2.71(m, 8H), 3.05(s, 3H), 3.07(s, 3H), 3.67(s, 2H), 7.15–7.36(m, 10H), 7.52(d, J=8.3Hz, 4H), 7.86(d, J=8.3Hz, 2H). | 4 | Similar to Example 1 |
| Example 74 | 104 | 1.63–1.80(m, 2H), 2.10–2.20(m, 2H), 2.35–2.75(m, 13H), 3.01(s, 3H), 3.05(s, 3H), 3.61(s, 2H), 6.55–6.67(m, 4H), 6.80–6.90(m, 2H), 7.03–7.13(m, 2H), 7.46(d, J=8.1Hz, 2H), 7.84(d, J=8.1Hz, 2H). | 20 | Similar to Example 1 |
| Example 75 | 106 | 1.79–1.88(m, 2H), 2.37–2.41(m, 2H), 2.56–2.71(m, 10H), 3.05(s, 3H), 3.71(s, 2H), 7.15–7.20(m, 2H), 7.26–7.32(m, 4H), 7.45–7.48(m, 4H), 7.56(d, 2H, J=8.25Hz), 7.88(d, 2H, J=8.58Hz). | 69 | Similar to Example 9 |
| Example 76 | 108 | 1.75–1.86(m, 2H), 2.29(s, 6H), 2.32–2.36(m, 2H), 2.53–2.71(m, 10H), 3.57(s, 2H), 7.09(d, 2H, J=8.24Hz), 7.26(s, 4H), 7.33(d, 2H, J=8.25Hz). | 26 | Similar to Example 9 |
| Example 77 | 109 | 1.57–1.61(m, 2H), 2.12–2.24(m, 2H), 2.32–2.57(m, 10H), 3.45(s, 2H), 4.75(broad s, 3H), 6.40–6.51(m, 2H), 6.67–6.77(m, 4H), 6.88–7.00(m, 2H), 7.09–7.20(m, 4H), (solvent: CD₃OD) | 75 | Similar to Example 12 |
| Example 78 | 110 | 1.80–1.84(m, 2H), 2.38–2.42(m, 2H), 2.58–2.72(m, 10H), 3.58(s, 2H), 7.27(s, 4H), 7.54–7.62(m, 8H). | 84 | Similar to Example 9 |
| Example 79 | 111 | 7.35(d, J=8.9Hz, 4H), 7.26(s, 4H), 6.82(d, J=8.9Hz, 4H), 3.76(s, 6H), 3.56(s, 2H), 2.70–2.53(m, 10H), 2.33–2.29(m, 2H), 1.83–1.78(m, 2H). | 38 | Similar to Example 9 |
| Example 80 | 112 | 7.26(s, 4H), 7.26–7.70(m, 6H), 6.36(dd, J=7.9, 2.0Hz, 2H), 3.77(s, 6H), 3.57(s, 2H), 2.71–2.55(m, 10H), 2.36–2.32(m, 2H), 1.83–1.79(m, 2H). | 22 | Similar to Example 9 |
| Example 81 | 113 | 1.84–1.88(m, 2H), 2.46–2.48(m, 2H), 2.66–2.76(m, 10H), 3.04(s,. 3H), 3.72(s, 2H), 7.25–7.43(m, 6H), 7.56–7.60(m, 10H), 7.88(d, 2H, J=8.58Hz). | 89 | Similar to Example 9 |
| Example 82 | 114 | 1.65–1.78(m, 2H), 2.27–2.38(m, 2H), 2.45–2.68(m, 11H), 3.04(s, 3H), 3.59(s, 2H), 6.62(d, J=7.9Hz, 2H), 6.90–7.13(m, 6H), 7.45(d, J=8.3Hz, 2H), 7.81(d, J=8.3Hz, 2H). | 52 | Similar to Example 12 |
| Example 83 | 115 | 7.87(d, J=8.2Hz, 2H), 7.66(d, J=8.2Hz, 2H), 7.54(d, J=8.2Hz, 2H), 7.18(t, J=7.6Hz, 2H), 6.97(t, J=7.6Hz, 2H), 6.78(d, J=7.7Hz, 2H), 3.69(s, 2H), 3.42(s, 6H), 3.05(s, 3H), 2.78–2.50(m, 12H), 1.86–1.81(m, 2H). | 83 | Similar to Example 9 |
| Example 84 | 116 | 1.28(s, 18H), 1.84–1.86(m, 2H), 2.34–2.38(m, 2H), 2.54–2.72(m, 10H), 3.05(s, 3H), 3.71(s, 2H), 7.27–7.31(m, 4H), 7.36–7.39(m, 4H), 7.56(d, 2H, J=8.58Hz), 7.88(d, 2H, J=8.25Hz). | 83 | Similar to Example 9 |
| Example 85 | 117 | 7.89(d, J=8.3Hz, 2H), 7.58–7.54(m, 10H), 3.72(s, 2H), 3.05(s, 3H), 2.72–2.59(m, 10H), 2.43–2.39(m, 2H), 1.84–1.80(m, 2H), 1.59(br s, 1H). | 61 | Similar to Example 9 |
| Example 86 | 118 | 1.80–1.90(m, 2H), 1.85(s, 6H), 2.45–2.52(m, 4H), 2.65–2.80(m, 8H), 3.05(s, 3H), 3.10(broad s, 1H), 3.72(s, 2H), 7.01(d, J=7.4Hz, 2H), 7.13(t, J=7.4Hz, 2H), 7.20(t, J=7.4Hz, 2H), 7.56(d, J=8.1Hz, 2H), 7.77(d, J=7.8Hz, 2H), 7.88(d, J=8.1Hz, 2H), (solvent: CDCl₃—CD₃OD). | 13 | Similar to Example 9 |
| Example 87 | 120 | 1.85–1.97(m, 2H), 2.39–2.49(m, 4H), 2.67–2.85(m, 9H), 2.85–2.95(m, 2H), 3.04(s, 3H), 3.71(s, 2H), 7.05–7.15(m, 2H), 7.18–7.27(m, 2H), 7.53–7.62(m, 4H), 7.67–7.80(m, 4H), 7.88(d, J=8.3Hz, 2H), 8.17–8.31(m, 4H). | 10 | Similar to Example 9 |
| Example 88 | 121 | 1.75–1.89(m, 2H), 2.28–2.33(m, 2H), 2.51–2.57(m, 2H), 2.58–2.75(m, 9H), 2.89(s, 12H), 3.04(s, 3H), 3.70(s, 2H), 6.67(d, J=8.6Hz, 4H), 7.29(d, J=8.6Hz, 4H), 7.55(d, J=8.3Hz, 2H), 7.87(d, J=8.3Hz, 2H). | 33 | Similar to Example 9 |
| Example 89 | 122 | 1.81–1.86(m, 2H), 2.26–2.30(m, 2H), 2.58–2.73(m, 10H), 3.06(s, 3H), 3.71(s, 2H), 5.91(s, 4H), 6.72–6.75(m, 2H), 6.91–6.94(m, 4H), 7.56(d, 2H, J=8.25Hz), 7.88(d, 2H, J=8.25Hz). | 84 | Similar to Example 9 |
| Example 90 | 123 | 1.73–1.81(m, 2H), 2.26–2.31(m, 2H), 2.48–2.46(m, 2H), 2.56–2.78(m, 8H), 3.54(s, 2H), 4.40(broad s, 3H), 6.72(d, J=8.6Hz, 4H), 7.20(d, J=8.6Hz, 2H), 7.23–7.25(m, 4H), (solvent: CDCl₃—CD₃OD) | 36 | Similar to Example 12 |
| Example 91 | 125 | 7.88(d, J=8.3Hz, 2H), 7.63–7.55(m, 3H), 7.40–7.04(m, 8H), 6.60(s, 1H), 3.73(s, 3H), 3.44(s, 3H), 3.05(s, 3H), 2.88–2.55(m, 11H), 2.80–2.11(m, 1H), 1.92–1.85(m, 2H). | 24 | Similar to Example 14 |
| Example 92 | 126 | 1.78–1.91(m, 2H), 2.33–2.41(m, 2H), 2.62–2.80(m, 10H), 3.05(s, 3H), 3.71(s, 2H), 6.91–6.98(m, 4H), 7.19(dd, J=3.3, 3.3Hz, 2H), 7.57(d, J=8.6Hz, 2H), 7.88(d, J=8.6Hz, 2H). | 74 | Similar to Example 9 |
| Example 93 | 128 | 1.78–1.91(m, 2H), 2.25–2.35(m, 2H), 2.55–2.78(m, 10H), 3.05(s, 3H), 3.71(s, 2H), 7.00(dd, J=3.3, 3.3Hz, 2H), 7.20–7.30(m, 4H), 7.56(d, J=8.6Hz, 2H), 7.88(d, J=8.6Hz, 2H). | 19 | Similar to Example 11 |
| Example 94 | 130 | 1.80–1.96(m, 2H), 1.91(s, 6H), 2.45–2.53(m, 2H), 2.63–2.77(m, 8H), 2.81(t, J=5.6Hz, 2H), 3.06(s, 3H), 3.71(s, 2H), 6.77(d, J=5.3Hz, 2H), 7.06(d, J=5.3Hz, 2H), 7.56(d, J=8.3Hz, 2H), 7.88(d, J=8.3Hz, 2H). | 23 | Similar to Example 9 |

TABLE 2-continued

| | Compound No. | $^1$H NMR Data (CDCl$_3$) δ(ppm) | Yield (%) | Synthetic method |
|---|---|---|---|---|
| Example 95 | 131 | 7.88(d, J=8.3Hz, 2H), 7.54(d, J=8.3Hz, 2H), 7.45(d, J=6.9Hz, 2H), 7.31–7.13(m, 4H), 7.03–6.96(m, 2H), 6.68–6.65(m, 1H), 3.69(s, 2H), 3.05(s, 3H), 2.74–2.58(m, 10H), 1.8(br s, 1H), 2.39–2.35(m, 2H), 1.85–1.81(m, 2H). | 8 | Similar to Example 15 |
| Example 96 | 132 | 1.77–1.88(m, 2H), 2.35–2.38(m, 2H), 2.49–2.58(m, 2H), 2.58–2.87(m, 10H), 3.05(s, 3H), 3.68(s, 2H), 3.77(t, J=7.6Hz, 1H), 6.58–6.72(m, 6H), 7.03–7.12(m, 6H), 7.50(d, J=8.3Hz, 2H), 7.86(d, J=8.3Hz, 2H). | 30 | Similar to Example 15 |
| Example 97 | 133 | 1.79–1.89(m, 2H), 2.35–2.40(m, 2H), 2.55–2.76(m, 11H), 3.05(s, 3H), 3.70(s, 2H), 3.77(s, 3H), 6.70–6.75(m, 1H), 6.99–7.03(m, 1H), 7.13–7.31(m, 4H), 7.45–7.49(m, 2H), 7.56(d, J=8.4Hz, 2H), 7.88(d, J=8.4Hz, 2H). | 30 | Similar to Example 15 |
| Example 98 | 134 | 1.66–1.75(m, 2H), 2.17(s, 3H), 2.19–2.26(m, 2H), 2.40–2.76(m, 11H), 2.91(s, 3H), 3.49(s, 2H), 6.84–6.88(m, 1H), 7.00–7.20(m, 6H), 7.30–7.35(m, 2H), 7.43(d, J=8.4Hz, 2H), 7.74(d, J=8.4Hz, 2H). | 21 | Similar to Example 15 |
| Example 99 | 135 | 1.79–1.88(m, 2H), 2.35–2.41(m, 2H), 2.54–2.78(m, 11H), 3.03(s, 3H), 3.70(s, 2H), 7.10–7.48(m, 8H), 7.55(d, J=8.3Hz, 2H), 7.87(d, J=8.3Hz, 2H), | 11 | Similar to Example 15 |
| Example 100 | 136 | 1.77–1.88(m, 2H), 2.35–2.40(m, 2H), 2.55–2.76(m, 11H), 3.05(s, 3H), 3.70(s, 2H), 3.77(s, 3H), 6.70–6.75(m, 1H), 6.99–7.03(m, 1H), 7.13–7.31(m, 4H), 7.45–7.49(m, 2H), 7.56(d, J=8.4Hz, 2H), 7.88(d, J=8.4Kz, 2H). | 7 | Similar to Example 15 |
| Example 101 | 137 | 7.86(d, J= 8.3Hz, 2H), 7.52(d, J=8.3Hz, 2H), 7.42–7.37(m, 2H), 7.15(t, J=7.9Hz, 1H), 7.07–6.89(m, 7H), 6.69–6.65–6.47(m, 1H), 3.65(s, 2H), 3.05(s, 3H), 2.75–2.59(m, 10H), 2.39–2.32(m, 2H), 1.85–1.74(m, 2H). | 12 | Similar to Example 15 |
| Example 102 | 139 | 7.87(d, J=8.3Hz, 2H), 7.60–6.94(m, 9H), 6.67–6.63(m, 1H), 5.75(s, 1H), 4.11–3.97(m, 4H), 3.68(s, 2H), 3.05(s, 3H), 2.85–2.58(m, 10H), 2.42–2.33(m, 2H), 1.88–1.72(m, 2H). | 6 | Similar to Example 15 |
| Example 103 | 140 | 1.65–1.78(m, 2H), 2.20–2.29(m, 2H), 2.41–2.61(m, 10H), 2.77(s, 3H), 2.90(s, 3H), 3.57(s, 2H), 3.72–3.79(m, 2H), 4.91–5.04(m, 2H), 5.59–5.75(m, 1H), 6.39–6.44(m, 1H), 6.55–6.62(m, 1H), 6.80–6.83(m, 1H), 6.96–7.08(m, 3H), 7.10–7.18(m, 2H), 7.30–7.39(m, 2H), 7.43(d, J=8.2Hz, 2H), 7.76(d, J=8.2Hz, 2H). | 17 | Similar to Example 15 |
| Example 104 | 141 | 1.75–1.89(m, 2H), 2.35–2.48(m, 2H), 2.48–2.85(m, 11H), 3.03(s, 3H), 3.46(s, 3H), 3.68(s, 2H), 3.78(s, 3H), 6.36(d, J=2.3Hz, 1H), 6.53(dd, J=8.6, 2.3Hz, 1H), 7.09–7.17(m, 1H), 7.18–7.31(m, 2H), 7.35–7.45(m, 2H), 7.55(d, J=8.1Hz, 2H), 7.80(d, J=8.6Hz, 1H), 7.87(d, J=8.1Hz, 2H). | 28 | Similar to Example 15 |
| Example 105 | 142 | 1.75–1.89(m, 2H), 2.31–2.38(m, 2H), 2.54–2.74(m, 11H), 3.04(s, 3H), 3.70(s, 2H), 3.75(s, 6H), 6.30(t, J=2.2Hz, 1H), 6.66(d, J=2.2Hz, 2H), 7.13–7.20(m, 1H), 7.22–7.32(m, 2H), 7.46(d, J=8.4Hz, 2H), 7.55(d, J=8.4Hz, 2H). | 25 | Similar to Example 15 |
| Example 106 | 143 | 1.65–1.78(m, 2H), 2.20–2.29(m, 2H), 2.41–2.61(m, 10H), 2.77(s, 3H), 2.90(s, 3H), 3.57(s, 2H), 3.72–3.79(m, 2H), 4.91–5.04(m, 2H), 5.59–5.75(m, 1H), 6.39–6.44(m, 1H), 6.55–6.62(m, 1H), 6.80–6.83(m, 1H), 6.96–7.08(m, 3H), 7.10–7.18(m, 2H), 7.30"7.39(m, 2H), 7.43(d, J=8.2Hz, 2H), 7.76(d, J=8.2Hz, 2H). | 17 | Similar to Example 15 |
| Example 107 | 144 | 1.78–1.82(m, 2H), 2.19–2.27(m, 2H), 2.43–2.48(m, 2H), 2.67–2.82(m, 6H), 3.40–3.45(m, 1H), 3.76(s, 2H), 3.99–4.05(m, 2H), 7.14–7.30(m, 10H), 7.65(d, 2H, J=8.25Hz), 7.96(d, 2H, J=8.25Hz). | 21 | Similar to Example 1 |
| Example 108 | 145 | 7.87(d, J=8.2Hz, 2H), 7.54(d, J=8.2Hz, 2H), 7.36–6.94(m, 7H), 6.68–6.64(m, 1H), 3.79(t, J=6.4Hz, 2H), 3.67(s, 2H), 3.05(s, 3H), 2.81(t, J=6.4Hz, 2H), 2.71–2.58(m, 10H), 2.44–2.33(m, 2H), 1.87–1.82(m, 2H). | 10 | Similar to Example 15 |
| Example 109 | 147 | 1.79–1.90(m, 2H), 2.30–2.41(m, 2H), 2.58–2.79(m, 11H), 3.04(s, 3H), 3.66(s, 2H), 6.65–6.71(m, 1H), 6.85–7.00(m, 5H), 7.02–7.20(m, 3H), 7.25–7.35(m, 2H), 7.35–7.45(m, 2H), 7.52(d, J=8.3Hz, 2H), 7.86(d, J=8.3Hz, 2H). | 26 | Similar to Example 15 |
| Example 110 | 148 | 1.78–1.90(m, 2H), 2.30–2.40(m, 2H), 2.53–2.79(m, 11H), 3.05(s, 3H), 3.71(s, 2H), 3.83(s, 3H), 5.50(broad s, 1H), 6.84(d, J=8.3Hz, 1H), 6.90(dd, J=8.3Hz, 2.0Hz, 1H), 7.04(d, J=2.0Hz, 1H), 7.14–7.22(m, 1H), 7.24–7.37(m, 2H), 7.40–7.50(m, 2H), 7.56(d, J=8.2Hz, 2H), 7.88(d, J=8.2Hz, 2H), | 24 | Similar to Example 15 |
| Example 111 | 149 | 1.77–1.90(m, 2H), 2.28–2.38(m, 2H), 2.50–2.73(m, 12H), 3.05(s, 3H), 3.69(s, 2H), 3.74(s, 3H), 6.23–6.26(m, 1H), 6.55–6.58(m, 1H), 6.61–6.64(m, 1H), 7.14–7.20(m, 1H), 7.22–7.33(m, 2H), 7.42–7.49(m, 2H), 7.55(d, J=8.3Hz, 2H), 7.88(d, J=8.3Hz, 2H). | 12 | Similar to Example 15 |
| Example 112 | 150 | 7.88(d, J=8.3Hz, 2H), 7.55(d, J=8.3Hz, 2H), 7.47(d, J=7.9Hz, 2H), 7.30–7.09(m, 7H), 7.07(s, 1H), 6.90–6.71(m, 1H), 5.88–5.75(m, 2H), 5.16–5.08(m, 4H), 3.95–3.80(m, 4H), 3.70(s, 2H), 3.05(s, 3H), 2.71–2.56(m, 10H), 2.37–2.33(m, 2H), 1.88–1.77(m, 2H). | 67 | Similar to Example 15 |
| Example 113 | 151 | 1.82–1.86(m, 2H), 2.37–2.41(m, 2H), 2.57–2.73(m, 10H), 3.05(s, 3H), 3.71(s, 2H), 4.64(s, 2H), 7.15–7.21(m, 4H), 7.26–7.32(m, 4H), 7.56(d, 2H, J=8.25Hz), 7.88(d, 2H, J=8.25Hz). | 33 | Simnilar to Example 15 |
| Example 114 | 152 | 7.89(d, J=8.6Hz, 2H), 7.56(d, J=8.6Hz, 2H), 7.38–7.16(m, 8H), 7.07(s, 1H), 4.39(d, J=11.8Hz, 1H), 4.01(d, J=11.8Hz, 1H), 3.72(s, 2H), 3.06(d, J=13.3Hz, 1H) 2.90–2.45(m, 11H), 2.33–2.14(m, 1H), 1.90–1.77(m, 2H). | 2 | Similar to Example 15 (a) |
| Example 115 | 153 | 7.89(d, J=8.3Hz, 4H), 7.76–7.72(m, 2H), 7.57(d, J=8.3Hz, 2H), 7.36–7.19(m, 3H), 3.72(s, 2H), 3.04(s, 3H), 2.82–2.56(m, 11H), 2.39–2.30(m, 1H), 1.89–1,81(m, 2H). | 24 | Similar to Example 14 |

TABLE 2-continued

| | Compound No. | $^1$H NMR Data (CDCl$_3$) δ(ppm) | Yield (%) | Synthetic method |
|---|---|---|---|---|
| Example 116 | 154 | 1.80–1.84(m, 2H), 2.04(m, 2H), 2.59–2.69(m, 10H), 3.04(s, 3H), 3.67(s, 2H), 3.89(s, 3H), 6.64–6.67(m, 1H), 7.00–7.19(m, 5H), 7.41–7.44(m, 1H), 7.53(d, 2H. J=7.25Hz), 7.61–7.72(m. 2H), 7.85–7.91(m, 3H). | 58 | Similar to Example 15 |
| Example 117 | 155 | 0.84–0.89(m, 3H), 1.23–1.37(m, 12H), 1.55–1.58(m, 2H), 1.78–1.79(m, 2H), 2.33(m, 1H), 2.50–2.76(m, 12H), 3.04(s, 3H), 3.65(s, 2H), 6.63–6.67(m, 1H), 6.95(d, 1H, J=7.59Hz), 7.06–7.17(m, 4H), 7.33(d, 2H, J=8.25Hz), 7.52(d, 2H. J=8.25Hz), 7.86(d, 2H, J=8.58Hz). | 51 | Similar to Example 15 |
| Example 118 | 156 | 8.48(br s, 1H), 7.72(d, J=8.3Hz, 2H), 7.56(d, J=8.3Hz, 2H), 7.50–7.47(m, 2H), 7.33–7.17(m, 3H), 6.68–6.66(m, 1H), 6.17–6.06(m, 2H), 3.71(s, 2H), 3.05(s, 3H), 3.03(d, J=13.3Hz, 1H), 2.80–2.50(m, 10H), 2.39–2.28(m, 1H), 2.13–2.13 9m, 1H), 1.88–1.79(m, 2H). | 16 | Similar to Example 14 . . . (a) |
| Example 119 | 157 | 7.89(d, J=8.3Hz, 2H), 7.66–7.62(m, 2H), 7.56(d, J=8.3Hz, 2H), 7.34–7.18(m, 3H), 7.00(s, 2H), 3.71(s, 2H), 3.04(s, 3H), 3.06(d, J=13.3Hz, 1H), 2.79–2.51(m, 11H), 2.30–2.17(m, 1H), 1.87–1.78(m, 2H). | 21 | Similar to Example 14 . . . (a) |
| Example 120 | 158 | 1.73–1.83(m, 2H), 2.26–2.44(m, 2H), 2.45–2.75(m, 11H), 3.05(s, 3H), 3.62(s, 2H), 6.60–6.68(m, 1H), 6.88–6.95(m, 1H), 7.00–7.02(m, 1H), 7.07–7.15(m, 1H), 7.31–7.58(m, 5H), 7.78–7.88(m, 3H). | 31 | Similar to Example 15 |
| Example 121 | 159 | 7.88(d, J=8.3Hz, 2H), 7.55(d, J=8.3Hz, 2H), 7.46(d, J=8.6Hz, 2H), 7.32–7.05(m, 4H), 6.84–6.82(m, 2H), 6.54–6.50(m, 1H), 3.71(s, 2H), 3.05(s, 3H), 3.03(d, L=13.3Hz, 1H) 2.86–2.53(m, 10H), 2.46–2.33(m, 2H), 1.90–1.77(m, 2H). | 39 | Similar to Example 17 |
| Example 122 | 160 | 7.88(d, J=8.3Hz, 2H), 7.58(d, J=8.3Hz, 2H), 7.46(d, J=7.3 Hz, 2H), 7.33–7.17(m, 3H), 6.69–6.66(m, 1H), 6.17–6.07(m, 2H), 3.97(d, J=5.3Hz, 2H), 3.74(s, 2H), 3.33(d, J=5.3Hz, 2H), 2.79–2.50(m, 10H), 2.38–2.14(m, 2H), 1.89–1.80(m, 2H). | 12 | Similar to Example 14 (a), (b) |
| Example 123 | 161 | 1.76–1.78(m, 2H), 2.31(m, 2H), 2.60–2.67(m, 10H), 3.02(s, 3H), 3.61(s, 2H), 5.75(s, 1H), 6.62–6.65(m, 1H), 6.90–6.93(m, 1H), 7.03(s, 1H), 7.09–7.15(m, 1H), 7.23–7.39(m, 9H), 7.49(d, 2H. J=8.25Hz), 7.83(d, 2H, J=8.25Hz). | 50 | Similar to Example 15 |
| Example 124 | 163 | The structure was confirmed by ESI/MS m/e 515.5 (M$^+$ + H, C$_{28}$H$_{32}$F$_2$N$_2$O$_3$S). | 12 | Similar to Example 9 |
| Example 125 | 164 | 1.77–1.90(m, 2H), 2.29–2.38(m, 2H), 2.53–2.80(m, 10H), 3.05(s, 3H), 3.71(s, 2H), 6.35(broad s, 1H), 6.90–7.05(m, 4H), 7.35–7.45(m, 4H), 7.55(d, J=8.3 Hz, 2H), 7.88(d, J=8.3Hz, 2H). | 9 | Similar to Example 9 |
| Example 126 | 165 | The structure was confirmed by ESI/MS m/e 547.5 (M$^+$ + H, C$_{28}$H$_{32}$Cl$_2$N$_2$O$_3$S). | 10 | Similar to Example 9 |
| Example 127 | 166 | The structure was confirmed by ESI/MS m/e 547.5 (M$^+$ + H, C$_{28}$H$_{32}$Cl$_2$N$_2$O$_3$S). | 6 | Similar to Example 9 |
| Example 128 | 167 | 1.78–1.89(m, 2H), 2.30–2.38(m, 2H), 2.54–2.76(m, 11H), 3.05(s, 3H), 3.70(s, 2H), 3.77(s, 6H), 6.69–6.75(m, 2H), 6.97–7.03(m, 2H), 7.16–7.24(m, 2H), 7.55(d, J=8.3Hz, 2H), 7.88(d, J=8.3Hz, 2H). | 12 | Similar to Example 9 |
| Example 129 | 168 | Tbe structure wes confirmed by ESI/MS m/e 539.5 (M$^+$ + H, C$_{30}$H$_{30}$N$_2$O$_5$S). | 67 | Similar to Example 12 |
| Example 130 | 169 | 1.76–1.92(m, 2H), 2.28–2.40(m, 2H), 2.52–2.77(m, 10H), 3.06(s, 3H), 3.70(s, 2H), 6.68(dd, J=7.9 and 1.7Hz, 1H), 6.82–6.93(m, 2H), 6.95–7.03(m, 2H), 7.13–7.31(m, 4H), 7.55(d, J=8.6Hz, 2H), 7.88(d, J=8.6Hz, 2H). | 52 | Similar to Example 15 |
| Example 131 | 170 | 1.77–1.90(m, 2H), 2.25–2.39(m, 2H), 2.52–2.78(m, 10H), 3.06(s, 3H), 3.70(s, 2H), 6.68(dd, J=7.9 and 2.3Hz. 1H), 6.92–7.02(m, 2H), 7.12–7.35(m, 4H), 7.49(s, 1H), 7.55(d, J=8.3Hz, 2H), 7.88(d, J=8.3Hz, 2H). | 62 | Similar to Example 15 |
| Example 132 | 171 | 1.75–1.89(m, 2H), 2.28–2.40(m, 2H), 2.51–2.75(m, 10H), 3.05(s, 3H), 3.69(s, 2H), 6.67(dd, J=7.9 and 2.3Hz, 1H), 6.94(d, J=8.25Hz, 1H), 6.99(d, J=2.3Hz, 1H), 7.16(dd, J=7.9 and 7.9Hz, 1H), 7.25(d, J=8.3Hz, 2H), 7.39(d, J=8.3Hz, 2H), 7.54(d, J=8.3Hz, 2H), 7.88(d, J=8.3Hz, 2H). | 60 | Similar to Example 15 |
| Example 133 | 172 | 1.70–1.81(m, 2H), 2.25–2.34(m, 2H), 2.50–2.72(m, 12H), 3.03(s, 3H), 3.60(s, 2H), 3.69(s, 6H) 6.23–6.27(m, 1H), 6.59–6.68(m, 3H), 6.88–6.95(m, 1H), 7.07–7.17(m, 2H), 7.48(d, J=8.3Hz, 2H), 7.83(d, J=8.3Hz, 2H). | 22 | Similar to Example 15 |
| Example 134 | 173 | 1.70–1.81(m, 2H), 2.26–2.37(m, 2H) 2.50–2.70(m, 12H), 3.03(s, 3H), 3.60(s, 2H), 3.72(s, 3H), 6.60–6.72(m, 2H), 6.90–6.95(m, 1H), 6.95–7.00(m, 1H), 7.01–7.19(m, 4H), 7.48(d, J=8.3Hz, 2H), 7.83(d, J=8.3Hz, 2H). | 33 | Similar to Example 15 |
| Example 135 | 197 | 7.88(d, J=8.3Hz, 2H), 7.56(d, J=8.3Hz, 2H), 7.51–7.47(m, 4H), 7.30–7.13(m, 6H), 3.71(s, 2H), 3.05(s, 3H), 2.73–2.46(m, 8H), 1.85–1.76(m, 4H), 1.62–1.59(m, 2H). | 41 | Similar to Example 9 |
| Example 136 | 198 | 7.83(d, J=8.3Hz, 2H), 7.43(d, J=8.4Hz, 2H), 7.17–7.07(m, 4H), 6.91(d, J=7.6Hz, 2H), 3.56(s, 2H), 3.04(s, 3H), 2.62–2.42(m, 12H), 1.8(br s), 1.75–1.50(m, 4H). | 11 | Similar to Example 12 |
| Example 137 | 200 | 1.74–1.84(m, 2H), 2.11–2.21(m, 2H), 2.36–2.43(m, 2H), 2.59–2.67(m, 4H), 3.31–3.37(m, 4H), 3.97(t, J=7.6Hz, 1H), 7.12–7.30(m, 10H), 7.48(d, J=8.6Hz, 2H), 7.72(d, J=8.6Hz, 2H). | 70 | Similar to Example 3 |

TABLE 2-continued

| | Compound No. | $^1$H NMR Data (CDCl$_3$) δ(ppm) | Yield (%) | Synthetic method |
|---|---|---|---|---|
| Example 138 | 201 | 1.69–1.79(m, 1H), 1.89–1.99(m, 1H), 2.13–2.28(m, 2H), 2.37–2.49(m, 2H), 2.54–2.62(m, 2H), 2.64–2.69(m, 1H), 2.75–2.80(m, 1H), 3.33–3.39(m, 2H), 3.73–3.78(m, 2H), 4.01(dd, J=17.5, 7.6Hz, 1H), 7.13–7.32(m, 12H), 8.63–8.69(m, 2H). | 57 | Similar to Example 3 |
| Example 139 | 203 | 1.70–1.85(m, 2H), 2.14–2.25(m, 2H), 2.30(d, J=2.0Hz, 3H), 2.34–2.45(m, 2H), 2.49–2.57(m, 2H), 2.60–2.68(m, 2H), 3.15(d, J=7.9Hz, 2H), 3.48–3.60(m, 6H), 3.99(dt, J=2.0, 7.6Hz, 1H), 7.12–7.32(m, 15H). | 38 | Similar to Example 4 |
| Example 140 | 205 | 0.87(t, J=7.3Hz; 3H), 1.40–1.55(m, 2H), 1.71–1.81(m, 2H), 2.16–2.25(m, 2H), 2.37–2.45(m, 4H), 2.52–2.71(m, 8H), 4.00(t, J=7.9Hz, 1H), 7.12–7.20(m, 2H), 7.20–7.31(m, 8H). | 25 | Similar to Example 5 |
| Example 141 | 208 | 1.74–1.83(m, 2H), 2.17–2.26(m, 2H), 2.40–2.47(m, 2H), 2.63–2.75(m, 8H), 3.44(s, 2H), 4.00(t, J=7.6Hz, 1H), 5.51(s, 1H), 7.13–7.32(m, 10H). | 30 | Similar to Example 6 |
| Example 142 | 209 | 1.72–1.81(m, 2H), 2.17–2.27(m, 2H), 2.39–2.49(m, 2H), 2.47(t, J=7.6Hz, 2H), 2.63–2.73(m, 8H), 2.84(t, J=7.6Hz, 2H), 3.67(s, 3H), 3.99(t, J=7.6Hz, 1H), 7.12–7.20(m, 2H), 7.22–7.31(m, 8H). | 64 | Similar to Example 1 |
| Example 143 | 235 | 2.17–2.35(m, 4H), 2.35–2.60(m, 8H), 3.50(s, 2H), 3.97(t, J=7.3Hz, 1H), 7.11–7.35(m, 12H), 8.53(d, J=5.9Hz, 2H). | 17 | Similar to Example 8 |
| Example 144 | 238 | 1.77–1.86(m, 2H), 2.18–2.27(m, 2H), 2.40–2.46(m, 2H), 2.66–2.72(m, 4H), 2.78–2.88(m, 6H), 2.91–2.98(m, 2H), 4.01(t, J=7.6Hz, 1H), 6.97(s, 1H), 7.01–7.31(m, 12H), 7.35(d, J=7.9Hz, 1H), 7.61(d, J=7.9Hz, 1H), 7.94(br, 1H). | 11 | Similar to Example 5 |
| Example 145 | 239 | 1.68–1.78(m, 2H), 2.14–2.24(m, 2H), 2.24(s, 3H), 2.32(s, 3H), 2.36–2.43(m, 2H), 2.53–2.67(m, 8H), 3.30(s, 2H), 4.00(t, J=7.6Hz, 1H), 7.12–7.19(m, 2H), 7.21–7.56(m, 8H). | 28 | Similar to Example 7 |
| Example 146 | 240 | 1.75–1.82(m, 2H), 2.19–2.26(m, 2H), 2.43–2.47(m, 2H), 2.65–2.73(m, 8H), 3.63(s, 2H), 4.01(t, J=7.8Hz, 1H), 7.14–7.19(m, 2H), 7.23–7.29(m, 10H), 8.52(d, J=5.9Hz, 2H). | 50 | Similar to Example 1 |
| Example 147 | 241 | 1.74–1.83(m, 2H), 2.18–2.27(m, 2H), 2.42–2.48(m, 2H), 2.66–2.74(m, 8H), 3.63(s, 2H), 4.00(t, J=7.6Hz, 1H), 7.12–7.30(m, 11H), 7.66(ddd, J=7.9, 2.0, 1.7Hz, 1H), 8.49(dd, J=4.6, 1.7Hz, 1H), 8.53(d, J=2.0Hz, 1H), | 44 | Similar to Example 1 |
| Example 148 | 242 | 1.78–2.00(m, 2H), 2.20–2.31(m, 2H), 2.44–2.52(m, 2H), 2.68–2.82(m, 8H), 3.80(s, 2H), 4.01(t, J=7.6Hz, 1H), 7.12–7.30(m, 11H), 7.43(d, J=7.9Hz 1H), 7.64(ddd, J=7.9, 7.6, 1.7Hz, 1H), 8.53(ddd, J=5.0, 1.7, 1.0Hz, 1H). | 57 | Similar to Example 1 |
| Example 149 | 243 | 1.7–1.83(m, 2H), 2.1–2.25(m, 2H), 2.43(t, J=7.4Hz, 2H), 2.4–2.74(m, 8H), 3.69(s, 2H), 3.75(s, 3H), 3.96(t, J=7.7Hz, 1H), 6.81(d, J=8.9Hz, 2H), 7.16(d, J=8.6Hz, 2H), 7.2–7.35(m, 7H), 8.51(d, J=5.9Hz, 2H). | 32 | Similar to Example 1 |
| Example 150 | 245 | 1.70–1.85(m, 2H), 2.12–2.22(m, 2H), 2.37–2.45(m, 2H), 2.63–2.72(m, 8H), 3.63(s, 2H), 4.00(t, J=7.6Hz, 1H), 7.15–7.29(m, 11H), 7.87(d, J=4.6Hz, 2H). | 8 | Simnilar to Example 1 |
| Example 151 | 258 | 1.80–1.88(dt, J=12.2, 5.9Hz, 2H), 2.40(dd, J=6.0, 5.2Hz, 2H), 2.57–2.74(m, 10H), 3.63(s, 2H), 7.15–7.20(m, 2H), 7.26–7.32(m, 6H), 7.45–7.48(m, 4H), 8.52(dd, J=4.3, 1.6Hz, 2H). | 8 | Similar to Example 1 |

(a) 2-(Trimethylsilyl)ethoxymethyl group was used as protective group.
(b) Compound No. 160 was obtained as the by-product in preparation of compound No. 156.

General Alkylation Procedure of 1-(3-Hydroxy-3,3-diphenylpropyl)homopiperazine for Examples 152–162

A solution of 1-(3-hydroxy-3,3-diphenylpropyl) homopiperazine (0.12 mmol) in 0.5 mL of acetonitrile was treated with alkylating reagent (0.10 mmol) and potassium carbonate (0.15 mmol) and the reaction mixture was heated to 50° C. for 5 h. Polystyrene-linked benzyl isocyanate resin (0.65 mmol/g, 0.05 mmol) and dichloromethane (0.5 mL) was added and the mixture was stirred at room temperature for 1 h. The mixture was filtered and washed with dichloromethane (0.5 mL). The filtrate and washing were combined, and the solvent was removed under reduced pressure to afford the N,N-dialkylated material.

Example 152

Compound No. 174 (65 mg) was prepared by above general alkylation procedure. ESI/MS m/e 493.0 (M$^+$+H, C$_{29}$H$_{36}$N$_2$O$_3$S).

Example 153

Compound No. 175 (51 mg) was prepared by above general alkylation procedure. ESI/MS m/e 507.5 (M$^+$+H, C$_{30}$H$_{38}$N$_2$O$_3$S).

Example 154

Compound No. 176 (48 mg) was prepared by above general alkylation procedure. ESI/MS m/e 507.5 (M$^+$+H, C$_{30}$H$_{38}$N$_2$O$_3$S).

Example 155

Compound No. 177 (51 mg) was prepared by above general alkylation procedure. ESI/MS m/e 521.5 (M$^+$+H, C$_{31}$H$_{40}$N$_2$O$_3$S).

Example 156

Compound No. 178 (56 mg) was prepared by above general alkylation procedure. ESI/MS m/e 541.5 (M$^+$+H, C$_{32}$H$_{36}$N$_2$O$_3$S).

Example 157

Compound No. 179 (41 mg) was prepared by above general alkylation procedure. ESI/MS m/e 479.0 (M$^+$+1, C$_{28}$H$_{34}$N$_2$O$_3$S).

Example 158

Compound No. 180 (42 mg) was prepared by above general alkylation procedure. ESI/MS m/e 493.0 (M$^+$+1, C$_{39}$H$_{36}$N$_2$O$_3$S).

Example 159

Compound No. 181 (42 mg) was prepared by above general alkylation procedure. ESI/MS m/e 507.5 (M$^+$+1, $C_{30}H_{38}N_2O_3S$).

Example 160

Compound No. 182 (53 mg) was prepared by above general alkylation procedure. ESI/MS m/e 507.5 (M$^+$+1, $C_{30}H_{38}N_2O_3S$).

Example 161

Compound No. 183 (40 mg) was prepared by above general alkylation procedure. ESI/MS m/e 521.5 (M$^+$+1, $C_{31}H_{40}N_2O_3S$).

Example 162

Compound No. 184 (52 mg) was prepared by above general alkylation procedure. ESI/MS m/e 541.5 (M$^+$+1, $C_{33}H_{36}N_2O_3S$).

Preparation of 1-(3,3-Diphenylpropyl)homopiperazine

A suspension of homopiperazine (2.9 g, 28.9 mmol) and homopiperazine dihydrochloride (5.0 g. 28.9 mmol) in EtOH was heated to 70° C. for 2 h, at which point a homogeneous solution of monohydrochloride salt (2.5 equiv) was obtained. The reaction mixture was treated with 3,3-diphenylpropyl methanesulfonate (6.7 g, 23.1 mmol, 1 equiv) and NaI (8.65 g, 57.7 mmol, 2.5 equiv) and heated to reflux for 16 h. The reaction mixture was cooled to 25° C. and the solvent was removed in vacuo. The crude product was partitioned between 2N aqueous NaOH (100 mL) and EtOAc (100 mL), and the aqueous layer was extracted with EtOAc (3×50 mL). The combined organic phase was washed with saturated aqueous NaCl (1×100 mL), dried (MgSO$_4$) and concentrated. Chromatography (SiO$_2$, 4×20 cm. 10% CH$_3$OH— 5% Et$_3$N-CH$_2$Cl$_2$) afforded the monoalkylated product (6.44 g, 6.79 g theoretical, 95%) as an amber oil.

General Alkylation of 1-(3,3-Diphenylpropyl)homopiperazine for Examples 163–194

A solution of 1-(3,3-diphenylpropyl)homopiperazine (132 mg, 0.449 mmol) was treated with alkylating reagent (0.492 mmol, 1.1 equiv) and Et$_3$N (75 mL, 0.54 mmol, 1.2 equiv) and the reaction mixture was heated to 70° C. for 16 h. The solvent was removed under vacuum. Chromatography (SiO$_2$, 2×20 cm, 20% CH$_3$OH-EtOAc) afforded the N,N-dialkylated material (10–95%).

Chromatography Methods

HPLC analyses was performed with following methods.
1. Methods A and S.
Column

Method A: Micra Analytical Column (4.6 mm×3.3 cm)
Method B: Monitor C18 column (50 mm×4.6 mm)
Buffer for Methods A and B
Buffer A: 0.05% TFA in H$_2$O
Buffer B: 0.035% TFA in 10% H$_2$O/CH$_3$CN
Gradient 1 (10–11 Min)
1% Buffer B for 0.5 min
1 to 31% Buffer B in 5.0 min
31% to 51% Buffer B in 2.0 min
51% Buffer B for 0.5 min
51% to 1% Buffer B in 0.5 min
1% Buffer B Hold
Gradient 2 (4 Min)
10% Buffer B for 0.5 min
61% Buffer B in 1.8 min
91% Buffer B in 1.5 min
91% Buffer B for 0.8 min
91% to 10% Buffer B in 0.4 min
10% Buffer B Hold
2. Method C
Column
C18 column 4.6 mm
Gradient
1% Buffer B for 3 min
1% to 61% Buffer B in 20 min
61% Buffer B For 4 min
61% to 1% Buffer B in 1 min
1% Buffer B for 5 min—hold

Example 163

Compound No. 265 (82 mg, 39%) was prepared from 1-(3,3-diphenylpropyl)homopiperazine (151.7 mg, 0.513 mmol) and N,N-diethylacetamide (78 mL, 0.567 mmol, 1.1 equiv) employing general alkylation procedure. RPLC $t_R$=4.93 min (90%), 220 nm (Method A); ESI/MS m/e 408.4 (M$^+$+H, $C_{26}H_{37}N_3O$).

Example 164

Compound No. 210 (53 mg. 34%) was prepared from 1-(3,3-diphenylpropyl)homopiperazine (131 mg, 0.446 mmol) and 1-bromo-2-butyne (42 mL, 0.479 mmol, 1.1 equiv) employing general alkylation procedure. RPLC $t_R$=16.18 min (>90%), 220 nm (Method C); ESI/MS m/e 347.2 (M$^+$+H, $C_{24}N_{30}N_2$).

Example 165

Compound No. 211 (102 mg, 75%) was prepared from 1-(3,3-diphenylpropyl)homopiperazine (115 mg, 0.391 mmol) and (bromomethyl)cyclopropane (42 mL, 0.433 mmol, 1.1 equiv) employing general alkylation procedure. RPLC $t_R$=17.91 min (>95%), 220 nm (Method C): ESI/MS m/e 349.4 (M$^+$+H, $C_{24}H_{32}N_2$).

Example 166

Compound No. 266 (150 mg, 95%) was prepared from 1-(3,3-diphenylpropyl)homopiperazine (132 mg, 0.449 mmol) and 2-bromoacetamide (68 mg, 0.492 mmol, 1.1 equiv) employing general alkylation procedure. RPLC $t_R$=6.10 min (90%), 220 nm (Method A). ESI/MS m/e 352.2 (M$^+$+H. $C_{22}H_{29}N_3O$).

Example 167

Compound No. 212 (21 mg. 9%) was prepared from 1-(3,3-diphenylpropyl)homopiperazine (151 mg, 0.513 mmol) and 7-acetoxy-4-(bromomethyl)coumarin (168 mg, 0.565 mmol, 1.1 equiv) employing general alkylation procedure. RPLC $t_R$=5.73 min (>90%), 220 nm (Method A); ESI/MS m/e 469.4 (M$^+$+H. $C_{30}H_{32}N_2O_3$).

Example 168

Compound No. 213 (164 mg, 94%) was prepared from 1-(3,3-diphenylpropyl)homopiperazine (136.6 mg, 0.465 mmol) and 5-bromovaleronitrile (60 mL, 0.511 mmol, 1.1 equiv) employing general alkylation procedure. RPLC $t_R$=17.75 min (>90%), 220 nm (Method C); ESI/MS m/e 376.4 (M$^+$+H, $C_{26}H_{33}N_3$).

Example 169

Compound No. 70 (132 mg, 89%) was prepared from 1-(3,3-diphenylpropyl)homopiperazine (100 mg, 0.340 mmol) and 2-chloro-N-(2,6-diethylphenyl)acetamide (70 mg, 0.310 mmol, 0.9 equiv) employing general alkylation procedure. RPLC $t_R$=6.97 min (88%), 220 nm (Method A): ESI/MS m/e 484.4 (M$^+$+H, $C_{32}H_{41}N_3O$).

Example 170

Compound No. 214 (49 mg, 42%) was prepared from 1-(3,3-diphenylpropyl)homopiperazine (100 mg, 0.340 mmol) and 3-bromopropionitrile (31 mL, 0.374 mmol, 1.1 equiv) employing general alkylation procedure. RPLC $t_R$=4.36 min (>90%), 220 nm (Method A); ESI/MS m/e 348.2 (M$^+$+H, $C_{23}H_{29}N_3$).

Example 171

Compound No. 215 (71 mg, 58%) was prepared from 1-3,3-diphenylpropyl)homopiperazine (100 mg, 0.340 mmol) and 4-bromobutyronitrile (37 mL, 0.374 mmol, 1.1 equiv) employing general alkylation procedure. RPLC $t_R$=3.91 min (86%), 220 nm (Method A); ESI/MS m/e 362.2 (M$^+$+H, $C_{24}H_{31}N_3$).

Example 172

Compound No. 267 (31 mg, 24%) was prepared from 1-(3,3-diphenylpropyl)homopiperazine (100 mg, 0.340 mmol) and N-ethylchloroacetamide (45 mg, 0.374 mmol, 1.1 equiv) employing general alkylation procedure. RPLC $t_R$=4.07 min (91%), 220 nm (Method A); ESI/MS m/e 380.4 (M$^+$+H, $C_{24}H_{33}N_3O$).

Example 173

Compound No. 204 (29 mg, 17%) was prepared from 1-(3,3-diphenylpropyl)homopiperazine (105.4 mg, 0.359 mmol) and methyl 2-[3-(2-chloroethyl)ureido]benzoate (110 mg, 0.394 mmol, 1.1 equiv) employing general alkylation procedure. RPLC $t_R$=4.95 min (>95%), 220 nm (Method A); ESI/MS m/e 483.4 (M$^+$+H, $C_{30}H_{35}N_4O_2$).

Example 174

Compound No. 216 (79 mg, 36%) was prepared from 1-(3,3-diphenylpropyl)homopiperazine (136.7 mg, 0.465 mmol) and Maybridge SPE03660 (108.8 mg, 0.511 mmol, 1.1 equiv) employing general alkylation procedure. RPLC $t_R$=5.83 min (>90%), 220 nm (Method A); ESI/MS m/e 471.4 (M$^+$+H, $C_{29}H_{34}N_4O_2$).

Example 175

Compound No. 246 (59 mg, 33%) was prepared from 1-(3,3-diphenylpropyl)homopiperazine (100 mg, 0.340 mmol) and Maybridge GK02253 (87 mg, 0.374 mmol) employing general alkylation procedure. RPLC $t_R$=5.11 min (>95%), 220 nm (Method A); ESI/MS m/e 491.4 (M$^+$+H, $C_{28}H_{34}N_4O_2S$).

Example 176

Compound No. 217 (66 mg, 58%) was prepared from 1-(3,3-diphenylpropyl)homopiperazine (100 mg, 0.340 mmol) and bromoacetonitrile (26 mL, 0.374 mmol) employing general alkylation procedure. RPLC $t_R$=5.21 min (>95%), 220 nm; ESI/MS m/e 334.4 (M$^+$+H, $C_{22}H_{27}N_3$).

Exmple 177

Compound No. 71 (59 mg, 33%) was prepared from 1-(3,3-diphenylpropyl)homopiperazine (100 mg, 0.340 mmol) and Maybridge CD08063 (100 mg, 0.374 mmol, 1.1 equiv) employing general alkylation procedure. RPLC $t_R$=6.23 min (>85%), 220 nm (Method A); ESI/MS m/e 525.2 (M$^+$+H, $C_{28}H_{33}ClN_4O_2S$).

Example 178

Compound No. 247 (35 mg, 221) was prepared from 1-(3,3-diphenylpropyl)homopiperazine (100 mg, 0.340 mmol) and Maybridge SEW03081 (63 mg, 0.374 mmol) employing general alkylation procedure. RPLC $t_R$=6.20 min (90%), 220 nm (Method A); ESI/MS m/e 427.4 (M$^+$+H, $C_{22}H_{27}ClN_4S$).

Example 179

Compound No. 74 (42 mg, 23%) was prepared from 1-(3,3-diphenylpropyl)homopiperazine (100 mg, 0.340 mmol) and Maybridge S52956 (85 mg, 0.374 mmol) employing general alkylation procedure. RPLC $t_R$=21 min (901), 220 nm (Method A); ESI/MS m/e 486.4 (M$^+$+H, $C_{31}H_{39}N_3O_2$).

Example 180

Compound No. 248 (105 mg, 41%) was prepared from 1-(3,3-diphenylpropyl)homopiperazine (133.5 mg, 0.454 mmol) and Maybridge GK1350 (149 mg, 0.500 mmol, 1.1 equiv) employing general alkylation procedure. RPLC $t_R$=6.60 min (>90%), 220 nm (Method A); ESI/MS m/e 556.4 (M$^+$+H, $C_{32}H_{37}N_5O_2S$).

Example 181

Compound No. 249 (80 mg, 34%) was prepared from 1-(3,3-diphenylpropyl)homopiperazine (126.7 mg, 0.430 mmol) and Maybridge RF00404 (134 mg, 0.474 mmol, 1.1 equiv) employing general alkylation procedure. RPLC $t_R$=5.96 min (>90%), 220 nm (Method A): ESI/MS m/e 540.4 (M$^+$+H, $C_{28}H_{31}Cl_2N_5O_2$).

Example 182

Compound No. 219 (69 mg, 38%) was prepared from 1-(3,3-diphenylpropyl)homopiperazine (100 mg, 0.340 mmol) and Maybridge S07335 (117 mg, 0.408 mmol, 1.2 equiv) employing general alkylation procedure. RPLC $t_R$=4.68 min (>95%), 220 nm (Method A); ESI/MS m/e 526.4 hydrolysis product (M$^+$+H, $C_{36}H_{37}N_3O_2$).

Example 183

Compound No. 269 (20 mg, 13%) was prepared from 1-(3,3-diphenylpropyl)homopiperazine (100 mg, 0.340 mmol) and Maybridge CD07922 (67 mg, 0.374 mmol, 1.1 equiv) employing general alkylation procedure. RPLC $t_R$=4.65 min (90%), 220 nm (Method A): ESI/MS m/e 438.3 (M$^+$+H, $C_{26}H_{36}N_3OS$).

Example 184

Compound No. 250 (24 mg, 19%) was prepared from 1-(3,3-diphenylpropyl)homopiperazine (100 mg, 0.340 mmol) and Maybridge SEW00285 (89 mg) employing general alkylation procedure. RPLC $t_R$=4.70 min (>90%), 220 nm (Method A); ESI/MS m/e 377.3 (M$^+$+H, $C_{23}H_{28}N_4O$).

Example 185

Compound No. 220 (67 mg, 63%) was prepared from 1-(3,3-diphenylpropyl)homopiperazine (100 mg, 0.340 mmol) and propargyl bromide (38 mg, 0.32 mmol) and potassium iodide (0.037 g, 0.22 mmol) employing general alkylation procedure. TLC $R_f$=0.29 (10% $CH_3OH$—$CH_2Cl_2$); RPLC $t_R$=4.21 min (>85%), 220 nm (Method A); ESI/MS m/e 333,3 (M$^+$+H, $C_{23}H_{36}N_2$).

Example 186

Compound No. 221 (51 mg, 32%) was prepared from 1-(3,3-diphenylpropyl)homopiperazine (100 mg, 0.34 mmol) and 1-(3-chloropropyl)-1,3-dihydro-2H-benzimidazol-2-one (85 mg, 0.408 mmol) employing general alkylation procedure. RPLC $t_R$=4.70 min (>97%), 220 nm (Method B); ESI/MS m/e 469.3 (M$^+$+H, $C_{30}H_{36}N_4O$).

Example 187

Compound No. 222 was synthesized from 1-(3,3-diphenylpropyl)homopiperazine (200 mg, 0.680 mmol) and 2-(tert-butyldiphenylsilyl)-3-bromo-2-methyl-1-propanol (125 mg, 0.32 mmol) employing general alkylation procedure. $R_f$ 0.53 (10% $CH_3OH$—$CH_2Cl_2$). The purified intermediate was dissolved in anhydrous THF and treated with tert-butylammonium fluoride (0.35 mL, 0.35 mmol, 1.1 equiv). The reaction mixture was stirred at 25° C. for 2 h and concentrated. Chromatography (SiO$_2$, 40 g, 20% $CH_3OH$-EtOAc) afforded the desired product (30 mg, 30%, two steps). TLC $R_f$ 0.17 (conditions); RPLC $t_R$=4.16 min (>85%), 220 nm (Method B); ESI/MS m/e 367.3 (M$^+$+H, $C_{24}H_{34}N_2O$).

Example 188

Compound No. 75 (91 mg, 65%) was prepared from 1-(3,3-diphenylpropyl)homopiperazine (100 mg, 0.339 mmol) and α-bromo-o-tolunitrile (80 mg, 0.406 mmol) employing general alkylation procedure. RPLC $t_R$=6.52 min (>98%), 220 nm (Method B); ESI/MS m/e 410.3 (M$^+$+H, $C_{28}H_{31}N_3$).

Example 189

Compound No. 76 (63 mg, 37%) was prepared from 1-(3,3-diphenylpropyl)homopiperazine (100 mg, 0.339 mmol) and 2-bromoacetamido-4-nitrophenol (111 mg, 0.406 mmol) employing general alkylatlon procedure. RPLC $t_R$=6.55 min (>98%), 220 nm (Method B); ESI/MS m/e 489.3 (M$^+$+H, $C_{28}H_{32}N_4O_4$).

Example 190

Compound No. 77. (103 mg, 61%) was prepared from 1-(3,3-diphenylpropyl)homopiperazine (100 mg, 0.339 mmol) and ethyl 4-(2-chloroacetamido) benzoate (98 mg, 0.406 mmol) employing general alkylation procedure. RPLC $t_R$=6.52 min (>98%), 220 nm (Method B); ESI/MS m/e 500.3 (M$^+$+H, $C_{31}H_{37}N_4O_3$).

Example 191

Compound No. 223 (84 mg, 49%) was prepared from 1-(3,3-diphenylpropyl)homopiperazine (100 mg, 0.339 mmol) and 1-(3-chloropropyl)theobromine (104 mg, 0.406 mmol) employing general alkylation procedure. RPLC $t_R$=5.25 min (>98%), 220 nm (Method B); ESI/MS m/e 515.3 (M$^+$+H, $C_{30}H_{38}N_6O_2$).

Example 192

Compound No. 80 (81 mg, 47%) was prepared from 1-(3,3-diphenylpropyl)homopiperazine (100 mg, 0.339 mmol) and 4-nitrobenzyl bromoacetate (111 mg, 0.406 mmol) employing general alkylation procedure. RPLC $t_R$=7.35 min (>98%), 220 nm (Method B); ESI/MS m/e 488.3 (M$^+$+H, $C_{29}H_{33}N_3O_4$).

Example 193

Compound No. 81 (139 mg, 921) was prepared from 1-(3,3-diphenylpropyl)homopiperazine (100 mg, 0.339 mmol) and 2-hydroxy-5-nitrobenzyl bromide (90 mg, 0.406 mmol) employing general alkylation procedure. RPLC $t_R$=5.90 min (>95%), 220 nm (Method B); ESI/MS m/e 446.3 (M$^+$+H, $C_{27}H_{31}N_3O_3$).

Example 194

Compound No. 268 (34 mg, 25%) was prepared from 1-(3,3-diphenylpropyl)homopiperazine (100 mg, 0.340 mmol) and N-(chloroacetyl)isopropylamine (51 mg, 0.374 mmol) employing general alkylation procedure. RPLC $t_R$=5.47 min (>90%), 220 nm (Method B); ESI/MS m/e 394.4 (M$^+$+H, $C_{25}H_{35}N_3O$).

General Epozide Opening with 1-(3,3-Diphenylpropyl)homopiperazine for Examples 195–197

A solution of 1-(3,3-diphenylpropyl)homopiperazine (100 mg, 0.340 mmol) in $CH_3CN$ (1.8 mL) was treated with epoxide (0.374 mmol, 1.1 equiv) and $^iPr_2NEt$ (71 mL, 0.41 mmol, 1.2 equiv), and the reaction mixture was heated to 70° C. for 16 h. The solvent was removed under reduced pressure. Chromatography (SiO$_2$, 2×20 cm, 20% $CH_3OH$-EtOAc) afforded the N,N-dialkylated material (23–83%).

Example 195

Compound No. 218 (114 mg, 83%) was prepared from 1-(3,3-diphenylpropyl)homopiperazine (100 mg, 0.340 mmol) and Maybridge NRB00767 (42 mg, 0.375 mmol) employing general epoxide opening procedure. RPLC $t_R$=3.77 min (>85%), 220 nm (Method A); ESI/MS m/e 407.4 (M$^+$+H, $C_{27}H_{36}N_2O_2$).

Example 196

Compound No. 253 (35 mg, 23%) was prepared from 1-(3,3-diphenylpropyl)homopiperazine (100 mg, 0.339 mmol) and furfuryl glycidyl ether (63 mg, 0.406 mmol) employing general epoxide opening procedure. RPLC $t_R$=5.70 min (>98%), 220 nm (Method B); ESI/MS m/e 449.3 (M$^+$+H, $C_{28}H_{36}N_4O_3$).

Example 197

Compound No. 225 (69 mg, 70%) was prepared from 1-(3,3-diphenylpropyl)homopiperazine (40.3 mg, 0.137 mmol) and N-(2,3-epoxypropyl)phthalimide (42.6 mg, 0.150 mmol) employing general epoxide opening procedure. TLC $R_f$=0.40 (10% $CH_3OH$—$CH_2Cl_2$); RPLC $t_R$=5.96 min (>85%), 220 nm (Method B-10 min); ESI/HS m/e 498.3 (M$^+$+H, $C_{31}H_{35}N_3O_3$).

Preparation of N,N-Diethyl-(1-Homopiperazinyl) acetamide

Acetyl chloride (3.90 mL, 54.9 mmol) was dissolved in EtOH (166 mL) and the mixture was stirred for 30 min at 25° C. A solution of homopiperazine (5.0 g. 50 mmol, 1 equiv) in EtOH (20 mL) was added to the reaction mixture in one portion. The flask was fitted with a reflux condenser with a $CaCl_2$ drying tube and the reaction mixture was heated to reflux for 1 h. N,N-Diethylchloroacetamide (3,37 g, 0.5 equiv) was added and the reaction heated to reflux for an additional 16 h. The reaction mixture was allowed to cool and the solvent was removed in vacuo. The product was partitioned between EtOAc (150 mL) and saturated aqueous $NaHCO_3$ (100 mL). The aqueous phase was extracted with EtOAc (1×100 mL). The combined organic phase was dried ($Na_2SO_4$), filtered and concentrated to yield the symmetrically dialkylated material (0.950 g, 17%). The aqueous phase was basicified with 1 M NaOH (100 mL) and was extracted $CH_2Cl_2$ (1×150 mL, 2×100 mL). The combined organic phase was dried ($Na_2SO_4$), filtered and concentrated to afford the pure monoalkylated homopiperazine (2.4 g, 45%).

Preparation of 1-(4-Cyanobenzyl)homopiperazine

To a solution of homopiperazine (9.2 g, 92 mmol, 2 equiv). in EtOH (115 mL) was added 1 M HCl-EtOH (92 mL) dropwise over 1 h. The suspension was heated to 70° C. for 1 h at which point a homogeneous solution of monohydrochloride salt was obtained. α-Bromo-p-tolunitrile (9.0 g, 46 mnmol, 1 equiv) was added and the reaction mixture was heated to reflux for 5 h. After cooling, the solvent was removed by rotary evaporation and the residue was partitioned between $CH_2Cl_2$ (100 mL) and 2N aqueous KOH (100 mL). The aqueous layer was extracted with $CH_2Cl_2$ (5×50 mL) and the combined organic phase was washed with saturated aqueous NaCl (1×150 mL) and dried ($MgSO_4$). Chromatography ($SiO_2$, 4×20 cm, 20% $CH_3OH$ —5% $Et_3N$—$CH_2Cl_2$) afforded the desired monoalkylated material (6.78 g, 10.1 g theoretical, 67%) as an amber oil.

Preparation of 1-[4-(Methylsulfonyl)benzyl] homopiperazine

To a 2-neck, 2-L round bottom flask containing anhydrous EtOH (800 mL) and equipped with a mechanical stirrer and condenser was added acetyl chloride (20.2 mL, 0.267 mol, 1.1 equiv). The solution was stirred for 0.5 h and homopiperazine (24.3 g, 0.243 mol) was added, The mixture was heated to reflux for 2 h. The reaction mixture was cooled to 25° C., 4-(methylsulfonyl)benzyl chloride (25 g, 0.122 mol, 0.5 equiv) was added and the reaction mixture heated to reflux for 16 h. The reaction mixture was cooled to 25° C. and the solvent was removed under vacuum. The residue was diluted with EtOAc (500 mL) and was washed with 2N KOH (2×500 mL). The aqueous layer was extracted with EtOAc (1×500 mL). The organic phase was combined, washed with 2N KOH (1×300 mL), dried ($MgSO_4$) and concentrated. The crude solid was washed with hot EtOAc to yield pure desired product (8.03 g, 32.7 g theoretical, 25%) as an off-white solid, TLC $R_1$ 0.04 (10% $CH_3OH$—$CH_2Cl_2$); $^1H$ NMR ($CDCl_3$, 300 MHz) δ 9.82 (br s, 1H), 7.92 (d, J=8.0 Hz, 2H), 7.60 (d, J=7.7 Hz, 2H), 3.80 (br s, 2H), 3.36 (br m, 2H), 3.07 (s, 3H), 2.93 (br s, 2H), 2.80 (br s, 2H), 2.12 (br m, 2H).

Preparation of 1-(4-Picolyl)homopiperazine

A solution of acetyl chloride (6.34 mL, 0.084 mol, 4 equiv) dissolved in anhydrous EtOH (50 mL) was stirred for 0.5 h and added to a solution of homopiperazine (10.4 g, 0.1 mol, 5 equiv) in EtOH (250 mL). The reaction mixture was heated to reflux for 1 h, cooled to 25° C. and a solution of 4-picolyl chloride hydrochloride 93.44 g, 0.021 mol) in EtOH (40 mL) was added. The reaction mixture was heated to reflux for 16 h, cooled to 25° C. and the solvent was removed under vacuum. The residue was diluted with $CH_2Cl_2$ (300 mL) and was washed with 2N KOH (1×300 mL). The aqueous layer was extracted with $CH_2Cl_2$ (1×300 mL) and the organic phase was washed with 2N KOH (150 mL), dried ($MgSO_4$) and concentrated. Chromatography ($SiO_2$, 5% $H_2O$-5% $NH_4OH$—$^1PrOH$) afforded the desired product (2.88 g, 4.01 g theoretical, 72%) as a yellow oil. TLC $R_f$ 0.45 (5% $H_2O$-5% $NH_4OH$—$^1PrOH$): $^1H$ NMR ($CDCl_3$, 300 MHz) δ 8.77 (d, J=5.9 Hz, 2H), 7.53 (d, J=5.7 Hz, 2H), 3.91 (s, 2H), 3,19 (m, 4H), 2.92 (m, 4H), 2.04 (m, 2H).

Preparation of 1-(4-Chlorobenzyl)homopiperazine

Acetyl chloride (11.7 mL, 0.165 mol) was added to anhydrous EtOH (500 mL) and the mixture was stirred for 30 min at 25° C. Homopiperazine (15.0 g, 0.150 mol) was added and the mixture was heated to reflux for 4 h. 4-Chlorobenzyl chloride (13.96 g, 0.087 mol) was added and the reaction mixture was heated to reflux for 16 h before concentrating. The residue was dissolved in EtOAc (500 mL) and washed with 1N aqueous KOH (50 mL). The aqueous layer was extracted with EtOAc (200 mL). The combined organic layers were dried ($MgSO_4$), filtered and concentrated in vacuo. Chromatography (double separation. $SiO_2$, 20×7 cm, $^1PrOH$—$H_2O$—$NH_4OH$, 80:12:6 to 70:20:10 gradient elution) afforded the desired product (10.6 g, 53.4%) and the dialkylated homopiperazine (2.36 g, 16.5%). GC/MS m/e 224 ($M^+$, $C_{12}H_{17}N_2Cl$).10% $CH_3OH$—$CH_2Cl_2$); RPLC $t_R$=5.96 min (>85%), 220 nm (Mm (Method B): ESI/MS m/e 498.3 ($MH^+$+H, $C_{31}H_{35}N_3O_3$).

Preparation of 1-(4-Methyl-2-thtienyl)-2-(1-homopiperazinylacetyl)hydrazine 1-(tert-butyloxycarbonyl)homopiperazine (1.0 g, 5.0 mmol) in $CH_3CN$ (25 mL) was treated with Maybridge GK 02253 (1.2 g, 5.0 mmol) and $^1Pr_2NEt$ (1.04 mL, 6.0 mmol, 1.2 equiv). The reaction mixture was heated to 70° C. for 16 h. After cooling, the solvent was removed under reduced pressure and the residue was purified by chromatography ($SiO_2$, 4×20 cm, 5% $CH_3OH$—$CH_2Cl_2$) to afford the Boc-protected monoalkylated material as a white foam (1.33 g, 67%). RPLC $t_R$=5.20 min (>98%), 220 nm (Method B); ESI/MS m/e 397.0 ($M^+$+H, $C_{18}H_{38}N_4O_4S$). The product (1.1 g, 2.8 mmol) was dissolved in 3 M HCl—$CH_3OH$ (14 mL) and stirred at 25° C. for 30 min. The solvent was removed by rotary evaporation and the deprotected homopiperazine HCl salt was dissolved in $^tBuOH$-$H_2O$ (3:1, 25 mL). Dowex Anion exchange resin was added until pH=9. The resin was removed by filtration and evaporation afforded the pure mono-alkylated product (703 mg, 86%). RPLC $t_R$=0.78 min (>98%), 220 nm (Method B); ESI/MS m/e 297.1 ($M^+$+H, $C_{14}H_{30}N_4O_2S$).

General Alkylation with 4-Bromo-2,2-diphenylbutyronitrile for Examples 198–203

Monosubstituted homopiperazine (100 mg, 0.468 mmol, 1.0 equiv) in $CH_3CN$ (3 mL) was treated sequentially with 4-bromo-2,2-diphenylbutyronitrile (168 mg, 0.561 mmol, 1.2 equiv) followed by $^1Pr_2NEt$ (60 mg, 0.468 mmol, 1.2 equiv). The reaction mixture was heated to 70° C. with stirring for 16 h. The mixture was allowed to cool and the solvent was removed in vacuo. The product was purified by chromatography (SiO$_2$, 3×5 cm, 20% CH$_3$OH-EtOAC) to afford the desired dialkylated material (48 mg, 24%).

Example 198

Compound No. 264 (48 mg, 24%) was prepared from N,N-diethyl-(1-homopiperazinyl)acetamide (100 mg, 0.468 mmol) and 4-bromo-2,2-diphenylbutyronltrile (168 mg, 0.561 mmol) employing general alkylation procedure. TLC R$_f$=0.30 (20% CH$_3$OH-EtOAc); RPLC t$_R$=4.58 min (>98%), 220 nm (Method B); ESI/MS m/e 433,3 (M$^+$+H, C$_{27}$H$_{36}$N$_4$O).

Example 199

Compound No. 233 (225 mg, 73%) was prepared from 1-(4-picolyl)homopiperazine (200 mg, 1.05 mmol) and 4-bromo-2,2-diphenylbutyronitrile (225 mg, 0.75 mmol) employing general alkylation procedure. TLC R$_f$=0.33 (10% CH$_3$OH—CH$_2$Cl$_2$), RPLC t$_R$=4.27 min (>85%), 220 nm (Method B); ESI/MS m/e 411.3 (MH$^+$+H, C$_{27}$H$_{30}$N$_4$).

Example 200

Compound No. 2 (155 mg, 52%) was prepared from 1-(4-cyanobenzyl)homopiperazine (150 mg, 0.684 mmol) and 4-bromo-2,2-diphenylbutyronitrile (226 mg, 0.752 mmol, 1.1 equiv) employing general alkylation procedure. RPLC t$_R$=4.93 min (85.1%), 220 nm (Method B); ESI/MS m/e 435.3 (M$^+$+H, C$_{29}$H$_{30}$N$_4$).

Example 201

Compound No. 3 (16 mg, 12%) was prepared from 1-(4-chlorobenzyl)homopiperazine (68 mg, 0.30 mmol) and 4-bromo-2,2-diphenylbutyronitrile (100 mg, 0.33 mmol) employing general alkylation procedure. TLC R$_f$=0.32 (5% CH$_3$OH—CH$_2$Cl$_2$); RPLC t$_R$=5.27 min (>85%), 220 nm (Method A); ESI/MS m/e 444.3 (M$^+$+H, C$_{20}$H$_{30}$ClN$_2$).

Example 202

Compound No. 4 (251 mg, 69%) was prepared from 1-[4-(methylsulfonyl)benzyl]homopiperazine (200 mg, 0.75 mmol) and 4-bromo-2,2-diphenylbutyronitrile (270 mg, 0.9 mmol) employing general alkylation procedure. TLC R$_f$=0.53 (10% CH$_3$OH—CH$_2$Cl$_2$); RPLC t$_R$=4.73 min (>85%), 220 nm (Method A); ESI/MS m/e 488.3 (M$^+$+H, C$_{29}$H$_{33}$N$_2$O$_2$S).

Example 203

Compound No. 234 (9 mg, 5%) was prepared from 1-(4-methyl-2-thienyl)-2-(1-homopiperazinylacetyl) hydrazine (95 mg, 0.32 mmol) and 4-bromo-2,2-diphenylbutyronitrile (96 mg, 0.32 mmol) employing general alkylation procedure. RPLC t$_R$=6.03 min (>90%), 220 nm (Method B-10 min); ESI/MS m/e 516.3 (M$^+$+H, C$_{29}$H$_{33}$N$_5$O$_2$S).

Preparation of 1-(4-Cyanobenzyl)piperazine

To a solution of piperazine (5.17 g, 60 mmol, 2 equiv) in EtOH (40 mL) was added 1 M HCl-EtOH (60 mL) dropwise over 1 h and the suspension was heated to 70° C. for 1 h. α-Bromo-p-tolunitrile (5.88 g, 30 mmol, 1 equiv) was added and the reaction was heated to reflux for 16 h. After cooling the solvent was removed by rotary evaporation and the residue was partitioned between CH$_2$Cl$_2$ (70 mL) and 2N aqueous KOH (70 mL) and the combined organic phase was washed with saturated aqueous NaCl (100 mL) and dried (MgSO$_4$). Chromatography (SiO$_2$, 20% CH$_3$OH-5% Et$_3$N-CH$_2$Cl$_2$) afforded the monoalkylated material (2.6 g, 6.0 g theoretical, 43%) as an amber oil.

General Alkylation of 1-(4-Cyanobenzyl)piperazine for Examples 204 and 205

A solution of 1-(4-cyanobenzyl)piperazine (150 mg, 0.745 mmol) was treated with alkylating reagent (0.745 mmol, 1 equiv) and $^1$Pr$_2$NEt (156 mL, 0.894 mmol, 1.2 equiv). The reaction mixture was heated to 70° C. and stirred by vortex for 16 h. After cooling, the reaction mixture was subjected directly to chromatography (SiO$_2$, 3–7% CH$_3$OH—CH$_2$Cl$_2$, gradient elution) to afford the desired N,N-dialkylated piperazine (11–77%).

Example 204

Compound No. 9 (142 mg, 48%) was prepared from 1-(4-cyanobenzyl)piperazine (150 mg, 0.745 mmol) and 3,3-diphenylpropyl methanesulfonate (216 mg, 0.745 mmol, 1 equiv) employing general alkylation procedure. RPLC t$_R$=6.47 min (>95%), 220 nm (Method B); ESI/MS m/e 396.2 (M$^+$+H, C$_{27}$H$_{29}$N$_3$).

Example 205

Compound No. 1 (166 mg, 53%) was prepared from 1-(4-cyanobenzyl)homopiperazine (150 mg, 0.745 mmol) and 4-bromo-2,2-diphenylbutyronltrile (224 mg, 0.745 mmol) employing general alkylation procedure. RPLC t$_R$=6.82 min (>95%), 220 nm (Method B); ESI/MS m/e 422.3 (M$^+$+H, C$_{28}$H$_{28}$N$_4$).

General Preparation of Hydrazide Alkylating Agents

The hydrazide starting material (7.93 mmol) was dissolved in CH$_3$CN (20 mL) and treated with chloroacetyl chloride (0.95 mL, 11.93 mmol, 1.5 equiv) and Et$_3$N (1.11 mL, 7.96 mmol, 1.02 equiv). The mixture was stirred at 25° C. for 16 h and concentrated, The residue was dissolved in EtOAc (300 mL), washed with 1N aqueous HCl (10 mL) saturated aqueous NaCl (20 mL), dried (MgSO$_4$), and concentrated in vacuo. The desired compound was isolated by trituration with EtOAc, followed by washing with hexane or chromatography (SiO$_2$). General alkylation procedure for Example 163–194 was then used to afford the desired homopiperazine analogs,

Example 206

1-Benzoyl-2-(chloroacetyl)hydrazine (850 mg, 54%) was prepared from benzhydrazide (1.00 g, 7.34 mmol) and chloroacetyl chloride (0.58 mL, 7.34 mmol, 1 equiv) using general procedure. Compound No. 78 (300 mg, 51%) was prepared from 1-(3,3-diphenyipropyl)homopiperazine (100 mg, 0.34 mmol) and 1-benzoyl-2-(chloroacetylhydrazine (80 mg, 0.38 mmol) employing general alkylation procedure. TLC R$_f$=0.44 (10% CH$_3$OH—CH$_2$Cl$_2$), RPLC t$_R$=5.85 min (>85%), 220 nm (Method B): ESI/MS m/e 471.3 (M$^+$+H, C$_{29}$H$_{34}$N$_4$O$_2$).

Example 207

1-(Chloroacetyl)-2-(phenylacetyl)hydrazine (1.24 g, 82%) was prepared from phenylacetohydrazide (1.00 g, 6.66 mmol) and chloroacetyl chloride (0.53 mL, 6.66 mmol, 1 equiv) using general procedure. Compound No. 79 (71 mg, 43%) was prepared from 1-(3,3-diphenylpropyl) homopiperazine (100 mg, 0.34 mmol) and 1-(chloroacetyl)-2-(phenylacetyl)hydrazine (85 mg, 0.38 mmol) employing general alkylation procedure. TLC $R_f$=0.40 (10% $CH_3OH$—$CH_2Cl_2$); RPLC $t_R$=6.02 min (>85%), 220 nm (Method 8): ESI/MS m/e 485.5 ($M^++H$, $C_{30}H_{36}N_4O_2$).

Example 208

1-(2-Furoyl)-2-(chloroacetyl)hydrazine (1.21 g, 75%) was prepared from 2-furoic acid hydrazide (1.06 g, 7.93 mmol) and chloroacetyl chloride (0.95 mL, 11.9 mmol, 1.5 equiv) using general procedure. Compound No. 251 (63 mg, 40%) was prepared from 1-(3,3-diphenylpropyl) homopiperazine (100 mg, 0.34 mmol) and 1-(2-furoyl)-2-(chloroacetyl)hydrazine (76 mg, 0.38 mmol) employing general alkylation procedure. TLC $R_f$=0.42 (10% $CH_3OH$—$CH_2Cl_2$); RPLC $t_R$=5.60 min (>85%), 220 nm (Method B): ESI/MS m/e 461.3 ($M^++H$, $C_{27}H_{32}N_4O_3$).

Example 209

1-(2-Thiophenecarbonyl)-2-(chloroacetyl)hydrazine (1.14 g, 74%) was prepared from 2-thiophenecarbohydrazide (1.00 g, 7.03 mmol) and chloroacetyl chloride (0.86 mL, 10.6 mmol, 1.5 equiv) using general procedure. Compound No. 252 (88 mg, 54%) was prepared from 1-(3,3-diphenylpropyl)homopiperazine (100 mg, 0.34 mmol) and 1-(2-Thiophenecarbonyl )-2-(chloroacetyl)hydrazine (82 mg, 0.38 mmol) employing general alkylation procedure. TLC $R_f$=0.47 (10% $CH_3OH$—$CH_2Cl_2$); RPLC $t_R$=5.92 min (>85%), 220 nm (Method B); ESI/MS m/e 477.3 ($M^++H$, $C_{27}H_{32}N_4O_2S$).

Example 210

1-(Diphenylcarbamoyl)-4-(2-chloroacetyl)semicarbazide (1.30 g, 65%) was prepared from 4,4-dlphenylsemicarbazide (1.5 g, 6.60 mmol) and chloroacetyl chloride (0.79 mL, 9.92 mmol, 1.5 equiv) using general procedure. Compound No. 297 (46 mg, 24%) was prepared from 1-(3,3-diphenylpropyl )homopiperazine (100 mg, 0.34 mmol) and 1-(diphenylcarbamoyl)-4(2-chloroacetyl)semicarbazide (114 mg, 0.38 mmol) employing general alkylation procedure. TLC $R_f$=0.44 (10% $CH_3OH$—$CH_2Cl_2$); RPLC $t_R$=6.55 min (>85%), 220 nm (Method B): ESI/MS m/e 562.5 ($M^++H$, $C_{35}H_{39}N_5O_2$).

Example 211

1-(Phenylcarbamoyl)-4-(2-chloroacetyl)semicarbazide (1.19 g, 67%) was prepared from 4-phenylsemicarbazide (1.00 g, 6.62 mmol) and chloroacetyl chloride (0.79 mL, 9.92 mmol) using general procedure. Compound No. 82 (33 mg, 20%) was prepared from 1-(3,3-diphenylpropyl )homopiperazine (100 mg, 0.34 mmol) and 1-(phenylcarbamoyl)-4-(2-chloroacetyl)semicarbazide (85 mg, 0.37 mmol) employing general alkylation procedure. TLC $R_f$=0.41 (10% $CH_3OH$—$CH_2Cl_2$); RPLC $t_R$=5.96 min (>85%), 220 nm (Method B); ESI/MS m/e 486.4 ($M^++H$, $C_{29}H_{35}N_5O_2$).

Example 212

1-(Ethylcarbamoyl)-2-(chloroacetyl)hydrazjne (1.31 g, 76%) was prepared from ethyl carbazate (1.00 g, 9.61 mmol) and chloroacetyl chloride (1.15 mL, 10.16 mmol, 1 equiv) using general procedure. Compound No. 224 (81 mg, 54%) was prepared from 1-(3,3-diphenylpropyl )homopiperazine (100 mg, 0.34 mmol) and 1-(ethylcarbamoyl)-2-(chloroacetyl)hydrazine (68 mg, 0.37 mmol) employing general alkylation procedure. TLC $R_f$=0.44 (10% $CH_3OH$—$CH_2Cl_2$); RPLC $t_R$=5.91 min (>85%), 220 nm (Method B); ESI/MS m/e 439.3 ($M^++H$, $C_{36}H_{36}N_4O_3$).

Example 213

1-(4-Nitrobenzoyl)-2-(chloroacetyl)hydrazine was prepared from $^4$-nitrobenzhydrazide (1.00 g, 5.52 mmol) and chloroacetyl chloride (0.66 mL, 8.29 mmol) using general procedure. Trituration from EtOAc gave the hydrazine in quantitative yield, which was used without further purification. Compound No. 86 (56 mg, 32%) was prepared from 1-(3,3-diphenylpropyl )homopiperazine (100 mg, 0.34 mmol) and 1-(4-nitrobenzoyl)-2-(chlaroacetyllhydrazine (96 mg, 0.37 mmol) employing general alkylation procedure. TLC $R_f$=0.46 (10% $CH_3OH$—$CH_2Cl_2$); RPLC $t_R$=5.56 min (>85%), 220 nm (Method A): ESI/MS m/e 516.3 ($M^++H$, $C_{29}H_{33}N_5O_4$).

Example 214

1-(Toluoyl)-2-(chloroacetyl)hydrazine was prepared from 4-toluic hydrazide (1.00 g, 6.66 mmol) and chloroacetyl chloride (0.80 mL, 9.99 mmol) using general procedure. Trituration from EtOAc gave the hydrazine in quantitative yield, which was used without further purification. Compound No. 87 (61 mg, 37%) was prepared from 1-(3,3-diphenylpropyl)homopiperazine (100 mg, 0.34 mmol) and 1-(toluoyl)-2-(chloroacetyl)hydrazine (74 mg, 0.37 mmol) employing general alkylation procedure. TLC $R_f$=0.44 (10% $CH_3OH$—$CH_2Cl_2$); RPLC $t_R$=5.51 min (>85%), 220 nm (Method A): ESI/MS m/e 485.4 ($M^++H$, $C_{36}H_{36}N_4O_2$).

Example 215

1-(4-Hydroxybenzoyl)-2-(chloroacetyl)hydrazine was prepared from 4-hydroxybenzhydrazide (1.00 g, 6.57 mmol) and chloroacetyl chloride (0.79 mL, 9.92 mmol) using general procedure. Trituration from EtOAc gave the hydrazine in quantitative yield, which was used without further purification. Compound No. 89 (71 mg, 43%) was prepared from 1-(3,3-diphenylpropyl)homopiperazine (100 mg, 0.34 mmol) and 1-(4-hydroxy benzoyl)-2-(chloroacetyl) hydrazine (85 mg, 0.37 mmol) employing general alkylation procedure. RPLC $t_R$=6.21 min (>85%), 220 nm (Method B-10 min); ESI/MS m/e 487.3 ($M^++H$, $C_{29}H_{34}N_4O_3$).

Example 216

1-(2-Nitrobenzoyl)-2-(chloroacetyl)hydrazine (0.579 g, 41%) was prepared from 2-nitrobenzhydrazide (1.00 g, 5.52 mol) and chloroacetyl chloride (0.66 mL, 8.83 mmol) using general procedure. Compound No. 90 (82 mg, 47%) was prepared from 1-(3,3-diphenylpropyl )homopiperazine (100 mg, 0.34 mmol) and 1-(2-nitrobenzoyl)-2-(chloroacetyl) hydrazine (96 mg, 0.37 mmol) employing general alkylation procedure. TLC $R_f$=0.40 (10% $CH_3OH$—$CH_2Cl_2$); RPLC $t_R$=6.04 min (>851), 220 nm (Method B): ESI/MS m/e 516.1 ($M^++H$, $C_{29}H_{33}N_5O_4$).

Example 217

1-(4-Methoxybenzoyl)-2-(chloroacetyl)hydrazine (1.783 g, 54%) was prepared from 4-methoxybenzhydrazide (1.00 g, 6.00 mmol) and chloroacetyl chloride (0.72 mL, 9.00 mmol) using general procedure. Compound No. 92 (63 mg, 51%) was prepared from 1-(3,3-diphenylpropyl) homopiperazine (100 mg, 0.34 mmol) and 1-(4-methoxybenzoyl)-2-(chloroacetyl)hydrazine (91 mg, 0.37 mmol) employing general alkylation procedure. TLC $R_f$=0.52 (10% $CH_3OH$—$CH_2Cl_2$); RPLC $t_R$=5.46 min (>85%), 220 nm (Method A); ESI/MS m/e 501.1 ($M^+$+H, $C_{30}H_{36}N_4O_3$).

Example 218

1-(Nicotinoyl)-2-(chloroacetyl)hydrazine (1.29 g, 83%) was prepared from nicotinohydrazide (1.00 g , 7.29 mmol) and chloroacetyl chloride (0.87 mL, 10.94 mmol) using general procedure. Compound No. 254 (100 mg, 66%) was prepared from 1-(3,3-diphenylpropyl)homopiperazine (100 mg, 0.34 mmol) and 1-(nicotinoyl)-2-(chloroacetyl) hydrazine (87 mg, 0.41 mmol) employing general alkylation procedure. TLC $R_f$=0.12 (10% $CH_3OH$—$CH_2Cl_2$); RPLC $t_R$=5.61 min (93%), 220 nm (Method B); ESI/MS m/e 472.3. ($M^+$+H, $C_{28}H_{33}N_5O_2$).

Example 219

1-(2-Benzo[b]thiophenecarbonyl)-2-(chloroacetyl) hydrazine (0.578 g, 94%) was prepared from (2-benzo[b] thiophenecarbonyl)hydrazine (0.50 g, 2.60 mmol) and chloroacetyl chloride (0.31 mL, 3,90 mmol) using general procedure. Compound No. 255 (73 mg, 41%) was prepared from 1-(3,3-diphenylpropyl)homopiperazine (100 mg, 0.34 mmol) and 1-(2-benzo[b]thiophenecarbonyl)-2-(chloroacetyl)hydrazine (88 mg, 0.37 mmol) employing general alkylation procedure. TLC $R_f$=0.26 (10% $CH_3OH$—$CH_2Cl_2$)); RPLC $t_R$=6.96 min (>85%), 220 nm (Method B); ESI/MS m/e 527.3 ($M^+$+H, $C_{33}H_{34}N_4O_2S$).

Example 220

1-(4-Bromobenzoyl)-2-(chloroacetyl)hydrazine (0.886 g, 73%) was prepared from 4-bromobenzhydrazide (1.00 g, 4.64 mmol) and chloroacetyl chloride (0.55 mL, 6.90 mmol) using general procedure. Compound No.98 (143 mg, 76%) was prepared from 1-(3,3-diphenylpropyl)homopiperazine (100 mg, 0.34 mmol) and 1-(4-bromobenzoyl)-2-(chloroacetyl)hydrazine (98 mg, 0.37 mmol) employing general alkylatlon procedure. TLC $R_f$=0.50 (10% $CH_3OH$—$CH_2Cl_2$); RPLC $t_R$=6.76 min (>85%), 220 nm (Method B); ESI/MS m/e 551.0 ($M^+$+H, $C_{29}H_{33}N_4O_2Br$).

Preparation of Sodium [4-(3,3-Diphenylpropyl)homopiperazine-1-yl]acetate 1-(3,3-Diphenylpropyl)homopiperazine (2.0 g, 6.79 mmol) was dissolved in $CH_3CN$ (60 mL) and treated with methyl bromoacetate (1.56 g, 10.18 mmol) and $Et_3N$ (1.42 mL, 10.18 mmol). The mixture was refluxed for 18 h and subsequently concentrated in vacuo. The residue was subjected to flash silica gel column chromatography (eluent: $CH_2Cl_2$/MeOH, 96/4, v/v) to give Methyl [4-(3,3-diphenylpropyl)homopiperazine-1-yl]acetate (1.93 g) in 78% yield, TLC $R_f$=0.53 (10% $CH_3OH$—$CH_2Cl_2$); RPLC $t_R$=4.71 min (>85%), 220 nm (Method A); ESI/MS m/e 367.1 ($M^+$+H, $C_{23}H_{30}N_2O_2$).

Methyl [4-(3,3-diphenylpropyl)homopiperazine-1-yl] acetate (0.327 g, 0.89 mmol) was dissolved in a mixture of dioxane (3.1 mL). MeOH (1.1 mL) and 4N NaOH (0.22 mL). After stirring for 30 min. 5 more drops of 4N NaOH were added and stirring was, continued until hydrolysis of the methyl ester was complete. The mixture was concentrated in vacuo and the residue subjected to flash silica gel column chromatography (eluent: $CH_2Cl_2$/MeOH, 1/1, v/v) to give sodium [4-(3,3-diphenylpropyl)homopiperazine-1-yl]acetate (0.278 g) in 88% yield, TLC $R_f$=0.22 (10% $CH_3OH$—$CH_2Cl_2$); RPLC $t_R$=1.98 min (>85%), 220 nm (Method B); ESI/MS m/e 353.3 ($M^+$+H, $C_{22}H_{29}N_2O_2$).

General Procedure for Coupling to Sodium [4-(3,3-Diphenylpropyl)homopiperazine-1-yl]acetate for Examples 221–253

Sodium [4-(3,3-diphenylpropyl)homopiperazine-1-yl] acetate (30 mg, 0.08 mmol) was suspended in dry $CH_2Cl_2$ (1 mL) and HOBt (12 mg, 0.089 mmol) and the amine, hydrazide or amino acid (0.88 mmol) were added. After cooling the mixture to 0° C., EDCI (30 mg, 0.10 mmol) was added, the pH adjusted to 7–8 with $Et_3N$ and the mixture was stirred for 15 min at 0° C. and 16 h at rt. Concentration in vacuo of the mixture gave a residue which was not worked up but purified directly by HPLC.

Example 221

Compound No. 270 (55.6 mg, 70%) was prepared from sodium sodium [4-(3,3-diphenylpropyl)homopiperazine-1-yl]acetate (53.6 mg, 0.15 mmol) and dihexylamine (39 mL, 0.167 mmol) employing general coupling procedure. TLC $R_f$=0.46 (10% $CH_3OH$—$CH_2Cl_2$); RPLC $t_R$=8.27 min (>85%), 220 nm (Method B); ESI/MS m/e 520.6 ($M^+$+H, $C_{34}H_{53}N_3O$).

Example 222

Compound No. 83 (30 mg, 39%) was prepared sodium sodium [4-(3,3-diphenylpropyl)homopiperazine-1-yl] acetate (60.2 mg, 0.17 mmol) and benzylhydrazine dihydrochloride (40 mg, 0.205 mmol) employing general coupling procedure. TLC $R_f$=0.39 (10% $CH_3OH$—$CH_2Cl_2$); RPLC $t_R$=6.16 min (>85%), 220 nm (Method B); ESI/MS m/e 457.3 ($M^+$+H, $C_{29}H_{36}N_4O$).

Example 223

Methyl 2-benzoylhydrazinoacetate (0.418 g, 27%) was prepared from benzhydrazide (1.00 g, 7.34 mmol) and methyl bromoacetate (0.76 mL, 80.3 mmol) employing general procedure. Compound No. 84 (37 mg, 44%) was prepared from sodium [4-(3,3-diphenylpropyl) homopiperazine-1-yl]acetate (56 mg, 0.158 mmol) and methyl 2-benzoylhydrazinoacetate (36 mg, 0.17 mmol) employing general coupling procedure. TLC $R_f$=0.49 (10% $CH_3OH$—$CH_2Cl_2$); RPLC $t_R$=6.21 min (>85%), 220 nm (Method B): ESI/MS m/e 543.1 ($M^+$+H, $C_{32}H_{38}N_4O_4$).

Example 224

Compound No. 85 (59 mg, 75%) was prepared from sodium [4-(3,3-diphenylpropyl)homopiperazine-1yl]acetate (62 mg, 0.166 mmol) and 2-aminoacetophenone hydrochloride (33 mg, 0.195 mmol) employing general coupling procedure. TLC $R_f$=0.40 (10% $CH_3OH$—$CH_2Cl_2$); RPLC $t_R$=5.51 min (>85%), 220 nm (Method A): ESI/MS m/e 470.3 ($M^+$+H, $C_{30}H_{35}N_3O_2$).

Example 225

Compound No. 88 (41 mg, 58%) was prepared from sodium [4-(3,3-diphenylpropyl)homopiperazine-1-yl] acetate (50 mg, 0.14 mmol) and 4-chlorobenzhydrazide (27 mg, 0.156 mmol) employing general coupling procedure. RPLC $t_R$=5.71 min (>85%), 220 nm (Method A): ESI/MS m/e 505.2 ($M^+$+H, $C_{29}H_{33}N_4O_2Cl$).

Example 226

Compound No. 91 (55 mg, 68%) was prepared from sodium [4-(3,3-diphenylpropyl)homopiperazine-1-yl]

acetate (60 mg, 0.16 mmol) and 2-amino-4'-methoxyacetophenone hydrochloride (36 mg, 0.176 mmol) employing general coupling procedure. TLC $R_f$=0.55 (10% $CH_3OH$—$CH_2Cl_2$); RPLC $t_R$=6.50 min (>85%), 220 nm (Method B); ESI/MS m/e 500.2 ($M^+$+H, $C_{31}H_{37}N_3O_3$).

Example 227

Compound No. 271 (51 mg, 73%) was prepared from sodium [4-(3,3-diphenylpropyl)homopiperazine-1-yl]acetate (60 mg, 0.16 mmol) and dipropylamine (24 mL, 0.176 mmol) employing general coupling procedure. TLC $R_f$=0.56 (10% $CH_3OH$—$CH_2Cl_2$); RPLC $t_R$=5.51 min (>85%), 220 nm (Method A); ESI/MS m/e 436.3 ($M^+$+H, $C_{28}H_{41}N_3O$).

Example 228

Compound No. 186 (34 mg, 23%) was prepared from sodium [4-(3,3-diphenylpropyl)homopiperazine-1-yl]acetate (100 mg, 0.267 mmol) and benzenesulfonohydrazide (54 mg, 0.31 mmol) employing general coupling procedure. TLC $R_f$=0.47 (10% $CH_3OH$—$CH_2Cl_2$); RPLC $t_R$=6.31 min (87%), 220 nm (Method B); ESI/MS m/e 507.5 ($M^+$+H, $C_{28}H_{34}N_4O_3S$).

Example 229

Compound No. 93 (79 mg, 81%) was prepared from sodium [4-(3,3-diphenylpropyl)homopiperazine-1-yl]acetate (75 mg, 0.20 mmol) and 4-aminobenzhydrazide (34 mg, 0.22 mmol) employing general coupling procedure. TLC $R_f$=0.26 (10% $CH_3OH$—$CH_2Cl_2$); RPLC $t_R$=5.61 min (>85%), 220 nm (Method B); ESI/MS m/e 486.3 ($M^+$+H, $C_{29}H_{35}N_5O_2$).

Example 230

Compound No. 94 (24.4 mg, 17%) was prepared from sodium [4-(3,3-diphenylpropyl)homopiperazine-1-yl]acetate (100 mg, 0.267 mmol) and 4-methoxybenzenesulfonohydrazide (59.4 mg, 0.29 mmol) employing general coupling procedure; TLC $R_f$=0.45 (10% $CH_3OH$—$CH_2Cl_2$); RPLC $t_R$=6.71 min (>85%), 220 nm (Method B); ESI/MS m/e 537.3 ($M^+$+H, $C_{29}H_{36}N_4O_4S$).

Example 231

Compound No. 95 (27.9 mg, 20%) was prepared from sodium [4-(3,3-diphenylpropyl)homopiperazine-1-yl]acetate (100 mg, 0.267 mmol) and p-toluenesulfonohydrazide (55 mg, 0.295 mmol) employing general coupling procedure. TLC $R_f$=0.52 (10% $CH_3OH$—$CH_2Cl_2$); RPLC $t_R$=6.91 min (>85%), 220 nm (Method B); ESI/MS m/e 521.3 ($M^+$+H, $C_{29}H_{36}N_4O_3S$).

Example 232

Compound No. 272 (34 mg, 65%) was prepared from sodium [4-(3,3-diphenylpropyl)homopiperazine-1-yl]acetate (30 mg, 0.08 mmol) and glycine methyl ester hydrochloride (10.6 mg, 0.084 mmol) employing general coupling procedure. TLC $R_f$=0.42 (10% $CH_3OH$—$CH_2Cl_2$); RPLC $t_R$=6.96 min (>851), 220 nm (Method B); ESI/MS m/e 424.3 ($M^+$+H, $C_{25}H_{33}N_3O_3$).

Example 233

Compound No. 273 (37 mg, 72%) was prepared from sodium [4-(3,3-diphenylpropyl)homopiperazine-1-yl]acetate (30 mg, 0.08 mmol) and glycinamide hydrochloride (9.3 mg, 0.084 mmol) employing general coupling procedure. TLC $R_f$=0.32 (10% $CH_3OH$—$CH_2Cl_2$); RPLC $t_R$=5.76 min (>85%), 220 nm (Method B); ESI/MS m/e 409.3 ($M^+$+H, $C_{24}H_{32}N_4O_2$).

Example 234

Compound No. 274 (24 mg, 47%) was prepared sodium [4-(3,3-diphenylpropyl)homopiperazine-1-yl]acetate (30 mg, 0.08 mmol) and glycine tert-butyl ester hydrochloride (14.1 mg, 0.084 mmol) employing general coupling procedure. This compound was purified by diluting with $CH_2C_2$, washing with $NaHCO_3$, brine, drying ($MgSO_4$), filtering and evaporating off the solvent in vacuo. Final purification by silica gel column chromatography. TLC $R_f$=0.41 (10% $CH_3OH$—$CH_2Cl_2$); RPLC $t_R$=6.56 min (>85%), 220 nm (Method B): ESI/MS m/e 466.5 ($M^+$+H, $C_{28}H_{39}N_3O_3$).

Example 235

Compound No. 275 (26.9 mg, 43%) was prepared from sodium [4-(3,3-diphenylpropyl)homopiperazine-1-yl]acetate (30 mg, 0.08 mmol) and (D)-(–)-2-phenylglycinol (13.2 mg, 0.096 mmol) employing general coupling procedure. TLC $R_f$=0.42 (10% $CH_3OH$—$CH_2Cl_2$); RPLC $t_R$=6.21 min (>85%), 220 nm (Method B); ESI/MS m/e 472.0 ($M^+$+H, $C_{30}H_{37}N_3O_2$).

Example 236

Compound No. 226 (27.0 mg, 43%) was prepared from sodium [4-(3,3-diphenylpropyl)homopiperazine-1-yl]acetate (30 mg, 0.08 mmol) and (1S,2R)-(–)-cis-1-amino-2-indanol (14.3 mg, 0.096 mmol) employing general coupling procedure. TLC $R_f$=0.42 (10% $CH_3OH$—$CH_2Cl_2$); RPLC $t_R$=6.36 min (>85%), 220 nm (Method B); ESI/MS m/e 484.0 ($M^+$+H, $C_{32}H_{37}N_3O_2$).

Example 237

Compound No. 276 (24.9 mg, 20%) was prepared from sodium [4-(3,3-diphenylpropyl)homopiperazine-1-yl]acetate (30 mg, 0.08 mmol) and (1R, 2S)-(+)-cis-1-amino-2-indanol (14.3 mg, 0.096 mmol) employing general coupling procedure. TLC $R_f$=0.42 (10% $CH_3OH$—$CH_2Cl_2$); RPLC $t_R$=6.26 min (>85%), 220 nm (Method B); ESI/MS m/e 484.0 ($M^+$+H, $C_{31}H_{37}N_3O_2$).

Example 238

Compound No. 277 (29.9 mg, 43%) was prepared sodium [4-(3,3-diphenylpropyl)homopiperazine-1-yl]acetate (30 mg, 0.08 mmol) and dl-octopamine hydrochloride (18.2 mg, 0.096 mmol) employing general coupling procedure. TLC $R_f$=0.24 (10% $CH_3OH$—$CH_2Cl_2$); RPLC $t_R$=5.76 min (95%), 220 nm (Method B); ESI/MS m/e 488.0 ($M^+$30 H, $C_{30}H_{37}N_3O_2$).

Example 239

Compound No. 278 (28.3 mg, 43%) was prepared from sodium [4-(3,3-diphenylpropyl)homopiperazine-1-yl]acetate (30 mg, 0.08 mmol) and dl-norphenylephrine hydrochloride (18.2 mg, 0.38 mmol) employing general coupling procedure. TLC $R_f$=0.24 (10% $CH_3OH$—$CH_2Cl_2$); RPLC $t_R$=5.91 min (>85%), 220 nm (Method B); ESI/MS m/e 488.0 ($M^+$+H, $C_{30}H_{37}N_3O_3$).

Example 240

Compound No. 279 (27.7 mg, 43%) was prepared from sodium [4-(3,3-diphenylpropyl)homopiperazine-1-yl]

acetate (30 mg, 0.08 mmol) and (1S,2S)-(+)-2-amino-3-methoxy-1-phenyl-1-propanol (17.4 mg, 0.096 mmol) employing general coupling procedure. TLC $R_f$=0.46 (10% $CH_3OH$—$CH_2Cl_2$); RPLC $t_R$=6.36 min (>85%), 220 nm (Method B); ESI/MS m/e 516.0 (M$^+$+H, $C_{32}H_{41}N_3O_3$).

Example 241

Compound No. 280 (29.9 mg, 43%) was prepared from sodium [4-(3,3-diphenylpropyl)homopiperazine-1-yl] acetate (30 mg, 0.08 mmol) and norephedrine hydrochloride (18.0 mg, 0.096 mmol) employing general coupling procedure. TLC $R_f$=0.46 (10% $CH_3OH$—$CH_2Cl_2$); RPLC $t_R$=6.06 min (>85%), 220 nm (Method B); ESI/MS m/e 486.3 (M$^+$+H, $C_{31}H_{39}N_3O_2$).

Example 242

Compound No. 281 (22.4 mg, 20%) was prepared from sodium [4-(3,3-diphenylpropyl)homopiperazine-1-yl] acetate (30 mg, 0.08 mmol) and 2-amino-1-phenyrethanol (16.2 mg, 0.118 mmol) employing general coupling procedure. TLC $R_f$=0.53 (10% $CH_3OH$—$CH_2Cl_2$); RPLC $t_R$=6.11 min (>85%), 220 nm (Method B); ESI/MS m/e 472.3 (M$^+$+H, $C_{30}H_{37}N_3O_2$).

Example 243

Compound No. 298 (26.9 mg, 43%) was prepared from sodium [4-(3,3-diphenylpropyl)homopiperazine-1-yl] acetate (30 mg, 0.08 mmol) and 2-amino-1,3-propanediol (11.0 mg, 0.121 mmol) employing general coupling procedure. TLC $R_f$=0.16 (10% $CH_3OH$—$CH_2Cl_2$); RPLC $t_R$=5.51 min (>85%), 220 nm (Method B); ESI/MS m/e 426.0 (M$^+$+H, $C_{25}H_{35}N_3O_3$).

Example 244

Compound No. 282 (26.9 mg, 43%) was prepared from sodium [4-(3,3-diphenylpropyl)homopiperazine-1-yl] acetate (30 mg, 0.08 mmol) and L-phenylalaninol (17.8 mg, 0.118 mmol) employing general coupling procedure. TLC $R_f$=0.53 (10% $CH_3OH$—$CH_2Cl_2$); RPLC $t_R$=6.31 min (>85%), 220 nm (Method B); ESI/MS m/e 486.3 (M$^+$+H, $C_{32}H_{38}N_4O_2$).

Example 245

Compound No. 283 (27.0 mg, 46%) was prepared from sodium [4-(3,3-diphenylpropyl)homopiperazine-1-yl] acetate (30 mg, 0.08 mmol) and DL-phenylalaninamide hydrochloride (19.3 mg, 0.096 mmol) employing general coupling procedure. TLC $R_f$=0.25 (10% $CH_3OH$—$CH_2Cl_2$); RPLC $t_R$=2.16 min (>85%), 220 nm (Method B); ESI/MS m/e 499.4 (M$^+$+H, $C_{31}H_{38}N_4O_2$).

Example 246

Compound No. 284 (24 mg, 42%) was prepared from sodium [4-(3,3-diphenylpropyl)homopiperazine-1-yl] acetate (30 mg, 0.08 mmol) and DL-aspartic acid dimethyl ester hydrochloride (19.0 mg, 0.096 mmol) employing general coupling procedure. TLC $R_f$=0.46 (10% $CH_3OH$—$CH_2C_2$); RPLC $t_R$=2.16 min (>85%), 220 nm (Method B -); ESI/MS m/e 496.4 (M$^+$+H, $C_{28}H_{37}N_3O_5$).

Example 247

Compound No. 285 (32.4 mg, 49%) was prepared from sodium [4-(3,3-diphenylpropyl)homopiperazine-1-yl] acetate (30 mg, 0.08 mmol) and DL-phenylalanine benzyl ester p-toluenesulfonic acid salt (34.3 mg, 0.08 mmol) employing general coupling procedure. TLC $R_f$=0.53 (10% $CH_3OH$—$CH_2Cl_2$); RPLC $t_R$=2.53 min (>85%), 220 nm (Method B); ESI/MS m/e 590.6 (M$^+$+H, $C_{38}H_{43}N_3O_3$).

Example 248

Compound No. 286 (22.5 mg, 40%) was prepared from sodium [4-(3,3-diphenylpropyl)homopiperazine-1-yl] acetate (30 mg, 0.08 mmol) and DL-leucine methyl ester hydrochloride (17.5 mg, 0.096 mmol) employing general coupling procedure. , TLC $R_f$=0.53 (10% $CH_3OH$—$CH_2Cl_2$); RPLC $t_R$=2.21 min (>85%), 220 nm (Method B); ESI/MS m/e 480.5 (M$^+$+H, $C_{29}H_{41}N_3O_3$).

Example 249

Compound No. 287 (23 mg, 20%) was prepared from sodium [4-(3,3-diphenylpropyl)homopiperazine-1-yl] acetate (30 mg, o.08 mmol) and DL-tyrosine methyl ester hydrochloride (22.3.0 mg, 0.096 mmol) employing general coupling procedure. RPLC $t_R$=2.01 min (>85%), 220 nm (Method B); ESI/MS m/e 530.2 (M$^+$+H, $C_{32}H_{39}N_3O_4$).

Example 250

Compound No. 288 (23.8 mg, 43%) was prepared from sodium [4-(3,3-diphenylpropyl)homopiperazine-1-yl] acetate (30 mg, 0.08 mmol) and DL-methionine methyl ester hydrochloride (19.2 mg, 0.096 mmol) employing general coupling procedure. RPLC $t_R$=2.01 min (>85%), 220 nm (Method B); ESI/MS m/e 498.2 (M$^+$+H, $C_{28}H_{39}N_3O_3S$).

Example 251

Compound No. 289 (21.6 mg, 30%) was prepared from sodium [4-(3,3-diphenylpropyl)homopiperazine-1-yl] acetate (30 mg, 0.08 mmol) and DL-Tryptophan methyl ester hydrochloride (24.5 mg, 0.096 mmol) employing general coupling procedure, RPLC $t_R$=2.27 min (>85%), 220 nm (Method B); ESI/MS m/e 553.4 (M$^+$+H, $C_{34}H_{41}N_3O_2$).

Example 252

Compound No. 299 (20.9 mg, 43%) was prepared from sodium [4-(3,3-diphenylpropyl)homopiperazine-1-yl] acetate (30 mg, 0.08 mmol) and (1S,2R)-(+)-2-amino-1,2-diphenylethanol (20.5 mg, 0.096 mmol) employing general coupling procedure. RPLC $t_R$=2.12 min (>85%), 220 nm (Method B); ESI/MS m/e 548.4 (M$^+$+H, $C_{36}H_{41}N_3O_2$).

Example 253

Compound No. 291 (23.8 mg, 41%) was prepared from sodium [4-(3,3-diphenylpropyl)homopiperazine-1-yl] acetate (30 mg, 0.08 mmol) and DL-methionine methyl ester hydrochloride (19.2 mg, 0.096 mmol) employing general coupling procedure. RPLC $t_R$=2.21 min (>85%), 220 nm (Method B); ESI/MS m/e 484.4 (M$^+$+H, $C_{27}H_{37}N_3O_3S$).

Preparation of [4-(3,3-Dlphenylpropyl)-1-homopiperazinyl]acetobydrazide

Methyl [4-(3,3-diphenylpropyl)-1-homopiperazinyl] acetate (0.607 g, 1.66 mmol) was dissolved in ethanol (20 mL) and hydrazine hydrate (1 mL) was added, The mixture was refluxed for 19 h and subsequently concentrated in vacuo. The residue was taken up in EtOAc. washed with brine, dried (MgSO$_4$) and concentrated in vacuo to afford the title compound as an oil (0.547 g) in 90% yield, TLC $R_f$=0.35 (10% $CH_3OH$—$CH_2Cl_2$); RPLC $t_R$=1.93 min (>85%), 220 nm (Method B); ESI/MS m/e 367.1 (M$^+$+H, $C_{22}H_{30}N_4O$).

General Coupling Procedure for (4-(3,3-Diphenylpropyl)-1-hamopiperazinyl]acatohydrazide for Examples 254–256

[4-(3,3-Diphenylpropyl)-1-homopiperazinyl] acetohydrazide (60.5 mg, 0.165 mmol) was dissolved in dry $CH_2Cl_2$ (2 mL) and $CH_3CN$ (0.5 mL). Pyridine (19 mL, 0.23 mmol) and the sulfonyl chloride (0.195 mmol) were added and the mixture was stirred at room temperature for 16 h. After concentration of the mixture in vacuo, flash silica gel column chromatography was used to isolate the desired product.

Example 254

Compound No. 96 (69 mg, 70%) was prepared from [4-(3,3-Diphenylpropyl)-1-homopiperazinyllacetohydrazide (65 mg, 0.177 mmol) and N-acetylsulfanilyl chloride (46 mg, 0.195 mmol) employing general coupling procedure. TLC $R_f$=0.35 (10% $CH_3OH$—$CH_2Cl_2$); RPLC $t_R$=6.36 min (>85%), 220 nm (Method B); ESI/MS m/e 564.3 ($M^+$+H, $C_{30}H_{37}N_5O_4S$).

Example 255

Compound No. 97 (63.5 mg, 71%) was prepared from [4-(3,3-Diphenylpropyl)-1-homopiperazinyl] acetohydrazide (60.5 mg, 0.165 mmol) and 4-chlorobenzenesulfonyl chloride (38.3 mg, 0.181 mmol) employing general coupling procedure. RPLC $t_R$=7.01 min (>85%), 220 nm (Method B); ESI/MS m/e 541.3 ($M^+$+H, $C_{28}H_{33}N_4O_3SCl$).

Example 256

Compound No. 256 (40 mg, 53%) was prepared from [4-(3,3-Diphenylpropyl)-1-homopiperazinyl] acetohydrazide (55 mg, 0.15 mmol) and 2-thiophenesulfonyl chloride (30 mg, 0.164 mmol) employing general coupling procedure., RPLC $t_R$=6.61 min (>85%), 220 nm (Method B); ESI/MS m/e 513.3 ($M^+$+H, $C_{26}H_{32}N_4O_3S_2$).

Example 257

Compound No. 99 (55 mg, 64%) was prepared by dissolving [4-(3,3-Diphenylpropyl)-1-homopiperazinyl] acetohydrazide (51 mg, 0.139 mmol) in dry $CH_2Cl_2$ (2 mL) and adding HOBt (21 mg, 0.155 mmol) and 4-(methylsulfonyl)benzoic acid (29 mg, 0.146 mmol). This mixture was cooled (0° C.) and treatede with EDCI (45 mg, 0.151 mmol) followed by $Et_3N$ such that the pH was around 8. After stirring for 16 h at room temperature, the mixture was diluted with $CH_2Cl_2$, washed with saturated $NaHCO_3$, brine, dried ($MgSO_4$), filtered and concentrated in vacuo. The residue was applied to silica gel column chromatography (eluent: gradient of 96/4 to 94/6 $CH_2Cl_2$/MeOH, v/v) to afford the desired compound, TLC $R_f$=0.45 (10% $CH_3OH$—$CH_2Cl_2$); RPLC $t_R$=6.06 min (>85%), 220 nm (Method B); ESI/MS m/e 549.3 ($M^+$+H, $C_{38}H_{36}N_4O_4S$).

Example 258

Compound No. 100 (45 mg, 64%) was prepared by dissolving [4-(3,3-Diphenylpropyl)-1-homopiperazinyl] acetohydrazide (49 mg, 0.134 mmol) in dry $CH_2Cl_2$ (2 mL) and adding HOBt (20 mg, 0.148 mmol) and 4-acetylbenzoic acid (23 mg, 0.14 mmol). This mixture was cooled (0° C.) and treated with EDCI (44 mg, 0.148 mmol) followed by $Et_3N$ such that the pH was around 8. After stirring for 16 h at room temperature, the mixture was diluted with $CH_2Cl_2$, washed with saturated $NaHCO_3$, brine, dried ($MgSO_4$), filtered and concentrated in vacuo. The residue was applied to silica gel column chromatography (eluent: gradient of 96/4 to 94/6 $CH_2Cl_2$/MeOH, v/v) to afford the desired compound, TLC $R_f$=0.46 (10% $CH_3OH$—$CH_2Cl_2$); RPLC $t_R$=6.26 min (>85%), 220 nm (Method B). ESI/MS m/e 513.3 ($M^+$+H, $C_{31}H_{36}N_4O_3$).

Example 259

Compound No. 290 (6.6 mg, 64%) was prepared by treatment of Compound No. 286 (10.5 mg, 0.015 mmol) with 0.44 mL of 0.25 N LiOH (MeOH/$H_2O$, 3/1, v/v) at room temperature for 16 h. After acidifying the reaction mixture with TFA and evaporating off the solvents, the residue was purified using a small C-18 column (eluent: water followed by MeOH), RPLC $t_R$=2.28 min (>85%), 220 nm (Method B); ESI/MS m/e 466.4 ($M^+$+H, $C_{28}H_{39}N_3O_3$).

Example 260

Compound No. 292 (6.0 mg, 64%) was prepared by treatment of Compound No. 289 (9.6 mg, 0.0123 mmol) with 0.35 mL of 0.25 N LiOH (MeOH/$H_2O$, 3/1, v/v) at room temperature for 16 h. After acidifying the reaction mixture with TFA and evaporating off the solvents, the residue was purified using a small C-18 column (eluent: water followed by MeOH), RPLC $t_R$=2.41 min (>85%), 220 nm (Method B); ESI/MS m/e 539.3 ($M^+$+H, $C_{33}H_{38}N_4O_3$).

Example 261

Preparation of Compound No. 69

A solution of 1-[4-(methylsulfonyl )benzyl] homopiperazine (314 mg, 1.17 mmol) in $CH_3CN$ (50 mL) was treated sequentially with 3-[4-(tert-butoxycarbonyl)phenyl]-3-phenylpropyl methanesulfonate (456 mg, 1.17 mmol, 1 equiv) and $Na_2CO_3$ (124 mg, 1.17 mmol, 1 equiv). The reaction mixture was heated to 70° C. for 16 h, cooled to 25° C. filtered and concentrated. Chromatography ($SiO_2$, 2×20 cm, 5% $CH_3OH$—$CH_2Cl_2$) afforded the desired material (346 mg, 53%) RPLC $t_R$=7.63 min (>90%), 220 nm (Method A); ESI/MS m/e 563.2 ($M^+$+H, $C_{33}H_{42}N_2O_4S$).

Example 262

Preparation of Compound No. 72 and 73

A solution of compound No. 69 (278 mg, 0.494 mmol) in $CH_3OH$ (2 mL) was treated with a 1.0 M solution of HCl-$Et_2O$ (5 mL) and stirred at 25° C. for 1 h. Concentration and chromatography ($SiO_2$, 2×20 cm, 5% $CH_3OH$—$CH_2Cl_2$ to $CH_3OH$, gradient elution) afforded the compound No. 72 (132 mg, 51%) and compound No. 73 (88 mg, 35%). Compound No. 72; RPLC $t_R$=4.78 min (>90%), 220 nm (Method A); ESI/MS m/e 521.2 ($M^+$+H, $C_{30}H_{36}N_2O_4S$). For compound No. 73; RPLC $t_R$=4.08 min (>95%), 220 nm (Method A); ESI/MS m/e 507.2 ($M^+$+H, $C_{29}H_{34}N_2O_4S$).

Example 263

Preparation of 1-(tert-Butyloxycarbonyl)-4-(3-hydroxy-3-(3-hydrozyphenyl)-3-phenylpropyl] homopiperazine (Compound No. 294)

1. A solution of di-tert-butyl dicarbonate (25 g, 115 mmol.) in $CH_2Cl_2$ (100 mL) was added over a period of 20 min to a solution of homopiperazine (57 g, 5.0 equiv) in $CH_2Cl_2$ (200 mL). The reaction mixture was stirred at room temperature for 3 days. $H_2O$ (150 mL) was added to the reaction mixture and the mixture was extracted with $CH_2Cl_2$ (2×100 mL). The combined extracts were washed with brine and dried over $MgSO_4$. The solvent was removed under reduced pressure to afford an oil which was purified by simple distillation to give 1-(tert-butyloxycarbonyl) homopiperazine: 13.68 g, 59% yield, colorless oil: The purity was determined by GC/MS (95%), m/e 200.1 ($M^+$, $C_{10}H_{20}N_2O_2$).

2. 3-Chloropropiophenone (7.14 g, 24.4 mmol). $K_2CO_3$ (8.79 g, 1.50 equiv) and KI (1.41 mg, 0.2 equiv) were added to a solution of the purified 1-(tert-butyloxycarbonyl) homopiperazine (8.486 g, 42.4 mmol) in $CH_3CN$ (60 mL). The reaction mixture was stirred at 70° C. for 17 h and then AcOEt (200 mL) was added to the cooled mixture. The precipitated solid was removed by filtration and washed with AcOEt (50 mL). The combined filtrate was evaporated to afford an oil which was purified by column chromatography ($SiO_2$, 0%–20% $CH_3CN$/AcOEt) to give 1-(tert-Butyloxycarbonyl)-4-(3-phenyl-3-oxopropyl) homopiperazine: 11.27 g, 80% yield, pale yellow oil: $^1H$ NMR ($CDCl_3$, 300 MHz) δ 1.40–1.65 (m, 9H), 1.80–1.95 (m, 2H), 2.65–2.85 (m, 4H), 3.01 (t, 2H, J=6.9 Hz), 3.19 (t, 2H, J=6.9 Hz), 3.35–3.55 (m, 4H), 7.47 (t, 2H, J=7.7 Hz), 7.55–7.65 (m, 1H), 7.90–8.02 (m, 2H). The purity was determined by RPLC/MS (Method B). RPLC $t_R$=5.53 min (95%), 220 nm; ESI/MS m/e 333.4 ($M^+$+H, $C_{19}H_{29}N_2O_3$).

3. A solution of 3-(tert-butyldimethylsilyloxy) phenylmagnesium bromide [prepared from 3-(tert-butyldimethylsilyloxy)bromobenzene (28.5 g, 99.2 mmol) and magnesium turnings (2.30 g, 94.5 mmol) in $Et_2O$ (65 mL) I was added at 0° C. to a solution of the purified 1-(tert-Butyloxycarbonyl)-4-(3-phenyl-3-oxopropyl) homopiperazine (11.25 g, 33.8 mmol) in dry THF (150 mL). The mixture was warmed to room temperature with stirring and the stirring was continued for 3 h. Saturated aqueous $NH_4Cl$ (300 mL) was added to the reaction mixture, the mixture was stirred for 15 min and extracted with AcOEt (3×150 mL). The combined extracts were washed with brine and dried over $MgSO_4$. The solvent was removed under reduced pressure to afford an oil (31.00 g) which was purified by column chromatography ($SiO_2$, 3%–25% AcOEt/hexane) to give 1-(tert-butyloxycarbonyl)-4-[3-{3-(tert-butyldimethylsilyloxy)phenyl}-3-hydroxy-3-phenylpropyl]homopiperazine : 9.00 g, 49% yield, pale yellow oil; $^1H$ NMR ($CDCl_3$, 300 MHz) δ 0.00 (s, 6H), 0.81 (s, 9H), 1.32 (s, 9H), 1.4–1.5 (m, 2H), 1.7–1.8 (m, 2H), 2.2–2.3 (m, 2H), 2.4–2.55 (m, 4H), 3.25–3.45 (m, 4H), 6.50–6.56 (m, 1H), 6.80–6.92 (m, 2H), 6.99–7.10 (m, 2H), 7.11–7.20 (m, 2H), 7.28–7.34 (m, 2H), The purity was determined by RPLC/MS (Method A). RPLC $t_R$=7.13 min (>95%), 220 nm: ESI/MS m/e 541.3 ($M^+$+H, $C_{31}H_{49}N_2O_2Si$).

4. A solution of tetrabutylammonium fluoride (1.0 M solution in THF, 4.0 mL, 4.0 mmol, 1.03 equiv) was added to a solution of the purified 1-(tert-butyloxycarbonyl)-4-[3-{3-(tert-butyldimethylsilyloxy)phenyl}-3-hydroxy-3-phenylpropyl]homopiperazine (2.11 g, 3.90 mmol) in THF (35 mL). The mixture was stirred at room temperature for 30 min. $H_2O$ (100 mL) was added to the reaction mixture and the mixture was extracted with AcOEt (3×100 mL). The combined extracts were washed with brine and dried over $MgSO_4$. The solvent was removed under reduced pressure to afford an oil (3.11 g) which was purified by column chromatography ($SiO_2$, 50% ACOEt/hexane) to give 1-(tert-butyloxycarbonyl)-4-[3-hydroxy-3-(3-hydroxyphenyl)-3-phenylpropyl]homopiperazine (compound No. 294): 1.381 g, 83% yield, colorless oil; $^1H$ NMR ($CDCl_3$, 300 MHz) δ 1.47 (s, 3H), 1.50 (s, 6H), 1.9–2.1 (m, 2H), 2.45–2.9 (m, 8H), 3.3–3.8 (m, 4H), 6.7–7.0 (m, 2H), 7.05–7.28 (m, 2H), 7.3–7.38 (m, 2H), 7.42–7.50 (m, 2H). The purity was determined by RPLC/MS (Method A). RPLC $t_R$=5.30 min (>95%), 220 m: ESI/MS m/e 427.3 ($M^+$+H, $C_{25}H_{35}N_2O_4$).

Example 264

Preparation of 1-[3-Hydroxy-3-(3-hydrozyphenyl)-3-phenylpropyl]homopiperazine (Compound No. 295)

p-Toluenesulfonic acid monohydrate (1.90 g, 10.0 mmol, 4.0 equiv) was added to a solution of the purified 1-(tert-butyloxycarbonyl)-4-(3-hydroxy-3-(3-hydroxyphenyl)-3-phenylpropyl]homopiperazine (Compound No. 294, 1.066 g, 2.50 mmol) in $CH_3CN$ (15 mL)). The reaction mixture was stirred at room temperature for 2.0 h and then. $H_2O$ (50 mL) and $CH_3OH$ (20 mL) were added. Anion exchange resin (11.5 g, DOWEX 1×2–200, washed with aqueous NaOH) was added and the mixture was gently agitated at room temperature for 5 min. The resin was removed by filtration and washed with $CH_3OH$ (300 mL). The combined filtrate was evaporated to afford an oil (1.35 g) which was purified by column chromatography ($SiO_2$, 5%–>10% $CH_3OH$, 5% $TEA/CH_2Cl_2$) to give 1-[3-hydroxy-3-(3-hydroxyphenyl)-3-phenylpropyl]homopiperazine (Compound No. 295): 657 mg, 81% yield, colorless oil; $^1H$ NMR ($CDCl_3$, 300 MHz) δ 1.8–2.0 (m, 2H), 2.35–2.45 (m, 2H), 2.55–2.80 (m, 6H), 3.0–3.15 (m, 4H), 6.68–6.75 (m, 1H), 6.82–6.88 (m, 1H), 7.10–7.38 (m, 5H), 7.42–7.52 (m, 2H). The purity was determined by RPLC/MS (Method B), RPLC $t_R$=4.27 min (>99%), 220 nm; ESI/MS m/e 327.3 ($M^+$+H, $C_{20}H_{27}N_2O_2$).

Example 265

General Alkylation of 1-[3-Hydroxy-3-(3-hydroxyphenyl)-3-phenylpropyl]homopiperazine (Preparation of Compound No. 185)

1-Benzoyl-2-(chloroacetyl)hydrazine (60 mg, 0.281 mmol, 1.2 equiv) and $Et_3N$ (118 mg, 1.17 mmol, 5.0 equiv) were added to a solution of 1-[3-hydroxy-3-(3-hydroxyphenyl)-3-phenylpropyl]homopiperazine (Compound No. 295, 100 mg, 0.306 mmol) in $CH_3CN$ (2.0 mL). The reaction mixture was stirred at 60–70° C. for 13 h. The solvent was evaporated to afford an oil which was purified by column chromatography ($SiO_2$, 10% $CH_3OH$/$CH_2Cl_2$) to give Compound No. 185: 71 mg, 46% yield, colorless oil; $^1$HNMR ($CD_3OD$, 300 MHz) δ 1.85–2.00 (m, 2H), 2.45–2.55 (m, 2H), 2.65–2.75 (m, 2H), 2.78–3.00 (m, 8H), 3.36 (s, 2H), 6.62–6.65 (m, 1H), 6.90–6.98 (m, 2H), 7.10–7.35 (m, 4H), 7.40–7.65 (m, 5H), 7.88 (d, 2H, J=5.4 Hz). The purity was determined by RPLC/MS (Method B). RPLC $t_R$=5.08 min (>98%), 220 nm; ESI/MS m/e 503.2 ($M^+$+H, $C_{29}H_{35}N_4O_4$).

Example 266

Compound No. 259, di-TFA salt (54.8 mg, 15%) was prepared from 1-[3-hydroxy-3-(3-hydroxyphenyl)-3-phenylpropyl]homopiperazine (Compound No. 295, 158 mg, 0.486 mmol) and Maybridge GK02253 (136 mg, 1.2 equiv) employing general alkylation procedure. The product was purified by preparative RPLC. RPLC $t_R$=4.60 min (>98%), 220 nm (Method A); ESI/MS m/e 523,2 ($M^+$+H, $C_{28}H_{35}N_4O_4S$).

Example 267

Compound No. 227 (20 mg, 35%) was prepared from 1-[3-hydroxy-3-(3-hydroxyphenyl)-3-phenylpropyl]homopiperazine (Compound No. 295, 36 mg, 0.11 mmol) and N-(3-bromopropyl)phthalimide (32 mg, 1.1 equiv) employing general alkylation procedure. RPLC $t_R$=5.23 min (98%), 220 nm (Method B); ESI/MS m/e 514.3 (M$^+$+H, $C_{31}H_{36}N_3O_4$).

Example 268

Compound No. 227260 (105 mg, 67%) was prepared from 1-[3-hydroxy-3-(3-hydroxyphenyl)-3-phenylpropyl]homopiperazine (Compound No. 295, 100 mg, 0.306 mmol) and 1-(chloroacetyl)-2-(2-thiophenecarbonl)hydrazine (61 mg, 1.2 equiv) employing general alkylation procedure. RPLC $t_R$=4.95 min (>98%), 220 nm (Method B); ESI/MS m/e 509.2 (M$^+$+H, $C_{27}H_{33}N_4O_4S$).

Example 269

Compound No. 261 (94 mg, 53%) was prepared from 1-[3-hydroxy-3-(3-hydroxyphenyl)-3-phenylpropyl]homopiperazine (Compound No. 295, 100 mg, 0.306 mmol) and Maybridge RF00404 (79 mg, 1.2 equiv) employing general alkylation procedure. RPLC $t_R$=5.52 min (>98%), 220 nm (Method B); ESI/MS m/e 572.2 (M$^+$+H, $C_{28}H_{32}Cl_2N_5O_4$).

Example 270

Compound No. 293 (65 mg, 48%) was prepared from 1-[3-hydroxy-3-(3-hydroxyphenyl)-3-phenylpropyl]homopiperazine (Compound No. 295, 100 mg, 0.306 mmol) and N,N-diethylacetamide (150 mg, 4.3 equiv) employing general alkylation procedure. RPLC $t_R$=4.68 min (89%), 220 nm (Method B); ESI/MS m/e 440.2 (M$^+$+H, $C_{26}H_{38}N_3O_3$).

Example 271

Compound No. 228 (97 mg, 63%) was prepared from 1-[3-hydroxy-3-(3-hydroxyphenyl)-3-phenylpropyl]homopiperazine (Compound No. 295, 100 mg, 0.306 mmol) and 1-(3-chloropropyl)-1,3-dihydro-2H-benzimidazol-2-one (230 mg, 4.6 equiv) employing general alkylation procedure. $t_R$=4.98 min (>95%). 220 nm (Method B); ESI/MS m/e 501.1 (M$^+$+H, $C_{36}H_{37}N_4O_3$).

Example 272

Compound No. 229 (60 mg, 63%) was prepared from 1-[3-hydroxy-3-[3-hydroxyphenyl)-3-phenylpropyl]homopiperazine (Compound No. 295, 59 mg, 0.182 mmol) and 4-bromo-2-butenyl phenyl sulfone (50 mg, 1.0 equiv) employing general alkylation procedure. RPLC $t_R$=5.20 min (>95%), 220 nm (Method B); ESI/MS m/e 521.3 (M$^+$+H, $C_{30}H_{37}N_2O_4S$).

Example 273

Compound No. 262 di-TFA salt (88 mg, 48%) was prepared from 1-[3-hydroxy-3-(3-hydroxyphenyl)-3-phenylpropyl]homopiperazine (Compound No. 295, 80 mg, 0.245 mmol) and 1-(chloroacetyl)-2-(5-methylthiophenecarbonl)hydrazine (68 mg, 1.2 equiv) employing general alkylation procedure. The Product was purified by preparative RPLC. RPLC $t_R$=5.23 min (>98%), 220 nm (Method B); ESI/MS m/e 523.3 (M$^+$+H, $C_{28}H_{35}N_4O_4S$).

Example 274

Compound No. 187 di-TFA salt (19 mg, 9.5%) was prepared from 1-[3-hydroxy-3-(3-hydroxyphenyl)-3-phenylpropyl]homopiperazine (Compound No. 295, 80 mg, 0.245 mmol) and Salor S2.688-4 (88 mg, 1.2 equiv) employing general alkylation procedure. The Product was purified by preparative RPLC. RPLC $t_R$=5.22 min (>85%), 220 nm (Method B); ESI/MS m/e 589.0 (M$^+$+H, $C_{33}H_{37}N_2O_6S$).

Example 275

Compound No. 189 (26 mg, 42%) was prepared from 1-[3-hydroxy-3-(3-hydroxyphenyl)-3-phenylpropyl]homopiperazine (Compound No. 295, 40 mg, 0.123 mmol) and N-(phenacyl)chloroacetamide (32 mg, 1.2 equiv) employing general alkylation procedure. RPLC $t_R$=5.73 min (>98%), 220 nm (Method B); ESI/MS m/e 502.3 (M$^+$+H, $C_{30}H_{36}N_3O_4$).

Preparation of 1-[4-(Bromomethyl)benzenesulfonyl]pyrrole

NaH (60% dispersion in mineral oil. 40 mg, 1.0 mmol) was added to a solution of pyrrole (67 mg, 1.0 mmol) in THF (2.0 mL) and the mixture was stirred at room temperature for 5 min. Then 4-(bromomethyl)benzenesulfonyl chloride (269 mg, 1.0 mmol) was added to the mixture. After stirring at room temperature for additional 10 min, brine (15 mL) was added and the mixture was extracted with AcOEt (40 mL×2). The combined extracts were dried over $MgSO_4$. The solvent was removed under reduced pressure to afford an oil which was purified by column chromatography ($SiO_2$, 10% AcOEt/hexane) to give 1-[4-(bromomethyl)benzenesulfonyl]pyrrole: 46 mg, 15% yield, colorless oil. The purity was determined by GC/MS (>95%), m/e 299 (M$^+$, $C_{11}H_{10}NO_2BrS$).

Example 276

Compound No. 190 (27 mg, 40%) was prepared from 1-[3-hydroxy-3-(3-hydroxyphenyl)-3-phenylpropyl]homopiperazine (Compound No. 295, 40 mg, 0.123 mmol) and 1-[4-(bromomethyl)benzenesulfonyl]pyrrole (46 mg, 1.24 equiv) employing general alkylation procedure. RPLC $t_R$=5.85 min (>98%), 220 nm (Method B); ESI/MS m/e 546.3 (M$^+$+H, $C_{31}H_{36}N_3O_4S$).

Example 277

Compound No. 191 (39 mg, 61%) was prepared from 1-[3-hydroxy-3-(3-hydroxyphenyl)-3-phenylpropyl]homopiperazine (Compound No. 295, 40 mg, 0.123 mmol) and 1-(chloroacetyl)-2-(4-hydroxybenzoyl)hydrazine (28 mg, 1.0 equiv) employing general alkylation procedure. RPLC $t_R$=4.72 min (>95%), 220 nm (Method B); ESI/MS m/e 519.3 (M$^+$+H, $C_{29}H_{35}N_4O_5$).

Example 278

Compound No. 194 di-TFA salt (39 mg, 42%) was prepared from 1-[3-hydroxy-3-(3-hydroxyphenyl)-3-phenylpropyl]homopiperazine (Compound No. 295, 40 mg, 0.123 mmol) and 1-(chloroacetyl)-2-(4-chlorobenzoyl)hydrazine (31 mg, 1.0 equiv) employing general alkylation procedure. The Product was purified by preparative RPLC. RPLC $t_R$=5.48 min (>95%), 220 nm (Method B); ESI/MS m/e 537.0 (M$^+$+H, $Cl_2 9H_{34}ClN_4O_5$).

Example 279

Compound No. 195 di-TFA salt (30 mg, 33%) was prepared from 1-[3-hydroxy-3-(3-hydroxyphenyl)-3-phenylpropyl]homopiperazine (Compound No. 295, 40 mg, 0.123 mmol) and 1-chloroacetyl-4-phenylsemicarbazide (28 mg, 1.0 equiv) employing general alkylation procedure. The Product was purified by preparative RPLC. RPLC $t_R$=5.18 min (>95%)), 220 nm (Method B); ESI/MS m/e 518.3 (M$^+$+H, $C_{29}H_{36}N_5O_4$).

Example 280

Compound No. 231 di-TFA salt (29 mg, 42%) was prepared from 1-[3-hydroxy-3-(3-hydroxyphenyl)-3-phenylpropyl]homopiperazine (Compound No. 295, 30 mg, 0.092 mmol) and bromobimane (28 mg, 1.0 equiv) employing general alkylation procedure. The product was purified by preparative RPLC. RPLC $t_R$=1.87 min (>95%), 220 nm (Method B); ESI/MS m/e 517.4 (M$^+$+H, $C_{30}H_{37}N_4O_4$).

Example 281

Compound No. 196 di-TFA salt (33 mg, 46%) was prepared from 1-[3-hydroxy-3-(3-hydroxyphenyl)-3-phenylpropyl]homopiperazine (Compound No. 295, 30 mg, 0.092 mmol) and Maybridge CD08063 (29 mg, 1.2 equiv) employing general alkylation procedure. The product was purified by preparative RPLC. RPLC $t_R$=2.07 min (>98%), 220 nm (Method B); ESI/MS m/e 557.2 (M$^+$+H, $C_{28}H_{34}ClN_4O_4S$).

Example 282

Compound No. 232 tri-TFA salt (6.6 mg; 9.1%) was prepared from 1-[3-hydroxy-3-(3-hydroxyphenyl)-3-phenylpropyl]homopiperazine (Compound No. 295, 30 mg, 0.092 mmol) and Maybridge TB812299 (18 mg, 1.2 equiv) employing general alkylation procedure. The product was purified by preparative RPLC. RPLC $t_R$=1.48 min (>95%), 220 nm (Method B); ESI/MS m/e 451.2 (M$^+$+H, $C_{25}H_{31}N_4O_4$).

Example 283

Compound No. 296 (16 mg, 18%) was prepared from 1-[3-hydroxy-3-(3-hydroxyphenyl)-3-phenylpropyl] homopiperazine (Compound No. 295, 78 mg, 0.24 mmol) and acetyl chloride (19 mg, 1.0 equiv). Acetyl chloride and Et$_3$N (121 mg, 1.2 mmol, 5.0 equiv) were added to a solution of 1-[3-hydroxy-3-(3-hydroxyphenyl)-3-phenylpropyl] homopiperazine (Compound No. 295) in CH$_3$CN (2.0 mL). The reaction mixture was stirred at room temperature for 30 min. saturated aqueous NaHCO$_3$ (10 mL) was added to the reaction mixture and the mixture was extracted with AcOEt (3×15 mL). The combined extracts were dried over MgSO$_4$. The solvent was removed under reduced pressure to afford an oil which was purified by column chromatography (SiO$_2$, 3–10% CH$_3$OH/CH$_2$Cl$_2$) to give 1-acetyl-4-[3-hydroxy-3-(3-hydroxyphenyl)-3-phenylpropyl]homopiperazine (Compound No. 296): 16 mg, 18% yield, colorless oil: RPLC $t_R$=4.75 min (89%), 220 nm (Method B); ESI/MS m/e 369.3 (M$^+$+H, $C_{22}H_{29}N_2O_3$).

Example 284

Compound No. 263 TFA salt (40 mg, 23%) was prepared from 1-[3-hydroxy-3-(3-hydroxyphenyl)-3-phenylpropyl] homopiperazine (Compound No. 295, 80 mg, 0.25 mmol), 2-(4-chlorobutyryl)thiophene (70 mg, 0.3 mmol) and triethylamine (174 mL, 1.25 mmol) employing general alkylation procedure. TLC $R_f$=0.58 (5% Et$_3$N-10% CH$_3$OH—CH$_2$Cl$_2$); RPLC $t_R$=4.98 min (>85%), 220 nm (Method B); ESI/MS m/e 479.3 (M$^+$+H, $C_{28}H_{34}N_2O_3S$).

Example 285

Compound No. 188 TFA salt (31 mg, 17%) was prepared from 1-[3-hydroxy-3-(3-hydroxyphenyl)-3-phenylpropyl] homopiperazine (Compound No. 295, 80 mg, 0.25 mmol), 3-chloropropyl p-tolyl sulfone (70 mg, 0.3 mmol) and triethylamine (174 mL, 1.25 mmol) employing general alkylation procedure. TLC $R_f$=0.62 (5% Et$_3$N-10% CH$_3$OH—CH$_2$Cl$_2$); RPLC $t_R$=5.25 min (>85%), 220 nm (Method B); ESI/MS m/e 523.3 (M$^+$+H, $C_{30}H_{38}N_2O_4S$).

Example 286

Compound No. 192 TFA salt (34 mg, 19%) was prepared from 1-[3-hydroxy-3-(3-hydroxyphenyl)-3-phenylpropyl] homopiperazine (Compound No. 295, 80 mg, 0.25 mmol), 4-(chloroacetyl)catechol (56 mg, 0.3 mmol) and triethylamnine (174 mL, 1.25 mmol) employing general alkylation procedure. TLC $R_f$=0.62 (5% Et$_3$N-10% CH$_3$OH—CH$_2$Cl$_2$), RPLC $t_R$=4.68 min (>85%), 220 nm (Method B); ESI/MS m/e 477.3 (M$^+$+H, $C_{28}H_{32}N_2O_3$).

Example 287

Compound No. 230 TFA salt (30 mg, 17%) was prepared from 1-[3-hydroxy-3-(3-hydroxyphenyl)-3-phenylpropyl] homopiperazine (Compound No. 295, 80 mg, 0.25 mmol), glycidyl methacrylate (43 mg, 0.3 mmol) and triethylamine (174 mL, 1.25 mmol) employing general alkylation procedure. TLC $R_f$=0.6 (5% Et$_3$N-10% CH$_3$OH—CH$_2$Cl$_2$), RPLC $t_R$=4.95 min (90%), 220 nm (Method B); ESI/MS m/e 469.0 (M$^+$+H, $C_{27}H_{36}N_2O_5$).

Example 288

Compound No. 193 TFA salt (44 mg, 49%) was prepared from 1-[3-hydroxy-3-(3-hydroxyphenyl)-3-phenylpropyl] homopiperazine (Compound No. 295, 50 mg, 0.15 mmol), 2-chloro-4'-fluoro-3'-nitroacetanilide (50 mg, 0.12 mmol) and triethylamine (104 mL, 0.75 mmol) employing general alkylation procedure. TLC $R_f$=0.6 (5% Et$_3$N-10% CH$_3$OH—CH$_2$Cl$_2$); RPLC $t_R$=5.78 min (>85%), 220 nm (Method B); ESI/MS m/e 523.0 (M$^+$+H, $C_{28}H_{31}N_4O_5F$).

Preparation of 1-[3-(3-Hydroxyphenyl) 3phanylprapyl]homopiperazine

1. Trifluoroacetic acid (4.75 mL) was added to a solution of 1-[3-hydroxy-3-(3-hydroxyphenyl)-3-phenylpropyl] homopiperazine (Compound No. 295, 60 mg, 0.184 mmol) in CH$_2$Cl$_2$ (0.25 mL). The reaction mixture was stirred at room temperature for 2.5 h. The trifluoroacetic acid was evaporated to afford 1-[3-(3-hydroxyphenyl)-3-phenyl-2-propenyl]homopiperazine as a colorless oil used without further purification.

2. A solution of 1-[3-(3-hydroxyphonyl)-3-phenyl-2-propenyl]homoplperazjme in EtOH (6 mL was hydrogenated at 1 atm for 1.5 h in the presence of 5% palladium on charcoal (60 mg) at room temperature. The catalyst was removed by filtration through Cellte and washed with ETOH (30 mL). The combined filtrate was evaporated to give 1-[3-(3-hydroxyphenyl)-3-phenylpropyl]homopiperazine (2TFA salt, 100 mg, quantitative) as a white solid used without further purification. RPLC $t_R$=1.62 min (Method B); ESI/MS m/e 311.2 (M$^+$+H, $C_{20}H_{27}N_2O$).

Example 289

General Alkylation of 1-[3-(3-Hydroxyphenyl)-3-phenylpropyl]homopiperazine (Preparation of Compound No. 257)

Maybridge GK02253 (17 mg, 0.074 mmol, 1.2 equiv) and Et$_3$N (37 mg, 0.37 mmol, 6.0 equiv) were added to a solution of 1-[3-(3-hydroxyphenyl)-3-phenylpropyl]homopiperazine 2TFA salt (33 mg, 0.061 mmol) in $CH_3CN$ (2.0 mL). The reaction mixture was stirred at 70° C. for 15 h. The solvent was evaporated to afford an oil which was purified by preparative RPLC to give Compound No. 257 di-TFA salt: 8.0 mg, 18% yield, colorless oil. The purity was determined by RPLC/MS. RPLC $t_R$=1.90 min (>95%), 220 nm (Method B); ESI/MS m/e 507.2 ($M^+$+H, $C_{20}H_{35}N_4O_3S$).

Example 290

Compound No. 101 di-TFA salt (6.0 mg, 14%) was prepared from 1-[3-(3-hydroxyphenyl)-3-phenylpropyl]homopiperazine di-TFA salt (33 mg, 0.061 mmol) and N-(phenacyl)chloroacetamide (16 mg, 1.2 equiv) employing general alkylation procedure. The product was purified by preparative RPLC. RPLC $t_R$=1.92 min (>85%), 220 nm (Method B); ESI/MS m/e 486.2 ($M^+$+H, $C_{30}H_{36}N_3O_3$).

Preparation of 1-(3,3-Diphenylpropyl)piperazine 1-(tert-butyloxycarbonyl)piperazine (1.00 g, 5.4 mmol) was dissolved in $CH_3CN$ (27 mL) and was treated with 3,3-diphenylpropyl mesylate (1.6 g, 5.6 mmol, 1.05 equiv) and $^iPrNEt$ (1.40 mL, 8.05 mmol, 1.5 equiv). The reaction mixture was heated to 70° C. for 16 h, cooled and concetrated, The residue was purified by chromatography ($SiO_2$, 1% $CH_3OH$—$CH_2Cl_2$) to afford the desired Boc-protected material (988 mg, 48%). The product was treated with 3 M HCl—$CH_3OH$ (26 mL) and stirred at 25° C. for 1 h. The solvent was removed in vacuo and the residue was dissolved in $^tBuOH$-$H_2O$ (26 mL). Dowex 500 anion exchange resin was added until pH=9. The resin was filtered and solution concetrated to afforded the desired product (702 mg, 98%).

General Alkylation of 1-(3,3-Diphenylpropyl)piperazine 1-(3,3-Diphenylpropyl)piperazine (50 mg, 0.178 mmol) was dissolved in $CH_3CN$ (1 mL) and was treated with alkylating agent (0.196 mmol, 1.1 equiv) and $^iPrNEt$ 40 μL, 0.232 mmol, 1.3 equiv). The reaction mixture was heated to 70° C. for 16 h. The solvent was removed and the samples were purified by normal column chromatography or preparative RPLC.

Example 291

Compound No. 236 (di-TFA salt, 72 mg, 53%) was prepared from 1-(3, 3-diphenylpropyl )piperazine (50 mg, 0.178 mmol) and Maybridge GK 02253 (46 mg, 0.196 mmol) employing general alkylation procedure. RPLC $t_R$=2.12 min (>90%), 220 nm (Method A ); ESI/MS m/e 477.2 ($M^+$+H, $C_{27}H_{32}N_4O_2S$).

Example 292

Compound No. 10 (di-TFA salt, 36 mg, 27%) was prepared from 1-(3,3-diphenylpropyl )piperazine (50 mg, 0.178 mmol) and N-(phenacyl)chloroacetamide (42 mg, 0.196 mmol) employing general alkylation procedure. RPLC $t_R$=2.41 min (>95%), 220 nm (Method A); ESI/MS m/e 456.5 ($M^+$+H, $C_{29}H_{33}N_3O_2$).

Example 293

Compound No. 11 (di-TFA salt, 76 mg, 57%) was prepared from 1-(3,3-diphenylpropyl )piperazine (50 mg, 0.178 mmol) and 1-benzoyl-2-(chloroacetyl)hydrazine (42 mg, 0.196 mmol) employing general alkylation procedure. RPLC $t_R$=2.26 min (>95%), 220 nm (Method A); ESI/MS m/e 457.4 ($M^+$+H, $C_{28}H_{32}N_4O_2$).

Example 294

Compound No. 12 (di-TFA salt, 54 mg, 46%) was prepared from 1-(3,3-diphenylpropyl)piperazine (50 mg, 0.178 mmol) and 2-hydroxy-5-nitrobenzyl bromide (46 mg, 0.196 mmol) employing general alkylation procedure. RPLC $t_R$=2.20 min (>95%), 220 nm (Method A); ESI/MS m/e 432.2 ($M^+$+H, $C_{26}H_{29}N_3O_3$).

Example 295

Compound No. 13 (43 mg, 49%) was prepared from 1-(3,3-diphenylpropyl)piperazine (50 mg, 0.178 mmol) and N-(4-methoxy-2-nitrophenyl)-2-bromoacetamide (46 mg, 0.196 mmol) employing general alkylation procedure. RPLC $t_R$=2.66 min (>95%), 220 nm (Method A); ESI/MS m/e 489.2 ($M^+$+H, $C_{28}H_{32}N_4O_4$).

Example 296

Compound No. 14 (55 mg, 62%) was prepared from 1-(3,3-diphenylpropyl)piperazine (50 mg, 0.178 mmol) and N-(4-acetamido-3-methoxyphenyl)-2-bromoacetamide (46 mg, 0.196 mmol) employing general alkylation procedure. RPLC $t_R$=2.27 min (>95%), 220 nm (Method A); ESI/MS m/e 501.2 ($M^+$+H, $C_{30}H_{36}N_4O_3$).

Example 297

Measurement of Inhibition of MIP-1α Binding to THP-1 Cells by Test Compounds

Human monocytic leukemia cell line THP-1 was suspended in assay buffer (RPMI-1640 (Gibco-BRL Co.) containing 0.1% BSA and 25 mM HEPES adjusted to pH 7.4) to give a cell suspension of a concentration of $1\times10^7$ cells/mL. The test compound was diluted in the assay buffer and used as the test compound solution. Iodinated human MIP-1α (DuPont NEN Co.) was diluted in assay buffer to 250 nCi/mL and used as the ligand solution. In a 96 well filter plate (Millipore Co.), 25 μL of test compound solution. 25 μL of labeled ligand solution and 50 μL of cell suspension were aliquoted into each well in this order, stirred (total reaction volume 100 μL), and incubated for one hour at 18° C.

After the reaction, the reaction solution was filtered, and the filter was washed twice with 200 μL of cold PBS (200 μL of cold PBS was added and then filtered). The filter was removed and placed in an RIA tube (Iuchi Seieido Co.) and the radioactivity retained by the cells on the filter were measured using a gamma counter (Aloka Co.).

To calculate the ability of test compounds to inhibit binding of human MIP-1α to THP-1 cells, non-specific binding determined by adding 100 ng of unlabeled human MIP-1α (Peprotech Co.) in place of the test compound was subtracted, while the counts with no test compound added was taken as 100%.

Inhibition (%)=(1−(A−B)/(C−B))×100

(A, counts with test compound added: B, counts with 100 ng of unlabeled human MIP-1α added: C, counts with [$^{125}$I]-labeled human MIP-1α added).

When inhibition by the cyclic diamine derivative of this invention was measured, for example, the following compounds demonstrated >20% inhibitory activity at 100 μM.

These compounds are compound Nos. 1, 2, 3, 9, 34, 50, 52, 53, 54, 57, 59, 63, 64, 65, 66, 71, 75, 76, 78, 79, 80, 81, 82, 106, 107, 108, 109, 111, 112, 123, 197, 204, 210, 211, 212, 213, 215, 216, 218, 220, 221, 222, 223, 233, 246, 250, 252, 253, 258, 264, 265, 269, 270, and 297.

Example 298

Measurement of Inhibition of MCP-1 Binding to TP-1 Cells

1. Construction of Recombinant Baculovirus Carrying the Human MCP-1 Gene

Based on the previously published human MCP-1 gene sequence (for example T. Yoshimura et al., Febs Letters, 1989, 244, 487–493), two synthetic DNA primers (5'-CACTCTAGACTCCAGCATGA-3' and 5'-TAGCTGCAGATTCTTGGGTTG-3') flanked by restriction enzyme sites were used to amplify a DNA fragment from cDNA derived from human endothelial cells (purchased from Kurabow Co.); the amplified fragment was cut with the restriction enzymes (PstI and XbaI), ligated into a transfer vector pVL1393 (Invitrogen Co.), and the resulting vector was co-transfected along with infectious baculovirus into Sf-9 insect cells and the supernatant was plaque assayed to yield human MCP-1 gene baculovirus recombinant.

2. Synthesis of $[^{125}I]$-labeled Human MCP-1 Expressed in Baculovirus

Using the method of K. Ishii et al. (Biochem Biophys Research Communications 1995, 206, 955–961), 5×10⁶ Sf-6 insect cells was infected with 5×10⁷ PFU (plaque forming units) of the above human MCP-1 recombinant baculovirus and cultured for 7 days in Ex-Cell 401 medium. The culture supernatant was affinity purified using a heparin Sepharose column (Pharmacia Co.) and then further purified using reverse phase HPLC (Vydac C18 column) to prepare purified human MCP-1. The purified human MCP-1 was protein labeled by Amersham Co. using the Bolton Hunter method to yield $[^{125}I]$-labeled baculovirus expressed human MCP-1 (specific activity 2000 Ci/mmol).

3. Measurement of Inhibition of Binding of $[^{125}I]$-labeled Baculovirus Expressed Human MCP-1 to THP-1 Cells Human monocytic leukemia cell line THP-1 was suspended in assay buffer (RPMI-1640 (Gibco-BRL Co.) containing 0.1% BSA and 25 mM HEPES adjusted to pH 7.4) to give a cell suspension of a concentration of 1×10⁷ cells/mL. The test compound was diluted in the assay buffer and used as the test compound solution. $[^{125}I]$-labeled human MCP-1 described above was diluted in assay buffer to 1 mCi/mL and used as the labeled ligand solution. In a 96 well filter plate (Millipore Co.), 25 μL of test compound solution, 25 μL of labeled ligand solution and 50 μL of cell suspension were aliquoted into each well in this order, stirred (total reaction volume 100 μL), and incubated for one hour at 18° C.

After the reaction, the reaction solution was filtered, and the filter was washed twice with 200 μL of cold PBS (200 μL of cold PBS was added and then filtered). The filter was removed and placed in an RIA tube (Iuchi Seieido Co.,), and the radioactivity retained by the cells on the filter were measured using a gamma counter (Aloka Co.).

To calculate the ability of test compound to inhibit binding of human MCP-1 to THP-1 cells, non-specific binding determined by adding 100 ng of unlabeled human MCP-1 in place of the test compound was subtracted, while the counts with no test compound added was taken as 100%.

Inhibition (%)=(1−(A−B)/(C−B))×100

(A, counts with test compound added; B, counts with 100 ng of unlabeled human MIP-1α added; C, counts with $[^{125}I]$-labeled human MCP-1 added).

When inhibition by the cyclic diamine derivative of this invention was measured, for example, the following compounds demonstrated >20% inhibitory activity at 100 μM. These compounds are compound Nos. 1, 2, 3, 4, 9, 10, 11, 36, 50, 51, 52, 55, 56, 58, 59, 61, 63, 64, 65, 67, 68, 69, 72, 73, 75, 76, 78, 80, 82, 83, 84, 85, 86, 87, 88, 89, 90, 91, 92, 93, 96, 98, 99, 100, 101, 103, 104, 106, 107, 108, 109, 114, 116, 117, 119, 121, 122, 123, 124, 125, 126, 128, 129, 131, 132, 133, 134, 135, 136, 137, 138, 139, 140, 141, 142, 143, 145, 146, 147, 148, 149, 151, 152, 153, 154, 155, 156, 157, 158, 159, 160, 161, 162, 185, 186, 187, 188, 189, 190, 191, 192, 193, 194, 195, 196, 213, 214, 215, 220, 221, 222, 223, 224, 225, 226, 227, 228, 229, 230, 231, 232, 233, 234, 236, 246, 248, 249, 251, 252, 253, 254, 255, 256, 257, 258, 259, 260, 261, 262, 263, 264, 265, 267, 269, 271, 272, 273, 274, 275, 276, 277, 278, 279, 280, 281, 282, 284, 287, 288, 293, 294, 295, 296, 298, and 299.

Example 299

Measurement of Inhibition of Binding of $[^{125}I]$-labeled Human MCP-1 to Cells Expressing the MCP-1 Receptor 1. Derivation of Cells Expressing the MCP-1 Receptor cDNA fragment containing the MCP-1 receptor reported by S. Yamagami et al., Biochemical Biophysical Research Communications 1994, 202, 1156–1162) was cloned into the expression plasmid pCEP4 (Invitrogen Co.) at the NotI site, and the plasmid obtained was transfected into the human kidney epithelial cell line 293-EBNA using the Lipofectamine reagent (Gibco-BRL Co.). The cells were cultured in the presence of the selective agent (Hygromycin), and a stably expressing transfectant line was obtained. The express ion of the receptor was confirmed by binding of $[^{125}I]$-labeled human MCP-1.

2. Measurement of Inhibition of Binding of $[^{125}I]$-labeled Baculovirus Expressed Human MCP-1 to the MCP-1 Receptor Expressing Cells The MCP-1 receptor expressing cells on tissue culture dishes were scraped using a call scraper and suspended in assay buffer (D-MEM(Gibco-BRL Co.) containing 0.1% BSA and 25 mM HEPES adjust ed to pH 7.4) to give a cell suspension of a concentration of 6×10⁶ cellls/mL. The test compound was diluted in the assay buffer to concentrations of 0.16, 0.8, 4.20, and 100 μM. The remainder of the procedure was as described in Example 163.

When inhibition by the cyclic diamine derivative of this invention was measured, compound No. 36 for example showed dose dependent inhibition with 50% inhibitory concentration (IC₅₀) of 17 μM.

Example 300

Measurement of Inhibition of Cell Chemotaxis

In order to determine the inhibition of call chemotaxis by the compounds of this invention, we measured call chemotaxis caused by monocyte chemotactic factor MCP-1 using the human monocytic leukemia cell line THP-1 as the chemotactic cell according to the method of Fall et al. (J. Immunol. Methods, 190, 33, 239–247). 2×10⁶ cells/mL of THP-1 cells (suspended in RPMI-1640 (Flow Laboratories Co.) +10% FCS) was placed in the upper chamber (200 μL) of a 96 well micro-chemotaxis chamber (Neuroprobe, registered tradename), and human recombinant MCP-1 in a same solution (Peprotech Co.) at a final concentration of 20 ng/mL was placed in the lower chamber, with a polycarbonate filter (PVP-free, Neuroprobe; registered tradename) placed between the two chambers, These were incubated at 37° C. for 2 hr in 5% $CO_2$.

The filter was removed, and the cells which had migrated to the underside of the filter was fixed, stained using Diff Quick (Kokusai Shiyaku Co.) and then quantitated using a plate reader (Molecular Device Co.) at a wavelength of 550 nm to determine the index of cell migration as a mean of 3 wells, In addition. test compounds were placed in the upper chamber along with THP-1, and the inhibition of cell migration (inhibition $IC_{50}$ (μM)) was determined. Inhibition was defined as ((cells migration induced MCP-1 with no test compound in the upper chamber)–(cells migration with no MCP-1 added in the lower chamber)=100%), and the concentration of the test compound which gave 50% inhibition was designated $IC_{50}$.

When the inhibition of cyclic diamine derivatives of the present invention was measured, the 50% inhibition concentration ($IC_{50}$) for compound No. 36 was 9 μM and for compound No. 240 was 30 μM.

Example 301

Inhibition of Delayed Type Hypersensitivity Reaction in the Mouse DNFB Induced Contact Hypersensitivity Model 7 week old male Balb/c mice (Charles River Co.) were maintained for 1 week, after which the hair was shaved with an electric razor from the abdomen to the chest. 1 day and 2 days later, the shaved areas were painted twice with 25 μL of 0.5% dinitrofluorobenzene (DNFB) (Wako Pure Chemicals Co.) in acetone:olive oil=4:1. At day 6, both side of the right ear was painted for an induction with 10 μL of 0.2% dinitrofluorobenzene (DNFB) (Wako Pure Chemicals Co.) in acetone:olive oil=4:1, while the left ear was painted with 10 μL of acetone:olive oil=4:1 not containing DNFB. As a test agent, compound No. 36 or compound No. 240 was dissolved in acetone to 20 mg/mL, and applied twice at 30 min before and after the DNFB induction (25 μL/ear/dose).

In the control group (no drug administration group), the acetone solution not containing any test compound was applied. There were 8 mice per group in both the control group and the experimental group. In order to prevent licking off of the DNFB and test compound, the necklace for mice were used during the study (Natsume Seisakujo Co.). At 48 hr after DNFB induction, ear lobes were sampled using a spring loaded micrometer (Ozaki Seisakujo Co.). The change in the ear lobe thickness was calculated according to the following formula.

Increase=100×((right ear lobe thickness after sensitization–right ear lobe thickness prior to sensitization)/right ear lobe thickness prior to sensitization–(left ear lobe thickness after sensitization–left ear lobe thickness prior to sensitization)/left ear lobe thickness prior to sensitization)

After exanguination, the isolated ear was fixed in formalin, and hematoxylin-eosin stained histopathological sections were prepared for image analysis. Using a digital camera (Fuji Color Service, HC-1000) installed an an upright microscope and a personal computer-(Macintosh 8100/100AV, using Photoshop software), the color images were digitized, and analyzed using a second image analysis software (NIH Image). The parameters measured were epidermal thickening, edema (area of dermal and subcutaneous tissues), and cellular infiltration of tissue (number of nuclei in the dermis and subcutaneous tissues).

Both compounds showed significant inhibitory activity.

What is claimed is:

1. A cyclic diamine selected from the group consisting of a compound of the formula (I) below:

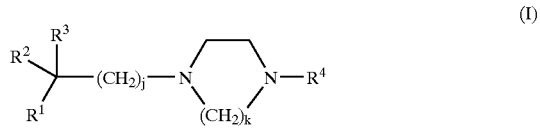

(I)

and a pharmaceutically acceptable acid addition salt thereof
wherein $R^1$ and $R^2$ are the same or different from each other and are phenyl group or aromatic heterocyclic group having 1–3 heteratoms, selected from oxygen atoms, sulfur atoms, nitrogen atoms or combinations thereof, in which the phenyl or aromatic heterocyclic group is optionally substituted by one or more halogen atoms, hydroxy groups, $C_1$–$C_8$ lower alkyl groups, $C_1$–$C_6$ lower alkoxy groups, phenyl groups, benzyl groups, phenoxy groups, methylenedioxy groups, $C_1$–$C_6$ hydroxyalkyl groups, carboxy groups, $C_2$–$C_7$ alkoxycarbonyl groups, $C_2$–$C_7$ alkanoyl amino groups, dioxolanyl groups, or by group represented by the formula: —$NR^5R^6$, or is condensed with a benzene ring to form a condensed ring, wherein the substituents for the phenyl or aromatic heterocyclic group and the condensed ring condensed with a benzene ring are optionally substituted by any substituents independently selected from halogen atoms, hydroxy groups, or $C_1$–$C_6$ lower alkoxy groups, and $R^5$ and $R^6$ are the same or different from each other and are hydrogen atoms, $C_1$–$C_6$ lower alkyl groups, or $C_2$–$C_6$ lower alkenyl groups;

$R^3$ represents a hydrogen atom, hydroxy group, cyano group, $C_1$–$C_6$ lower alkoxy group or $C_2$–$C_7$ lower alkanoyloxy group, j represents an integer of 0–3;

k is 3;

$R^4$ is a group represented by:

1)

wherein $R^7$ is a phenyl group which is optionally substituted with one or more groups which are the same or different and are halogen atoms, hydroxy groups, amino groups, $C_1$–$C_6$ lower alkyl groups, $C_1$–$C_6$ lower alkoxy groups, cyano groups, nitro groups, trifluoromethyl groups, $C_2$–$C_7$ alkoxycarbonyl groups, $C_2$–$C_7$ alkanoyl groups, $C_1$–$C_6$ alkylsulfonyl groups, trifluoromethylsulfonyl groups, (unsubstituted) phenylsulfonyl groups optionally substituted with a hydroxy group, 1-pyrrolylsulfonyl groups, $C_1$–$C_6$ hydroxyalkylsulfonyl groups, $C_1$–$C_6$ alkanoylamino groups, or a group represented by formula: —$CONR^8R^9$ in which $R^8$ and $R^9$, are the same or different from each other, and are hydrogen atoms or $C_1$–$C_6$ lower alkyl groups; $A^1$ is a group represented by the formula: —$(CH_2)_m$— or a group represented by formula: —$(CH_2)_p$—G—$(CH_2)_q$— in which G represents $G^1$ or $G^2$ wherein $G^1$ represents —O—, —CO—, —$SO_2$—, —CO—O—, —CONH—, —NHCO—, —NHCONH—, or —NH-$SO_2$—, and $G^2$ is —(C=NH)NH—$SO_2$—, —CO—NH—NH—CO—, —CO—NH—

NH—CO—NR$^{10}$—, —CO—NH—CH$_2$—CO—, —CO—NH—NH—SO$_2$—, or —CO—N(CH$_2$—CO—OCH$_3$)—NH—CO—, R$^{10}$ is a hydrogen atom or a phenyl group; m is an integer of 0–3; p is an integer of 1–3; and q represents 0 or 1;

$$-A^2-R^{11} \qquad 2)$$

wherein A$^2$ is —CO— or —SO$_2$—; R$^{11}$ is:

a) a phenyl group optionally substituted with one or more groups which are the same or different and are halogen atoms, C$_1$–C$_6$ lower alkyl groups, C$_1$–C$_6$ lower alkoxy groups, groups represented by formula —CH$_2$—NR$^{12}$R$^{13}$ or groups represented by the formula:

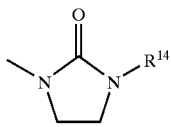

b) an aromatic monocyclic heterocyclic group having 1–3 heteroatoms, selected from oxygen atoms, sulfur atoms, nitrogen atoms or combinations thereof, optionally substituted with one or more groups which are the same or different and are halogen atoms, C$_1$–C$_6$ lower alkyl groups, or C$_1$–C$_6$ lower alkoxy groups, or c) a group of the formula: —CH$_2$—NR$^{15}$R$^{16}$ where R$^{12}$, R$^{13}$, R$^{14}$ and R$^{15}$ are the same or different groups, and are hydrogen atoms, or C$_1$–C$_6$ lower alkyl groups and R$^{16}$ is a phenyl group or a phenylalkyl group optionally substituted with one or more of the same or different groups and are halogen atoms, C$_1$–C$_6$ lower alkyl group, or C$_1$–C$_6$ lower alkoxy group;

$$-(CH_2)_n-R^{17} \qquad 3)$$

wherein n is an integer of 1–4;

and R$^{17}$ represents a hydrogen atom, cyano group, C$_2$–C$_7$ alkoxycarbonyl group, C$_1$–C$_6$ hydroxyalkyl group, C$_2$–C$_6$ lower alkynyl group, C$_3$–C$_6$ cycloalkyl group, C$_3$–C$_7$ alkenoyl group, a group represented by the formula: —(CHOH)CH$_2$OR$^{18}$, a group represented by the formula: —CO—NH—NH—CO—OR$^{19}$, a group represented by the formula:

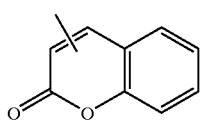

a group represented by the formula:

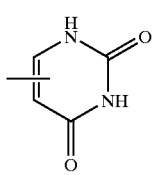

a group represented by the formula:

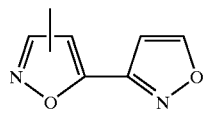

a group represented by the formula:

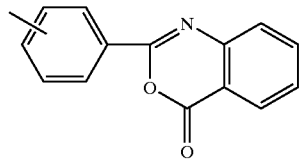

a group represented by the formula:

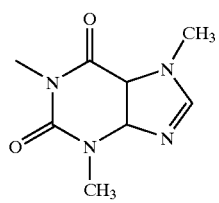

a group represented by the formula:

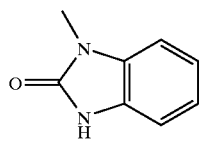

a group represented by the formula:

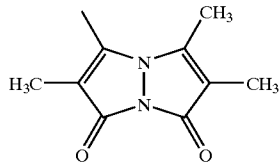

a group represented by the formula:

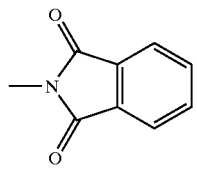

a group represented by the formula:

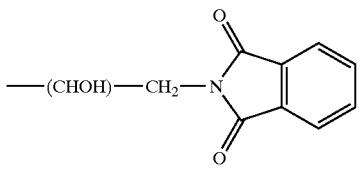

a group represented by the formula:

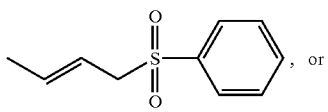, or a group represented by the formula:

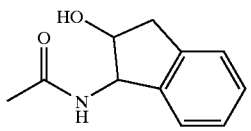

in which n is an integer of 1–4; $R^{18}$ is a $C_1$–$C_6$ lower alkyl group, $C_2$–$C_6$ lower alkenyl group, or $C_2$–$C_6$ lower alkynyl group and $R^{19}$ is a $C_1$–$C_6$ lower alkyl group; wherein $R^{17}$ is a group which, where applicable, is optionally substituted at any possible sites by one or more of the same or different groups, said substituents selected from halogen atoms, hydroxy groups, $C_1$–$C_6$ lower alkoxy groups, or $C_1C_6$ lower alkoxy groups, $$-(CH_2)_r-A^3-R^{20} \qquad 4)$$

wherein r represents an integer of 0–3; $A^3$ represents a single bond, —CO—,

—CO—NH—NH—CO—, —CO—NH—NH—CO—NH—, —CO—NH—CH$_2$—CO—, —CO—NH—NH-SO$_2$—, —(CHOH)—CH$_2$—, or —(CHOH)—CH$_2$OCH$_2$—; $R^{20}$ represents an aromatic heterocyclic group containing 1–3 heteroatoms, selected from oxygen atoms, sulfur atoms, nitrogen atoms or combinations thereof in which the aromatic heterocyclic group is optionally substituted with one or more groups which are the same or different and are halogen atoms, $C_1$–$C_6$ lower alkyl groups, $C_1$–$C_6$ lower alkoxy groups, or pyrrolyl groups or is condensed with a benzene ring to form a condensed ring; or $$-CH_2-CO-NR^{21}R^{22} \qquad 5)$$

wherein $R^{21}$ is a hydrogen atom or a $C_1$–$C_6$ lower alkyl group; $R^{22}$ represents a hydrogen atom, $C_1$–$C_6$ lower alkyl group, or a group represented by the formula:

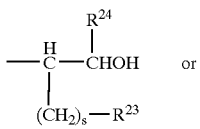 or a group represented by the formula:

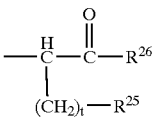

or $R^{21}$ and $R^{22}$ taken together with the nitrogen to which they are attached form a 4 to 7-membered saturated heterocycle, which may contain an oxygen atom, sulfur atom, or another nitrogen atom; where s represents 0 or 1; t represents an integer of 0–2; $R^{23}$ represents a hydrogen atom, hydroxy group, phenyl group, $C_1$–$C_6$ lower alkyl group, or $C_1$–$C_6$ lower alkoxy group; $R^{24}$ represents a hydrogen atom or phenyl group which is optionally substituted with a hydroxy group; $R^{25}$ represents a hydrogen atom, phenyl group which may be substituted by a hydroxy group, $C_2$–$C_7$ alkoxycarbonyl group, $C_1$–$C_6$ lower alkyl group, $C_1$–$C_6$ alkylthio group, or 3-indolyl group; and $R^{26}$ represents a hydroxy group, amino group, $C_1$–$C_6$ lower alkoxy group, or phenylalkyloxy group;

with the proviso that when $R^3$ is a hydrogen atom, then j is not 0;

that when $R^3$ is a hydrogen atom, a substituent for $R^7$ is not a hydroxy, $C_1$–$C_6$ lower alkyl, nor $C_1$–$C_6$ lower alkoxy group;

that when $R^3$ is a hydrogen atom, $G^1$ is not —O— nor —CO—;

that when $R^3$ is a hydrogen atom and $R^{11}$ is a phenyl group, the substituent for $R^{11}$ is not a $C_1$–$C_6$ lower alkyl group;

that when $R^3$ is a hydrogen atom, $R^{17}$ is not a hydrogen atom, $C_2$–$C_7$ alkoxycarbonyl group, nor $C_1$–$C_6$ hydroxyalkyl group;

that when $R^3$ is a hydrogen atom, r is not 0;

that when $R^3$ is a hydrogen atom, $A^3$ is not a single bond or —CO—;

that when $R^3$ is a cyano group, then $R^7$ is not unsubstituted;

that when $R^3$ is a cyano group, a substituent for $R^7$ is not a halogen atom, $C_1$–$C_6$ lower alkyl group, nor $C_1$–$C_6$ lower alkoxy group;

that when $R^3$ is a hydrogen atom and j is not 0, then $R^7$ is not a 2-methoxyphenyl group and $R^4$ is not a —CH$_2$—CONH—$R^7$ nor (CH$_2$)—CO—$R^{20}$; and that when $R^3$ is a cyano group or hydroxy group, then $R^{20}$ is not a pyridyl group.

2. A cyclic diamine or its pharmacologically acceptable acid addition salt as set forth in claim 1, wherein j is 2 in formula (I).

3. A cyclic diamine or its pharmacologically acceptable acid addition salt as set forth in claim 1, wherein $R^3$ is a hydrogen atom in formula (I).

4. A cyclic diamine or its pharmacologically acceptable acid addition salt as set forth in claim 1, wherein $R^3$ is a hydroxyl group in formula (I).

5. A cyclic diamine or its pharmacologically acceptable acid addition salt as set forth in claim 1, wherein $R^1$ and $R^2$ are the same or different from each other and are substituted or unsubstituted phenyl group in formula (I).

6. A cyclic diamine or its pharmacologically acceptable acid addition salt as set forth in claim 1, wherein $R^4$ in formula (I) is a group of the formula —CH$_2$—$R^7$ wherein $R^7$ is as defined for $R^7$ in formula (I).

7. A cyclic diamine or its pharmacologically acceptable acid addition salt as set forth in claim 1, wherein $R^4$ is —$CH_2$—CO—NH—NH—CO—$R^7$, —$CH_2$—CO—NH—NH—CO—$CH_2$—$R^7$, —$CH_2$—CO—NH—NH—CO—NH—$R^7$, —$CH_2$—CO—NH—$CH_2$—CO—$R^7$, —$CH_2$—CO—NR—NH—CO—$R^{20}$, —$CH_2$—CO—NH—NH—CO—NH—$R^{20}$ or —$CH_2$—CO—NH—$CH_2$—CO—$R^{20}$ wherein $R^7$ and $R^{20}$ are as defined for $R^7$ and $R^{20}$ in formula (I).

8. A method for treating diseases such as atherosclerosis, rheumatoid arthritis, psoriasis, asthma, ulcerative colitis, glomerulonephritis, multiple sclerosis, pulmonary fibrosis, or myocarditis in which leukocytes infiltrate into the pathogenic by inhibiting the binding of chemokines to the receptor of a target cell and/or its action on a target cell using a pharmaceutical preparation containing as an effective ingredient, a cyclic diamine, or its pharmacologically acceptable acid addition salt, represented by the formula (II) below:

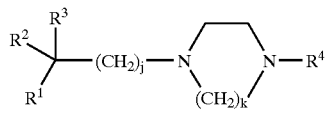

(II)

wherein $R^1$ and $R^2$ are the same or different from each other and are a phenyl group or an aromatic heterocyclic group having 1–3 heteroatoms, selected from oxygen atoms, sulfur atoms, nitrogen atoms or combinations thereof, in which the phenyl or aromatic heterocyclic group is optionally substituted by one or more halogen atoms, hydroxy groups, $C_1$–$C_8$ lower alkyl groups, $C_1$–$C_6$ lower alkoxy groups, phenyl groups, benzyl groups, phenoxy groups, methylenedioxy groups, $C_1$–$C_6$ hydroxyalkyl groups, carboxy groups, $C_2$–$C_7$ alkoxycarbonyl groups, $C_2$–$C_7$ alkanoylamino groups, dioxolanyl groups, or by group represented by the formula: —$NR^5R^6$ or is condensed with a benzene ring to form a condensed ring, wherein the substituents for the phenyl or aromatic heterocyclic group and the condensed ring condensed with a benzene ring are optionally substituted by any substituents independently selected from the group consisting of halogen atoms, hydroxy groups, and $C_1$–$C_6$ lower alkoxy groups, and $R^5$ and $R^6$ are the same or different from each other and are hydrogen atoms, $C_1$–$C_6$ lower alkyl groups, or $C_2$–$C_6$ lower alkenyl groups;

$R^3$ is a hydrogen atom, hydroxy group, cyano group, $C_1$–$C_6$ lower alkoxy group or $C_2$–$C_7$ lower alkanoyloxy group;

j represents an integer of 0–3;

k represents 3;

$R^4$ is a group represented by:

      1)

wherein $R^7$ is a phenyl group which is optionally substituted by one or more groups which are the same or different and are halogen atoms, hydroxy groups, amino groups, $C_1$–$C_6$ lower alkyl groups, $C_1$–$C_6$ lower alkoxy groups, cyano groups, nitro groups, triflouromethyl groups, $C_2$–$C_7$ alkoxycarbonyl groups, $C_2$–$C_7$ alkanoyl groups, $C_1$–$C_6$ alkylsulfonyl groups, triflouromethylsulfonyl groups, unsubstituted phenylsulfonyl groups or phenylsulfonyl groups optionally substituted with a hydroxy group, 1-pyrrolylsulfonyl groups, $C_1$–$C_6$ hydroxyalkylsulfonyl groups, $C_1$–$C_6$ alkanoylamino groups, or a group of the formula: —$CONR^8R^9$ in which $R^8$ and $R^9$ are the same or different from each other, and are hydrogen atoms or $C_1$–$C_6$ lower alkyl groups; $A^1$ is a group of the formula: —$(CH_2)_m$— or a group represented by formula: —$(CH_2)_p$—G—$(CH_2)_q$— in which G is $G^1$ or $G^2$; wherein $G^1$ represents —O—, —CO—, —$SO_2$—, —CO—O—, —CONH—, —NHCO—, —NHCONH—, or —NH—$SO_2$—; and $G^2$ represents —(C=NH)NH—$SO_2$—, —CO—NH—NH—CO—, —CO—NH—NH—CO—$NR^{10}$—, —CO—NH—$CH_2$—CO—, —CO—NH—NH—$SO_2$—, or —CO—N($CH_2$—CO—$OCH_3$)—NH—CO—; $R^{10}$ is a hydrogen atom or a phenyl group; m is an integer of 0–3; p is an integer of 1–3; q represents 0 or 1;

      2)

wherein $A^2$ is —CO— or —$SO_2$—; $R^{11}$ is;

a) a phenyl group which is optionally substituted by one or more groups which are the same or different and are halogen atoms, $C_1$–$C_6$ lower alkyl groups, $C_1$–$C_6$ lower alkoxy groups, groups represented by formula —$CH_2$—$NR^{12}R^{13}$ or groups represented by the formula:

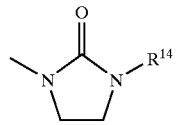

b) an aromatic monocyclic heterocyclic group having 1–3 heteroatoms, selected from oxygen atoms, sulfur atoms, nitrogen atoms or combinations thereof, which is optionally substituted with one or more of the same or different groups which are halogen atoms, $C_1$–$C_6$ lower alkyl groups, or $C_1$–$C_6$ lower alkoxy groups, or c) a group represented by the formula: —$CH_2$—$NR^{15}R^{16}$, where $R^{12}$, $R^{13}$, $R^{14}$ and $R^{15}$, are the same or different groups, and are hydrogen atoms or $C_1$–$C_6$ lower alkyl groups and $R^{16}$ is a phenyl group or a phenylalkyl group, which is optionally substituted by one or more of the same or different groups which are halogen atoms, $C_1$–$C_6$ lower alkyl group, or $C_1$–$C_6$ lower alkoxy group;

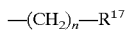      3)

wherein n is an integer of 1–4; and $R^{17}$ is a hydrogen atom, cyano group, $C_2$–$C_7$ alkoxycarbonyl group, $C_1$–$C_6$ hydroxyalkyl group, $C_2$–$C_6$ lower alkynyl group, $C_3$–$C_6$ cycloalkyl group, $C_3$–$C_7$ alkenoyl group, a group represented by the formula: —(CHOH)$CH_2OR^{18}$, a group represented by the formula: —CO—NH—NH—CO—$OR^{19}$, a group represented by the formula:

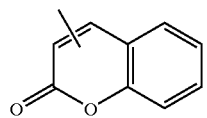

a group represented by the formula:

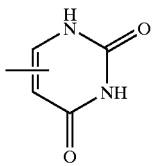

a group represented by the formula:

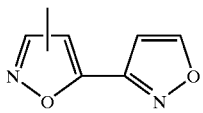

a group represented by the formula:

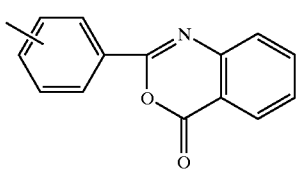

a group represented by the formula:

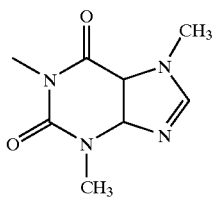

a group represented by the formula:

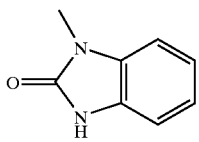

a group represented by the formula:

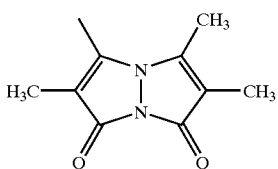

a group represented by the formula

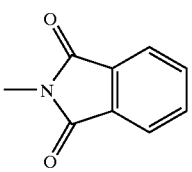

a group represented by the formula

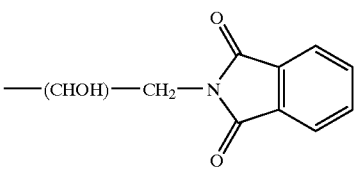

a group represented by the formula

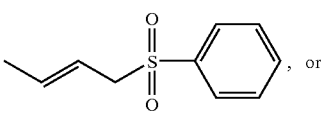, or a group represented by the formula

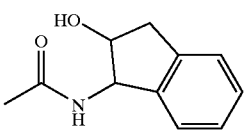

in which n is an integer of 1–4; $R^{18}$ is $C_1$–$C_6$ lower alkyl group, $C_2$–$C_6$ lower alkenyl group, or $C_2$–$C_6$ lower alkynyl group and $R^{19}$ represents a $C_1$–$C_6$ lower alkyl group; wherein $R^{17}$ is a group which, where applicable, is optionally substituted at any possible sites by one or more of the same or different groups, said substituents selected from halogen atoms, hydroxy groups, $C_1$–$C_6$ lower alkyl groups, or $C_1$–$C_6$ lower alkoxy groups, $$—(CH_2)_rA^3—R^{20} \qquad 4)$$

wherein r represents an integer of 0–3; $A^3$ represents a single bond, —CO—, —CO—NH—NH—CO—, —CO—NH—NH—CO—NH—, —CO—NH—CH$_2$—CO—, —CO—NH—NH—SO$_2$—, —(CHOH)—CH$_2$—, or —(CHOH)—CH$_2$OCH$_2$—; $R^{20}$ represents an aromatic heterocyclic group containing 1–3 heteroatoms, selected from oxygen atoms, sulfur atoms, nitrogen atoms or combinations thereof in which the aromatic heterocyclic group is optionally substituted by one or more of the same or different groups which are halogen atoms, $C_1$–$C_6$ lower alkyl groups, $C_1$–$C_6$ lower alkoxy groups, or pyrrolyl groups or is condensed with a benzene ring to form a condensed ring;

$$—CH_2—CO—NR^{21}R^{22} \qquad 5)$$

wherein $R^{21}$ is a hydrogen atom or $C_1$–$C_6$ lower alkyl group; $R^{22}$ represents a hydrogen atom, $C_1$–$C_6$ lower alkyl group, or a group represented by the formula

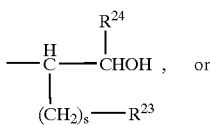

a group represented by the formula

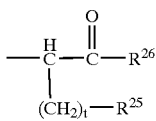

or $R^{21}$ and $R^{22}$ taken together with the nitrogen to which they are attached form a 4 to 7-membered saturated heterocycle, which may contain an oxygen atom, sulfur atom, or another nitrogen atom; where s represents 0 to 1; t represents an integer of 0–2; $R^{23}$ represents a hydrogen atom, hydroxy group, phenyl group, $C_1$–$C_6$ lower alkyl group, or $C_1$–$C_6$ lower alkoxy group; $R^{24}$ represents a hydrogen atom or phenyl group which is optionally substituted with a hydroxy group; $R^{25}$ represents a hydrogen atom, phenyl group which may be substituted by a hydroxy group, $C_2$–$C_7$ alkoxycarbonyl group, $C_1$–$C_6$ lower alkyl group, $C_1$–$C_6$ alkylthio group, or 3-indolyl group; and $R^{26}$ represents a hydroxy group, amino group, $C_1$–$C_6$ lower alkoxy group, or phenylalkyloxy group; or a hydrogen atom, $C_1$–$C_6$ alkanoyl group, or $C_2$–$C_7$ alkoxycarbonyl group.  6)

9. A method according to claim 8, wherein j is 2 in said formula (II) or its pharmacologically acceptable acid addition salt thereof.

10. A method according to claim 8, in which $R^3$ is a hydrogen atom in said formula (II) or its pharmacologically acceptable acid addition salt thereof.

11. A method according to claim 8, in which $R^3$ is a hydroxyl group in said formula (II) or its pharmacologically acceptable acid addition salt thereof.

12. A method according to claim 8, in which $R^1$ and $R^2$ are the same or different from each other and are substituted or unsubstituted phenyl group in said formula (II) or its pharmacologically acceptable acid addition salt thereof.

13. A method according to claim 8, in which $R^4$ is a group of the formula: —$CH_2$—$R^7$ wherein $R^7$ is as defined for $R^7$ in said formula (II), or its pharmacologically acceptable acid addition salt thereof.

14. A method according to claim 8, in which $R^4$ is a group of the formula: —$CH_2$—$R^{20}$ wherein $R^{20}$ is as defined for $R^{20}$ in said formula (II), or its pharmacologically acceptable acid addition salt thereof.

15. A method according to claim 8, wherein $R^4$ is —$CH_2$—CO—NH—NH—CO—$R^7$, —$CH_2$—CO—NH—NH—CO—$CH_2$—$R^7$, —$CH_2$—CO—NH—NH—CO—NH—$R^7$, —$CH_2$—CO—NH—$CH_2$—CO—$R^7$, —$CH_2$—CO—NH—NH—CO—$R^{20}$, —$CH_2$—CO—NH—NH—CO—NH—$R^{20}$ or —$CH_2$—CO—NH—$CH_2$—CO—$R^{20}$ wherein $R^7$ and $R^{20}$ are as defined for $R^7$ and $R^{20}$ in said formula (II), or its pharmacologically acceptable acid addition salt thereof.

16. A method according to claim 8, wherein the chemokine is MIP-1a.

17. A method according to claim 8, wherein the chemokine is MCP-1.

18. A method according to claim 8, wherein the chemokine is IL-8.

* * * * *